United States Patent
Kato et al.

(10) Patent No.: US 9,527,814 B2
(45) Date of Patent: Dec. 27, 2016

(54) AROMATIC AMINE DERIVATIVE, ORGANIC DEVICE MATERIAL AND HOLE-INJECTION/TRANSPORT MATERIAL AND ORGANIC ELECTROLUMINESCENT ELEMENT MATERIAL EACH COMPRISING THE DERIVATIVE, AND ORGANIC ELECTROLUMINESCENT ELEMENT

(75) Inventors: Tomoki Kato, Sodegaura (JP); Mitsuru Eida, Sodegaura (JP); Masami Watanabe, Sodegaura (JP); Akinori Yomogita, Sodegaura (JP); Takushi Shiomi, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 976 days.

(21) Appl. No.: 13/496,400

(22) PCT Filed: Feb. 15, 2011

(86) PCT No.: PCT/JP2011/000824
§ 371 (c)(1),
(2), (4) Date: Mar. 15, 2012

(87) PCT Pub. No.: WO2011/102112
PCT Pub. Date: Aug. 25, 2011

(65) Prior Publication Data
US 2012/0187391 A1   Jul. 26, 2012

(30) Foreign Application Priority Data
Feb. 16, 2010   (JP) ................. 2010-031563

(51) Int. Cl.
| | | |
|---|---|---|
| *H01L 51/50* | (2006.01) | |
| *C07D 209/86* | (2006.01) | |
| *C07D 307/91* | (2006.01) | |
| *C07D 407/14* | (2006.01) | |
| *C09K 11/06* | (2006.01) | |
| *H01L 51/00* | (2006.01) | |
| *H05B 33/14* | (2006.01) | |

(52) U.S. Cl.
CPC ........... *C07D 209/86* (2013.01); *C07D 307/91* (2013.01); *C07D 407/14* (2013.01); *C09K 11/06* (2013.01); *H01L 51/0072* (2013.01); *H05B 33/14* (2013.01); *C09K 2211/1029* (2013.01); *H01L 51/5012* (2013.01); *H01L 51/5048* (2013.01)

(58) Field of Classification Search
None
See application file for complete search history.

(56) References Cited

U.S. PATENT DOCUMENTS

| | | |
|---|---|---|
| 2006/0134464 A1 | 6/2006 | Nariyuki |
| 2007/0215889 A1 | 9/2007 | Kawakami et al. |
| 2007/0278938 A1* | 12/2007 | Yabunouchi et al. ........ 313/504 |
| 2009/0066235 A1 | 3/2009 | Yabunouchi et al. |
| 2010/0145067 A1 | 6/2010 | Yokota et al. |

FOREIGN PATENT DOCUMENTS

| | | |
|---|---|---|
| JP | 2005-169781 A | 6/2005 |
| JP | 2006-203172 A | 8/2006 |
| JP | 2007-110093 A | 4/2007 |
| JP | 2007-182401 A | 7/2007 |
| JP | 2007-284431 A | 11/2007 |
| JP | 2008-47935 A | 2/2008 |
| JP | 2008-127290 A | 6/2008 |
| KR | 10-2010-0045587 A | 5/2010 |
| WO | WO 2007/043484 A1 | 4/2007 |
| WO | WO 2007/125714 A1 | 11/2007 |
| WO | WO 2009/020095 A1 | 2/2009 |
| WO | WO 2009/110360 A1 | 9/2009 |

OTHER PUBLICATIONS

International Search Report issued Apr. 26, 2011 in PCT/JP2011/000824.

* cited by examiner

*Primary Examiner* — Gregory Clark
(74) *Attorney, Agent, or Firm* — Oblon, McClelland, Maier & Neustadt, L.L.P.

(57) ABSTRACT

An aromatic amine derivative represented by the following formula (1), wherein L is a linking group, Z is a group represented by the following formula (2) and $A_1$ and $A_2$ are independently a monovalent group represented by the following formula (3):

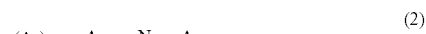

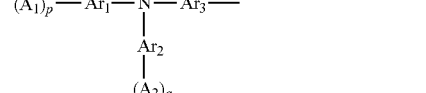

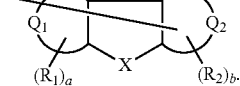

25 Claims, No Drawings

AROMATIC AMINE DERIVATIVE, ORGANIC DEVICE MATERIAL AND HOLE-INJECTION/TRANSPORT MATERIAL AND ORGANIC ELECTROLUMINESCENT ELEMENT MATERIAL EACH COMPRISING THE DERIVATIVE, AND ORGANIC ELECTROLUMINESCENT ELEMENT

TECHNICAL FIELD

The invention relates to an aromatic amine derivative, and an organic device material, a hole-injecting/transporting material and an organic electroluminescence device material each comprising the derivative, as well as an organic electroluminescence device.

BACKGROUND ART

The practical use of displays and lighting devices utilizing an organic electroluminescence device (organic EL device) has recently studied more actively. In particular, reducing cost and growing in size of screen are given as a big issue. Therefore, there is an increasing expectation for transition from traditional vacuum deposition type organic EL devices to (solution) coating type organic EL devices. When organic EL devices are of the coating type, the followings are expected: high material use efficiency, easy film-formation of a large screen and inexpensive apparatus cost due to no vacuum system.

Here, there are low-molecular and high-molecular materials as an organic EL material for a coating type organic device. The high-molecular material is preferable from the view points of solubility, coating uniformity and stacked devices. In particular, development of high-molecular materials for a hole-transporting (injecting) layer which can be used in common for displays and lighting devices is desirable.

Patent Documents 1 to 3 disclose high-molecular materials for a hole-transporting (injecting) layer. However, these materials have various problems such as insufficient hole-transporting function (mobility) and insufficient solubility in coating solvents.

RELATED ART DOCUMENTS

Patent Documents

Patent Document 1: JP-A-2006-203172
Patent Document 2: JP-A-2007-110093
Patent Document 3: JP-A-2008-47935

SUMMARY OF THE INVENTION

An object of the invention is to provide an aromatic amine derivative having high heat resistance, amorphousness and high solubility in a solvent, and having high hole mobility suitable for hole-injecting and -transporting materials.

According to the invention, the following aromatic amine derivative and the like are provided.
1. An aromatic amine derivative represented by the following formula (1):

(1)

wherein Zs are independently a group represented by the following formula (2),
L is an n-valent linking group and may have one or more substituents,
n is an integer of 2 to 10:

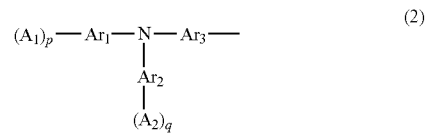
(2)

wherein $Ar_1$ is independently a substituted or unsubstituted (1+p)-valent aromatic hydrocarbon group having 6 to 25 that form a ring (hereinafter referred to as the "ring carbon atoms") or a substituted or unsubstituted (1+p)-valent aromatic heterocyclic group having 5 to 25 atoms that form a ring (hereinafter referred to as the "ring atoms"),
$Ar_2$ is independently a substituted or unsubstituted (1+q)-valent aromatic hydrocarbon group having 6 to 25 ring carbon atoms or a substituted or unsubstituted (1+q)-valent aromatic heterocyclic group having 5 to 25 ring atoms,
$Ar_3$ is independently a single bond, a substituted or unsubstituted divalent aromatic hydrocarbon group having 6 to 25 ring carbon atoms or a substituted or unsubstituted divalent aromatic heterocyclic group having 5 to 25 ring atoms,
$A_1$ and $A_2$ are independently a monovalent group represented by the following formula (3),
p and q are independently an integer of 0 or 1, provided that $p+q \geq 1$:

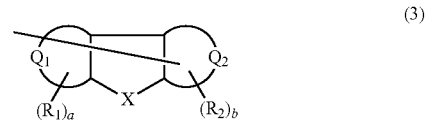
(3)

wherein X is —O—, —S—, —N— or —N($R_a$)—, Ra is a group selected from the group consisting of a hydrogen atom, a linear or branched alkyl group having 1 to 15 carbon atoms, a linear or branched alkenyl group having 2 to 15 carbon atoms, a cycloalkyl group having 3 to 15 carbon atoms, a trialkylsilyl group having an alkyl group having 1 to 15 carbon atoms, a triarylsilyl group having an aryl group having 6 to 25 ring carbon atoms, an alkylarylsilyl group having an alkyl group having 1 to 15 carbon atoms and an aryl group having 6 to 25 ring carbon atoms, an aryl group having 6 to 25 ring carbon atoms and a heteroaryl group having 5 to 25 ring atoms, provided that the "X is —N—" means that X is a nitrogen atom and $Ar_1$ or $A_2$ is bonded to X,
$R_1$ and $R_2$ are independently a group selected from the group consisting of a linear or branched alkyl group having 1 to 15 carbon atoms, a linear or branched alkenyl group having 2 to 15 carbon atoms, a cycloalkyl group having 3 to 15 carbon atoms, a trialkylsilyl group having an alkyl group having 1 to 15 carbon atoms, a triarylsilyl group having an aryl group having 6 to 25 ring carbon atoms, an alkylarylsilyl group having an alkyl group having 1 to 15 carbon atoms and an aryl group having 6 to 25 ring carbon atoms, an aryl group having 6 to 25 ring carbon atoms, a heteroaryl group having 5 to 25 ring atoms, a halogen atom and a cyano group, and adjacent $R_1$s, adjacent $R_2$s and adjacent $R_1$ and $R_2$ may be bonded to each other to form a saturated or unsaturated ring, a and b are independently an integer of 0 to 3, $Q_1$ and $Q_2$ are independently a group having 5 to 25 atoms forming a saturated or unsaturated ring, provided that in the group represented by the formula (2), when $(A_1)_p$-$Ar_1$— is represented by the following formula (4) and q is 1, X of $A_2$ is —O—, —S— or —N($R_a$)—, and in the group represented by the formula (2), when $(A_1)_p$-$Ar_1$— is represented by the following formula (4) and q is 0, $Ar_2$ is a substituted or unsubstituted aromatic hydrocarbon group having 9 to 25 ring carbon atoms which has a polycyclic structure and $Ar_2$ is an asymmetric group relative to the bond axis from $Ar_2$ to the nitrogen atom to which $Ar_2$ is bonded,

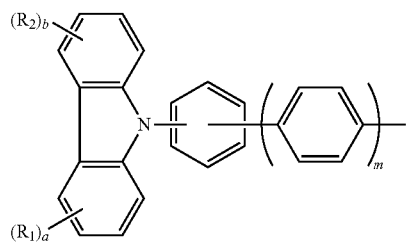

(4)

wherein $R_1$, $R_2$, a and b are the same as those in the formula (3), and m is an integer of 0 to 2, and the hydrogen atom contained in the aromatic amine derivative represented by the above-mentioned formula (1) may include deuterium.

2. The aromatic amine derivative according to 1, wherein $A_1$ and $A_2$ are independently a monovalent group represented by the following formula (5) or (6):

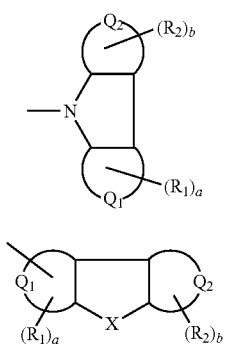

wherein X is —O—, —S— or —N($R_a$)—, and $R_1$, $R_2$, a, b, $Q_1$, $Q_2$ and $R_a$ are the same as those in the formula (3).

3. The aromatic amine derivative according to 2, wherein $A_1$ and $A_2$ are independently a monovalent group represented by the formula (6).

4. The aromatic amine derivative according to 1, wherein $A_1$ and $A_2$ are independently a monovalent group represented by the following formula (7):

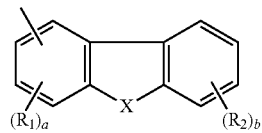

wherein X is —O—, —S— or —N($R_a$)—, and $R_1$, $R_2$, a, b and $R_a$, are the same as those in the formula (3).

5. The aromatic amine derivative according to 1, wherein $A_1$ and $A_2$ are independently a monovalent group represented by the following formula (8-1) or (8-2):

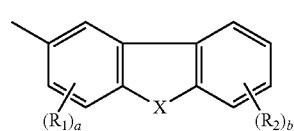

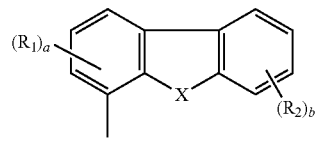

wherein X is —O—, —S— or —N($R_a$)—, and $R_1$, $R_2$, a, b and $R_a$, are the same as those in the formula (3).

6. The aromatic amine derivative according to any of 1 to 5, wherein at least one of $Ar_1$ and $Ar_2$ is a linking group selected from a phenylene group, a biphenylene group, a terphenylene group, a naphthylene group and a phenanthrenylene group.

7. The aromatic amine derivative according to any of 1 to 5, wherein at least one of $Ar_1$ and $Ar_2$ is a divalent group represented by the following formula (9):

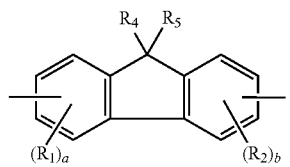

wherein $R_4$ and $R_5$ are independently a group selected from the group consisting of a hydrogen atom, a linear or branched alkyl group having 1 to 15 carbon atoms, a linear or branched alkenyl group having 2 to 15 carbon atoms, a cycloalkyl group having 3 to 15 carbon atoms, a trialkylsilyl group having an alkyl group having 1 to 15 carbon atoms, a triarylsilyl group having an aryl group having 6 to 25 ring carbon atoms, an alkylarylsilyl group having an alkyl group having 1 to 15 carbon atoms and an aryl group having 6 to 25 ring carbon atoms, an aryl group having 6 to 25 ring carbon atoms and a heteroaryl group having 5 to 25 ring atoms, and $R_4$ and $R_5$ may be bonded to each other to form a saturated or unsaturated ring, and $R_1$, $R_2$, a and b are the same as those in the formula (3).

8. The aromatic amine derivative according to any of 1 to 7, wherein in the formula (2), at least one Z has different $(A_1)_p$-$Ar_1$— and $(A_2)_q$-$Ar_2$—.

9. The aromatic amine derivative according to any of 1 to 8, wherein $Ar_a$ is independently a divalent group represented by the following formula (10):

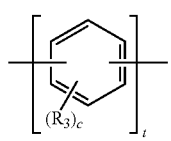
(10)

wherein $R_3$ is independently a group selected from the group consisting of a linear or branched alkyl group having 1 to 15 carbon atoms, a linear or branched alkenyl group having 2 to 15 carbon atoms, a cycloalkyl group having 3 to 15 carbon atoms, a trialkylsilyl group having an alkyl group having 1 to 15 carbon atoms, a triarylsilyl group having an aryl group having 6 to 25 ring carbon atoms, an alkylarylsilyl group having an alkyl group having 1 to 15 carbon atoms and an aryl group having 6 to 25 ring carbon atoms, an aryl group having 6 to 25 ring carbon atoms, a heteroaryl group having 5 to 25 ring atoms, a halogen atom and a cyano group, $R_3$ may be bonded to each other to form a saturated or unsaturated ring, c is an integer of 0 to 4 and t is an integer of 1 to 3.

10. The aromatic amine derivative according to any of 1 to 9, wherein Zs differ from each other.

11. The aromatic amine derivative according to any of 1 to 10, wherein L is a linking group comprising one of the following groups:

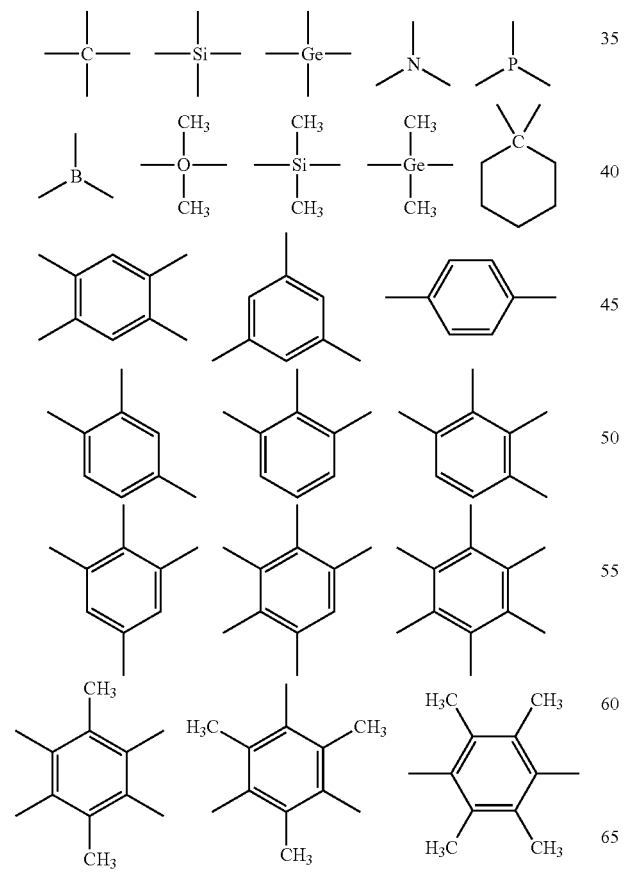

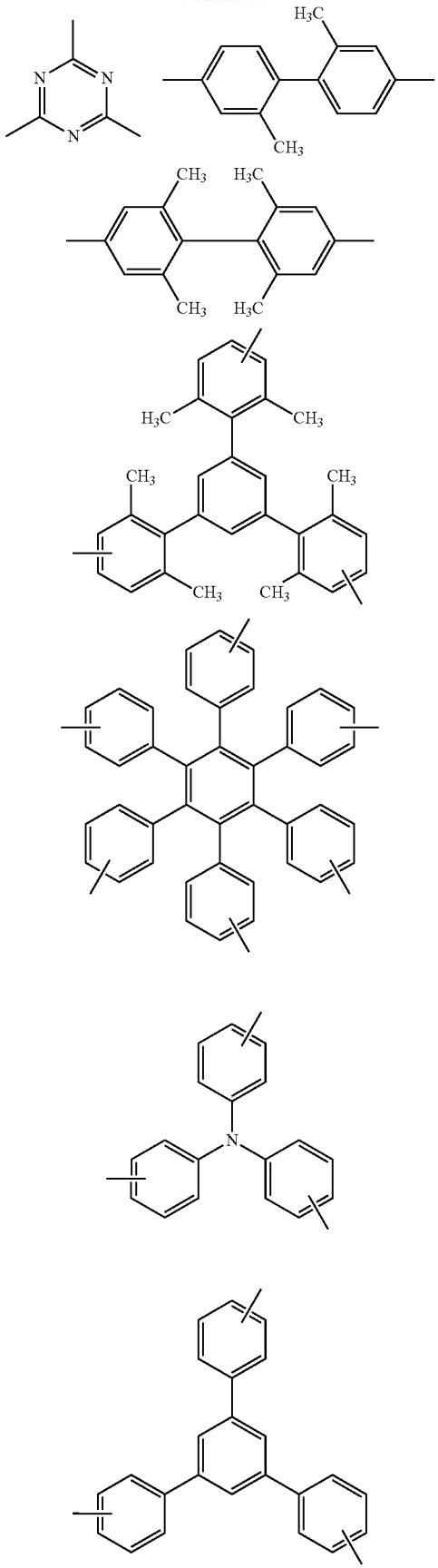

-continued

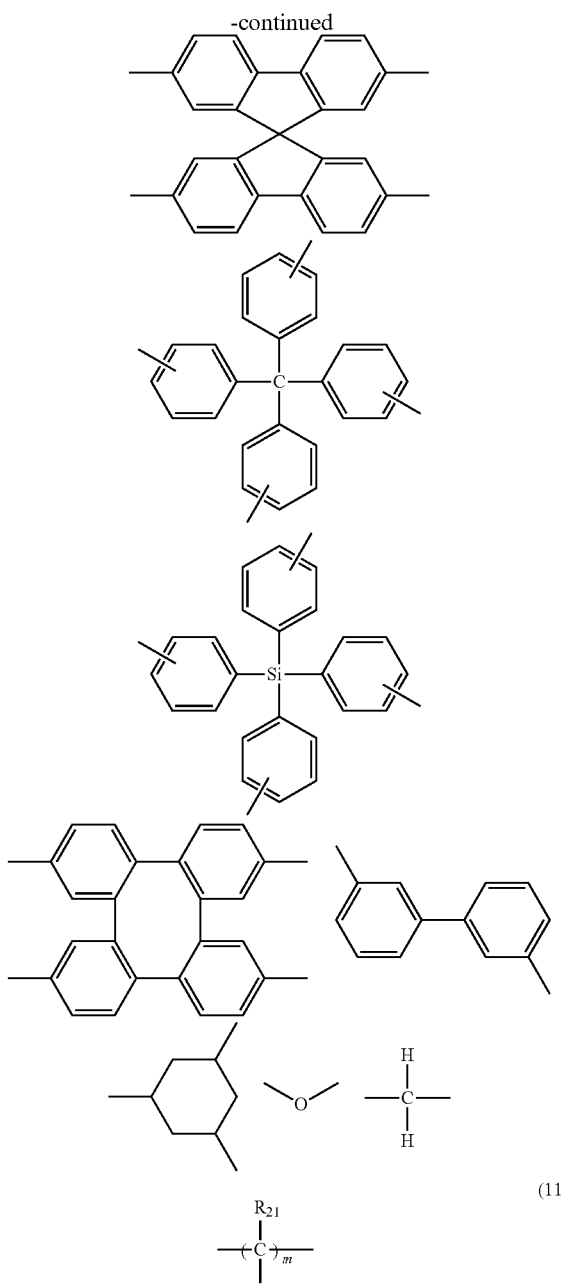

wherein in the formula (11), $R_{21}$ and $R_{22}$ are independently a hydrogen atom, a methyl group, an ethyl group, a propyl group, an isopropyl group, a butyl group, an isobutyl group or a t-butyl group, and m is an integer of 2 to 20;

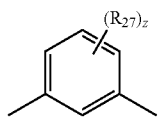

wherein in the formula (12), $R_{23}$, $R_{24}$, $R_{25}$ and $R_{26}$ are independently a hydrogen atom, a linear or branched alkyl group having 1 to 20 carbon atoms, a linear or branched alkenyl group having 2 to 20 carbon atoms, a cycloalkyl group having 3 to 20 carbon atoms, a trialkylsilyl group having an alkyl group having 1 to 20 carbon atoms, a triarylsilyl group having an aryl group having 6 to 24 ring carbon atoms, an alkylarylsilyl group having an alkyl group having 1 to 20 carbon atoms and an aryl group having 6 to 24 ring carbon atoms, an aryl group having 6 to 24 ring carbon atoms or a heteroaryl group having 5 to 24 ring atoms, $R_{23}$ and $R_{24}$, $R_{25}$s or $R_{26}$s may be bonded to each other to form a saturated or unsaturated ring, x is an integer of 1 to 3 and y is an integer of 1 to 3, provided that when x is an integer of 2 or more, $R_{25}$s independently may be the same or different, and when y is an integer of 2 or more, $R_{26}$s independently may be the same or different;

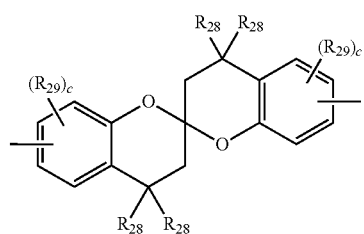

wherein in the formula (13), $R_{27}$ is a hydrogen atom, a linear or branched alkyl group having 1 to 20 carbon atoms, a linear or branched alkenyl group having 2 to 20 carbon atoms, a cycloalkyl group having 3 to 20 carbon atoms, a trialkylsilyl group having an alkyl group having 1 to 20 carbon atoms, a triarylsilyl group having an aryl group having 6 to 24 ring carbon atoms, an alkylarylsilyl group having an alkyl group having 1 to 20 carbon atoms and an aryl group having 6 to 24 ring carbon atoms, an aryl group having 6 to 24 ring carbon atoms or a heteroaryl group having 5 to 24 ring atoms, and z is an integer of 1 to 4, provided that when z is an integer of 2 or more, $R_{27}$s may independently be the same or different;

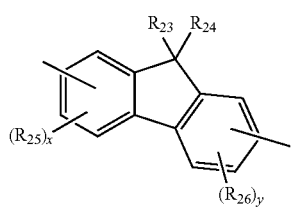

wherein in the formula (14), $R_{28}$ and $R_{29}$ are independently a hydrogen atom, a linear or branched alkyl group having 1 to 20 carbon atoms, a linear or branched alkenyl group having 2 to 20 carbon atoms, a cycloalkyl group having 3 to 20 carbon atoms, a trialkylsilyl group having an alkyl group having 1 to 20 carbon atoms, a triarylsilyl group having an aryl group having 6 to 24 ring carbon atoms, an alkylarylsilyl group having an alkyl group having 1 to 20 carbon atoms and an aryl group having 6 to 24 ring carbon atoms, an aryl group having 6 to 24 ring carbon atoms or a heteroaryl group having 5 to 24 ring atoms, and c is an integer of 1 to 3, provided that when c is an integer of 2 or more, $R_{29}$s may independently be the same or different, and $R_{28}$ or $R_{29}$ may be bonded to each other to form a saturated or unsaturated ring.

12. The aromatic amine derivative according to 11, wherein L is a linking group comprising one of the following groups:

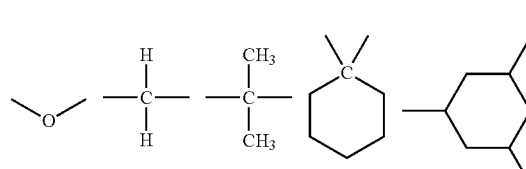
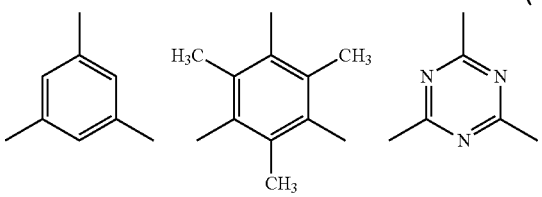
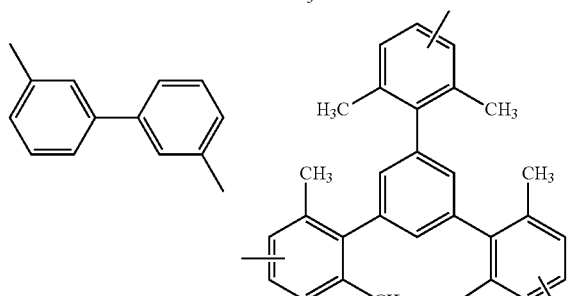
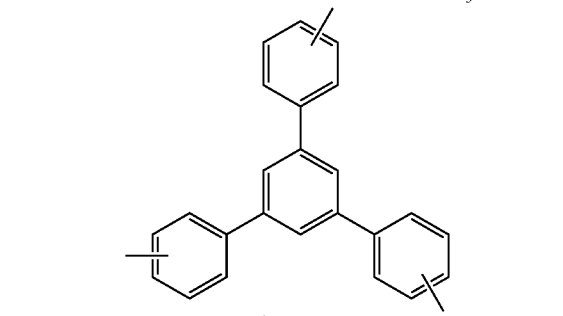
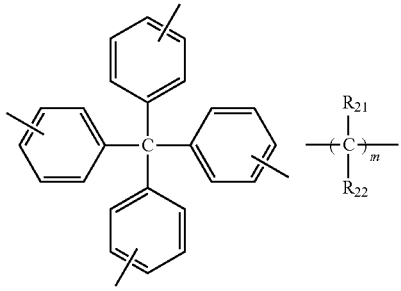

(11)

wherein the formula (11) is the same as the above-mentioned formula (11);

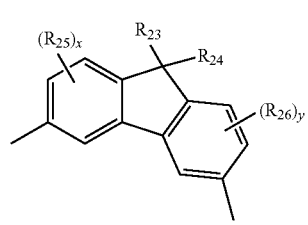

(12-1)

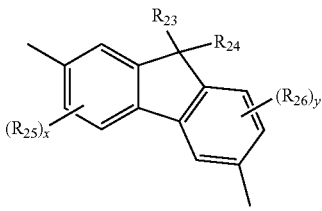

(12-2)

wherein in the formulas (12-1) and (12-2), $R_{23}$, $R_{24}$, $R_{25}$, $R_{26}$, x and y are the same as those in the formula (12);

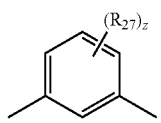

(13)

wherein the formula (13) is the same as the above-mentioned formula (13);

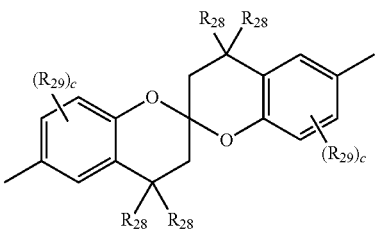

(14)

wherein the formula (14) is the same as the above-mentioned formula (14).

13. An organic device material comprising the aromatic amine derivative according to any of 1 to 12.

14. A hole-injecting and -transporting material comprising the aromatic amine derivative according to any of 1 to 12.

15. An organic electroluminescence device material comprising the aromatic amine derivative according to any of 1 to 12.

16. An organic electroluminescence device comprising:
an anode, a cathode and one or more organic thin film layers comprising at least an emitting layer therebetween,
wherein at least one of the organic thin film layers comprises the aromatic amine derivative according to any of 1 to 12.

17. The organic electroluminescence device according to 16, wherein the organic thin film layers comprise at least one of a hole-transporting layer and a hole-injecting layer, and the at least one of a hole-transporting layer and a hole-injecting layer comprises the aromatic amine derivative.

18. The organic electroluminescence device according to 17, wherein the at least one of a hole-transporting layer and a hole-injecting layer comprises the aromatic amine derivative as a main component.

19. The organic electroluminescence device according to any of 16 to 18, wherein the organic thin film layers comprise at least one of a hole-transporting layer and a hole-injecting layer, and the at least one of a hole-transporting layer and a hole-injecting layer comprises an acceptor material.

According to the invention, it is possible to provide an aromatic amine derivative having high heat resistance, amorphousness and high solubility in a solvent, and having high hole mobility suitable for hole-injecting and -transporting materials.

MODE FOR CARRYING OUT THE INVENTION

The aromatic amine derivative of the invention is represented by the following formula (1). Meanwhile, in the specification, the hydrogen atom may include a deuterium atom.

  (1)

wherein Zs are independently a group represented by the following formula (2).

L is an n-valent linking group. L is preferably a linking group selected from the group consisting of a tetravalent carbon atom, a tetravalent silicon atom, a trivalent nitrogen atom, a tetravalent germanium atom, a trivalent phosphorus atom, a trivalent boron atom, a divalent oxygen atom, a divalent group formed by combination of one or more alkylenes and one or more —O-s, an n-valent alkane residue having 1 to 20 carbon atoms, an n-valent cycloalkane residue having 3 to 20 ring carbon atoms, an n-valent trialkylamine residue having an alkyl group having 1 to 20 carbon atoms, an n-valent triarylamine residue having an aryl group having 6 to 24 carbon atoms, an n-valent alkylarylamine residue having an alkyl group having 1 to 20 carbon atoms and an aryl group having 6 to 24 carbon atoms, an n-valent aromatic hydrocarbon group having 6 to 24 ring carbon atoms and an n-valent aromatic heterocyclic group having 3 to 24 ring atoms, or a linking group comprising these.

Here, it suffices that the linking group L comprise the above-mentioned groups (including atoms), and may be used singly, in combination of the same groups being bonded repeatedly or in combination of different groups.

L may further have one or more substituents, and the substituents are independently a linear or branched alkyl group having 1 to 15 carbon atoms, a linear or branched alkenyl group having 2 to 15 carbon atoms, a cycloalkyl group having 3 to 15 carbon atoms, a trialkylsilyl group having an alkyl group having 1 to 15 carbon atoms, a triarylsilyl group having an aryl group having 6 to 25 ring carbon atoms, an alkylarylsilyl group having an alkyl group having 1 to 15 carbon atoms and an aryl group having 6 to 25 ring carbon atoms, an aryl group having 6 to 25 ring carbon atoms, a heteroaryl group having 5 to 25 ring atoms, a halogen atom or a cyano group.

n is an integer of 2 to 10, preferably 2, 3 or 4.

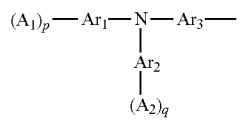  (2)

wherein $Ar_1$ is independently a substituted or unsubstituted (1+p)-valent aromatic hydrocarbon group having 6 to 25 ring carbon atoms or a substituted or unsubstituted (1+p)-valent aromatic heterocyclic group having 5 to 25 ring atoms, $Ar_2$ is independently a substituted or unsubstituted (1+q)-valent aromatic hydrocarbon group having 6 to 25 ring carbon atoms or a substituted or unsubstituted (1+q)-valent aromatic heterocyclic group having 5 to 25 ring atoms, $Ar_3$ is independently a single bond, a substituted or unsubstituted divalent aromatic hydrocarbon group having 6 to 25 ring carbon atoms or a substituted or unsubstituted divalent aromatic heterocyclic group having 5 to 25 ring atoms, the substituents of $Ar_1$, $Ar_2$ and $Ar_3$ are the same as those of L, $A_1$ and $A_2$ are independently a monovalent group represented by the following formula (3), and p and q are independently an integer of 0 or 1, provided that p+q≥1.

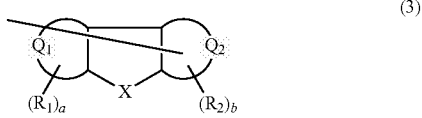  (3)

wherein X is an oxygen atom (—O—), a sulfur atom (—S—), a nitrogen atom (—N—) or —N($R_a$)—, and $R_a$ is a group selected from the group consisting of a hydrogen atom, a linear or branched alkyl group having 1 to 15 carbon atoms, a linear or branched alkenyl group having 2 to 15 carbon atoms, a cycloalkyl group having 3 to 15 carbon atoms, a trialkylsilyl group having an alkyl group having 1 to 15 carbon atoms, a triarylsilyl group having an aryl group having 6 to 25 ring carbon atoms, an alkylarylsilyl group having an alkyl group having 1 to 15 carbon atoms and an aryl group having 6 to 25 ring carbon atoms, an aryl group having 6 to 25 ring carbon atoms and a heteroaryl group having 5 to 25 ring atoms. Here "X is —N—" means that X is a nitrogen atom and $Ar_1$ or $Ar_2$ is bonded to X.

$R_1$ and $R_2$ are independently a group selected from the group consisting of a linear or branched alkyl group having 1 to 15 carbon atoms, a linear or branched alkenyl group having 2 to 15 carbon atoms, a cycloalkyl group having 3 to 15 carbon atoms, a trialkylsilyl group having an alkyl group having 1 to 15 carbon atoms, a triarylsilyl group having an aryl group having 6 to 25 ring carbon atoms, an alkylarylsilyl group having an alkyl group having 1 to 15 carbon atoms and an aryl group having 6 to 25 ring carbon atoms, an aryl group having 6 to 25 ring carbon atoms, a heteroaryl group having 5 to 25 ring atoms, a halogen atom and a cyano group, and adjacent $R_1$s, adjacent $R_2$s and adjacent $R_1$ and $R_2$ may be bonded to each other to form a saturated or unsaturated ring.

a and b are independently an integer of 0 to 3.

$Q_1$ and $Q_2$ are independently a group having 5 to 25 atoms forming a saturated or unsaturated ring.

Meanwhile, in the group represented by the formula (2), when $(A_1)_p$-$Ar_1$— is represented by the following formula (4) and q is 1, X of $A_2$ is —O—, —S— or —N($R_a$)—, and in the group represented by the formula (2), when $(A_1)_p$-$Ar_1$— is represented by the following formula (4) and q is 0, $Ar_2$ is a substituted or unsubstituted aromatic hydrocarbon group having 9 to 25 ring carbon atoms which has a polycyclic structure and $Ar_2$ is an asymmetric group relative to the bond axis from $Ar_2$ to the nitrogen atom to which $Ar_2$ is bonded,

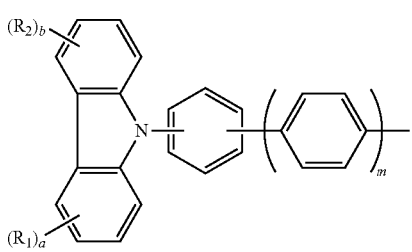

(4)

wherein $R_1$, $R_2$, a and b are the same as those in the formula (3), and m is an integer of 0 to 2.

The above-mentioned "an asymmetric group relative to the bond axis from $Ar_2$ to the nitrogen atom to which $Ar_2$ is bonded" means an asymmetric group relative to the bond axis from $Ar_2$ to the nitrogen atom shown below:

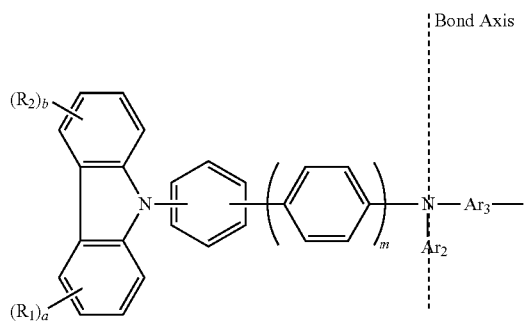

When X is —N($R_a$)—, the group wherein $Ar_1$ and $Ar_2$ are bonded to X is not included.

The aromatic amine unit (Z) of the aromatic amine derivative of the invention has excellent functions as a hole-injecting and -transporting layer material for an organic device, in particular an organic EL device. Specifically, the aromatic amine unit (Z) has a wide band gap which blocks electrons and allows holes and electrons to recombine in the emitting layer efficiently, an ionization potential suitable for injecting holes into the emitting layer, a high hole mobility leading to a reduction in voltage, and the like.

Furthermore, the aromatic amine derivative of the invention has a plurality of aromatic amine units (Z) in one molecule through the linking group L, thereby resulting in high heat-resistance, amorphousness and high solubility in a solvent.

Meanwhile, if the aromatic amine derivative is crystalline, an organic EL device may tend to suffer short circuit particularly between the electrodes thereof and adverse effects may be exerted on heat-resistance thereof.

In the aromatic amine derivative of the invention, $A_1$ and $A_2$ in the formula (2) are preferably independently a monovalent group represented by the following formula (5) or (6), and more preferably independently a monovalent group represented by the following formula (6).

By allowing $A_1$ and $A_2$ to be a monovalent group represented by the formula (5) or (6), the aromatic amine derivative can have improved electron resistance and hole mobility, as well as improved solubility in a solvent and enhanced amorphousness due to the asymmetric structure.

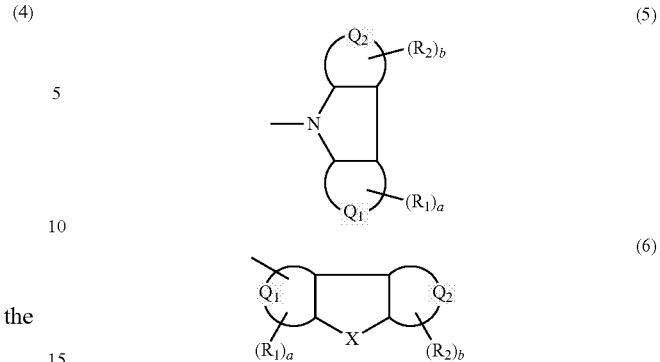

wherein X is —O—, —S— or —N($R_a$)—, and $R_1$, $R_2$, a, b, $Q_1$, $Q_2$ and $R_a$, are the same as those in the formula (3).

$A_1$ and $A_2$ in the formula (2) are preferably independently a monovalent group represented by the following formula (7):

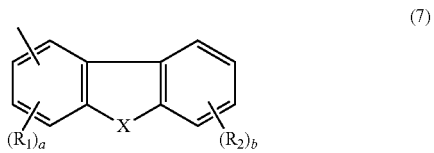

wherein X is —O—, —S— or —N($R_a$)—, and $R_1$, $R_2$, a, b and $R_a$, are the same as those in the formula (3).

$A_1$ and $A_2$ in the formula (2) are preferably independently a monovalent group represented by the following formula (8-1) or (8-2).

By allowing $A_1$ and $A_2$ to be a monovalent group represented by the formula (8-1) or (8-2), the aromatic amine derivative can be synthesized and purified easily, whereby purity can be improved and a device such an organic EL device obtained can have a longer lifetime.

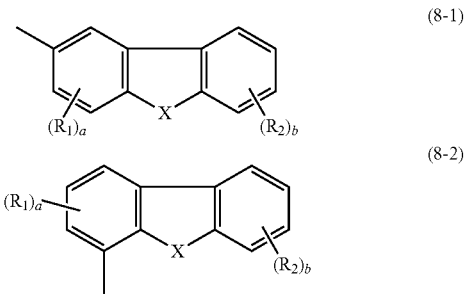

wherein X is —O—, —S— or —N($R_a$)—, and $R_1$, $R_2$, a, b and $R_a$, are the same as those in the formula (3).

In the formula (2), it is preferred that at least one of $A_1$ and $A_2$ is a linking group selected from a phenylene group, a biphenylene group, a terphenylene group, a naphthylene group and a phenanthrenylene group.

By allowing at least one of $A_1$ and $A_2$ to be the above-mentioned linking group, devices obtained such as an organic EL device can have improved heat resistance and improved hole-injecting property into the emitting layer.

In the formula (2), at least one of $Ar_1$ and $Ar_2$ is a divalent group represented by the following formula (9).

By allowing at least one of $Ar_1$ and $Ar_2$ to be a divalent group represented by the formula (9), the aromatic amine derivative can have higher hole mobility, and can have improved solubility in a solvent and enhanced amorphousness due to the asymmetric structure.

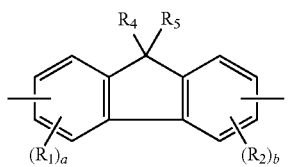

(9)

wherein $R_4$ and $R_5$ are independently a group selected from the group consisting of a hydrogen atom, a linear or branched alkyl group having 1 to 15 carbon atoms, a linear or branched alkenyl group having 2 to 15 carbon atoms, a cycloalkyl group having 3 to 15 carbon atoms, a trialkylsilyl group having an alkyl group having 1 to 15 carbon atoms, a triarylsilyl group having an aryl group having 6 to 25 ring carbon atoms, an alkylarylsilyl group having an alkyl group having 1 to 15 carbon atoms and an aryl group having 6 to 25 ring carbon atoms, an aryl group having 6 to 25 ring carbon atoms and a heteroaryl group having 5 to 25 ring atoms, and $R_4$ and $R_5$ may be bonded to each other to form a saturated or unsaturated ring.

$R_1$, $R_2$, a and b are the same as those in the formula (3).

In the aromatic amine derivative of the invention, one or more Z has preferably different $(A_1)_p$-$Ar_1$— and $(A_2)_q$-$Ar_2$— in the formula (2).

By containing Z which has different $(A_1)_p$-$Ar_1$— and $(A_2)_q$-$Ar_2$—, the aromatic amine derivative can have enhanced amorphousness and have improved solubility in a solvent.

In the aromatic amine derivative of the invention, $Ar_3$ in the formula (2) is preferably a divalent group represented by the following formula (10).

By allowing $Ar_3$ to be a divalent group represented by the following formula (10), the aromatic amine derivative can have improved heat resistance. In addition, the aromatic amine derivative allows a device obtained such as an organic EL device to have improved hole-injecting property into the emitting layer thereof.

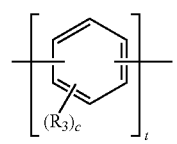

(10)

wherein $R_3$ is independently a group selected from the group consisting of a linear or branched alkyl group having 1 to 15 carbon atoms, a linear or branched alkenyl group having 2 to 15 carbon atoms, a cycloalkyl group having 3 to 15 carbon atoms, a trialkylsilyl group having an alkyl group having 1 to 15 carbon atoms, a triarylsilyl group having an aryl group having 6 to 25 ring carbon atoms, an alkylarylsilyl group having an alkyl group having 1 to 15 carbon atoms and an aryl group having 6 to 25 ring carbon atoms, a heteroaryl group having 5 to 25 ring atoms, a halogen atom and a cyano group.

$R_3$s, preferably adjacent $R_3$s, may be bonded to each other to form a saturated or unsaturated divalent group forming a ring, c is an integer of 0 to 4 and t is an integer of 1 to 3.

The aromatic amine unit Z was explained hereinbefore. In the aromatic amine derivative of the invention, Zs in the formula (1) preferably differ from each other.

The aromatic amine derivative wherein Zs differ from each other can be more amorphous and have a improved solubility in a solvent.

In the formula (1), the linking group L is a group represented by one of the following groups or a group comprising the following groups.

Here, the linking group L only has to comprise the following groups, and may be used singly, in combination of the same groups being bonded repeatedly or in combination of different groups.

These linking groups allow the aromatic amine units to be bonded, thereby increasing the amorphous property and the solubility in a solvent of the aromatic amine derivative to facilitate the uniform coating film formation of a large screen.

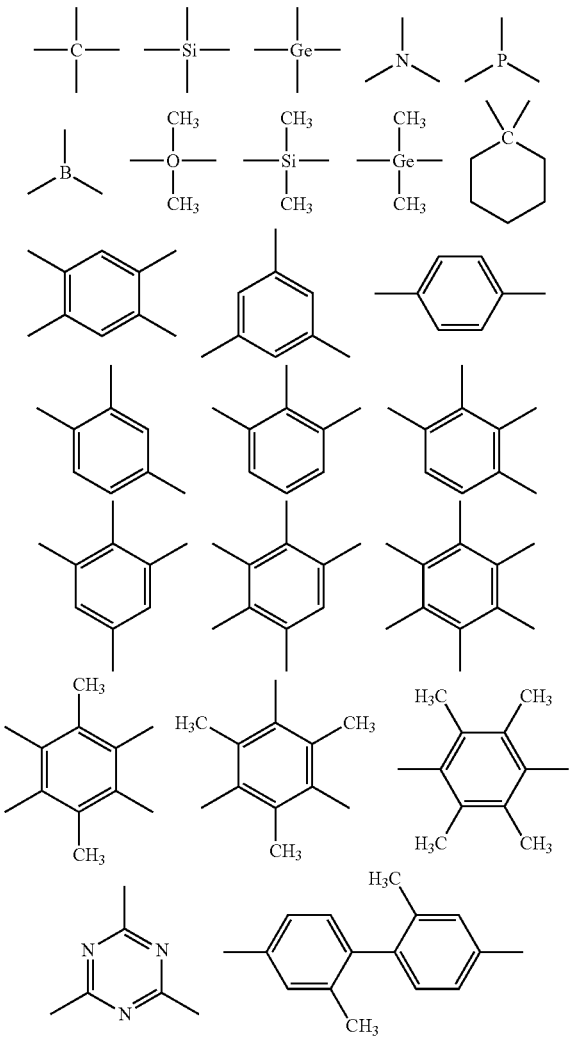

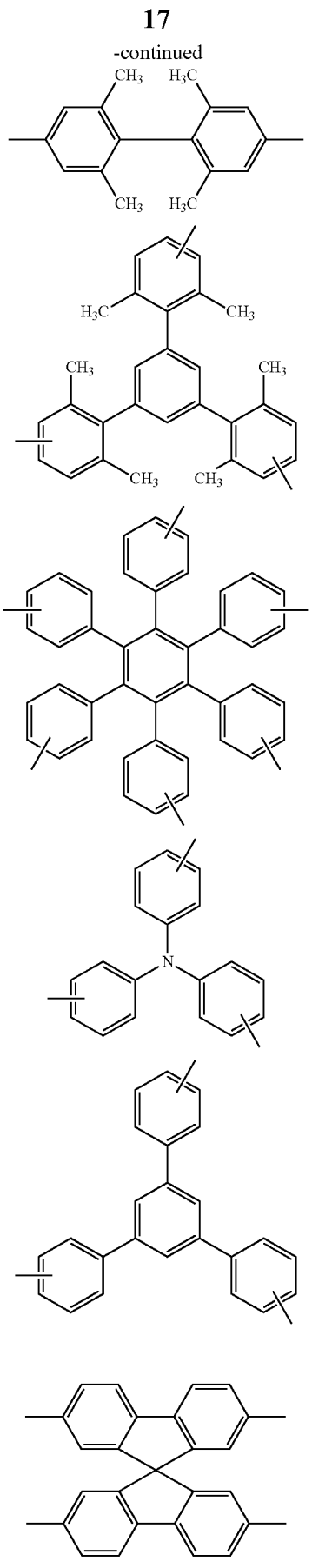
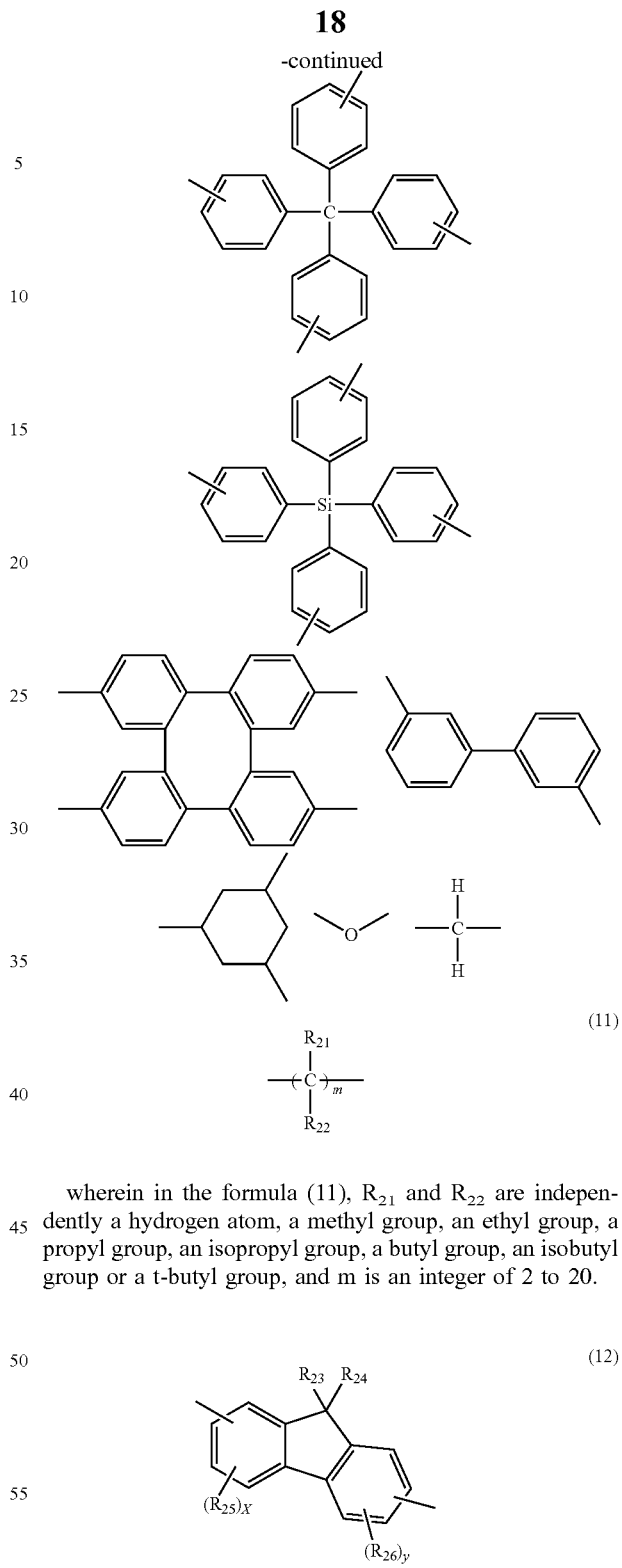

wherein in the formula (11), $R_{21}$ and $R_{22}$ are independently a hydrogen atom, a methyl group, an ethyl group, a propyl group, an isopropyl group, a butyl group, an isobutyl group or a t-butyl group, and m is an integer of 2 to 20.

wherein in the formula (12), $R_{23}$, $R_{24}$, $R_{25}$ and $R_{26}$ are independently a hydrogen atom, a linear or branched alkyl group having 0.1 to 20 carbon atoms, a linear or branched alkenyl group having 2 to 20 carbon atoms, a cycloalkyl group having 3 to 20 carbon atoms, a trialkylsilyl group having an alkyl group having 1 to 20 carbon atoms, a triarylsilyl group having an aryl group having 6 to 24 ring carbon atoms, an alkylarylsilyl group having an alkyl group having 1 to 20 carbon atoms and an aryl group having 6 to 24 ring carbon atoms, an aryl group having 6 to 24 ring carbon atoms or a heteroaryl group having 5 to 24 ring atoms, $R_{23}$ and $R_{24}$, $R_{25}$ or $R_{26}$ may be bonded to each other to form a saturated or unsaturated ring, x is an integer of 1 to 3 and y is an integer of 1 to 3, provided that when x is an integer of 2 or more, $R_{25}$s independently may be the same or different, and when y is an integer of 2 or more, $R_{26}$s independently may be the same or different.

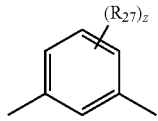

wherein in the formula (13), $R_{27}$ is a hydrogen atom, a linear or branched alkyl group having 1 to 20 carbon atoms, a linear or branched alkenyl group having 2 to 20 carbon atoms, a cycloalkyl group having 3 to 20 carbon atoms, a trialkylsilyl group having an alkyl group having 1 to 20 carbon atoms, a triarylsilyl group having an aryl group having 6 to 24 ring carbon atoms, an alkylarylsilyl group having an alkyl group having 1 to 20 carbon atoms and an aryl group having 6 to 24 ring carbon atoms, an aryl group having 6 to 24 ring carbon atoms or a heteroaryl group having 5 to 24 ring atoms, z is an integer of 1 to 4, provided that when z is an integer of 2 or more, $R_{27}$s may independently be the same or different.

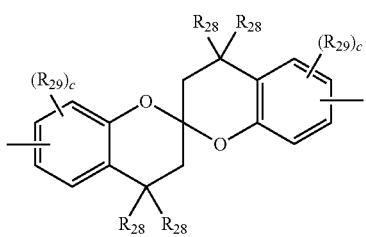

wherein in the formula (14), $R_{28}$ and $R_{29}$ are independently a hydrogen atom, a linear or branched alkyl group having 1 to 20 carbon atoms, a linear or branched alkenyl group having 2 to 20 carbon atoms, a cycloalkyl group having 3 to 20 carbon atoms, a trialkylsilyl group having an alkyl group having 1 to 20 carbon atoms, a triarylsilyl group having an aryl group having 6 to 24 ring carbon atoms, an alkylarylsilyl group having an alkyl group having 1 to 20 carbon atoms and an aryl group having 6 to 24 ring carbon atoms, an aryl group having 6 to 24 ring carbon atoms or a heteroaryl group having 5 to 24 ring atoms, and c is an integer of 1 to 3, provided that when c is an integer of 2 or more, $R_{29}$s may independently be the same or different, and $R_{28}$ or $R_{29}$ may be bonded to each other to form a saturated or unsaturated ring.

Of the above-mentioned linking groups, the following groups or a group comprising the following groups are more preferable.

Here, it suffices that the linking group L comprise the following groups, and may be used singly, in combination of the same groups being bonded repeatedly or in combination of different groups.

These linking groups can further block conjugation between Zs to allow the aromatic amine derivative to block electrons. As a result, the derivative can have a wide band gap which allows holes and electrons to recombine efficiently in the emitting layer and an ionization potential suitable for injecting holes into the emitting layer.

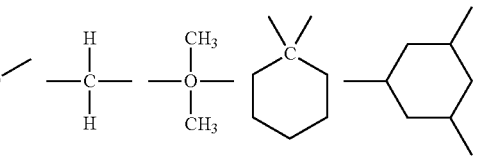

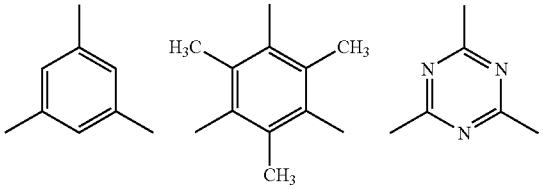

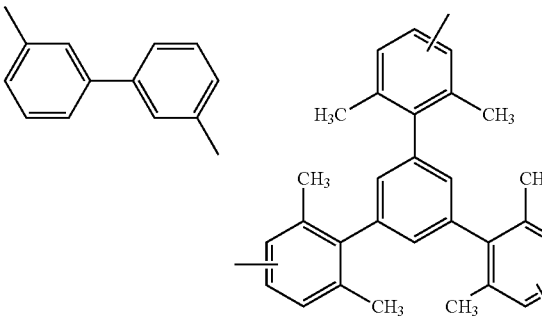

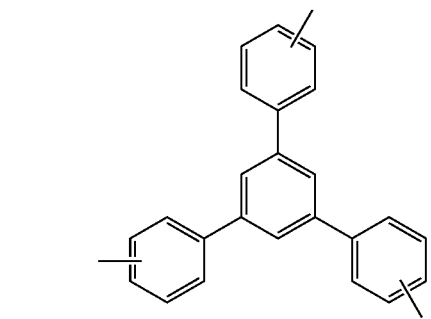

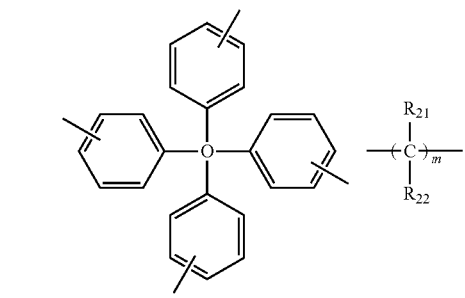

wherein the formula (11) is the same as the above-mentioned formula (11);

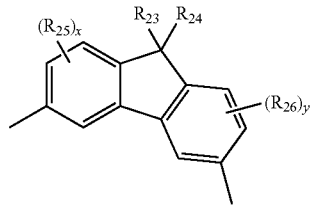
(12-1)

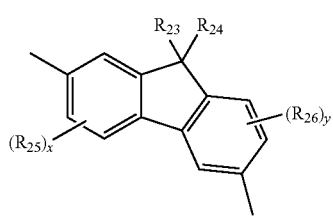
(12-2)

wherein in the formulas (12-1) and (12-2), $R_{23}$, $R_{24}$, $R_{25}$, $R_{26}$, x and y are the same as those in the formula (12);

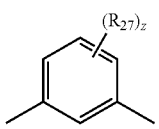
(13)

wherein the formula (13) is the same as the above-mentioned formula (13);

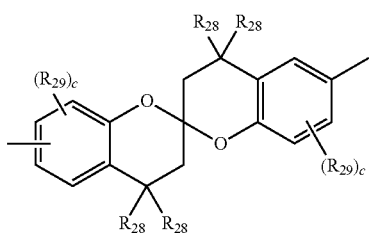
(14)

wherein the formula (14) is the same as the above-mentioned formula (14).

As the linking group L comprising an oxygen atom, preferably, an aromatic heterocyclic group comprising an oxygen atom, and a group composed of one or more alkylene groups and one or more —O-s can be given. As the aromatic heterocyclic group comprising an oxygen atom, the group represented by the above-mentioned formula (14) can be given, for example. Examples of the group composed of alkylene groups and —O-s include an alkylene represented by —R—(—O—R')x— wherein R is an alkylene group having 1 to 4 carbon atoms (preferably 1 or 2 carbon atoms), R' is an alkylene group having 1 to 4 carbon atoms (preferably 1 or 2 carbon atoms) which may be the same as or different from R and x is an integer of 1 to 10 (preferably an integer of 1 to 5).

Preferable examples of L include a substituted or unsubstituted benzene ring residue, a substituted or unsubstituted fluorene ring residue, a group represented by the above-mentioned formula (14), an alkane residue having 1 to 20 carbon atoms and a group represented by the —R—(—O—R')x—. As a preferable substituent, an alkyl group having 1 to 15 carbon atoms (preferably 1 to 10 carbon atoms) and the like can be given.

Specific examples of each substituent of the formulas (1) to (10) will be explained below.

Examples of the aryl group include a phenyl group, a 1-naphthyl group, a 2-naphythyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a biphenyl-2-yl group, a biphenyl-3-yl group, a biphenyl-4-yl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenyl-4-yl group, a 4''-t-butyl-p-terphenyl-4-yl group, a fluorene-1-yl group, a fluorene-2-yl group, a fluorene-3-yl group and a fluorine-4-yl group.

Among these, a phenyl group, a 1-naphthyl group, a 2-naphythyl group, a 1-anthryl group, a 2-anthryl group, a 9-anthryl group, a biphenyl-2-yl group, a biphenyl-3-yl group, a biphenyl-4-yl group, a p-terphenyl-4-yl group, a p-terphenyl-3-yl group, a p-terphenyl-2-yl group, an o-tolyl group, an m-tolyl group, a p-tolyl group, a fluorene-2-yl group and a fluorene-3-yl group are preferable. A phenyl group, a 1-naphthyl group, a 2-naphthyl group, an m-tolyl group, a p-tolyl group, a fluorene-2-yl group and a fluorene-3-yl group are more preferable.

Examples of the alkyl group include a methyl group, an ethyl group, a propyl group, an isopropyl group, an n-butyl group, an isobutyl group, a sec-butyl group, a tert-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group and a 1,2,3-trihydroxypropyl group. Preferable are a methyl group, an ethyl group, a propyl group, an isopropyl group, an n-butyl group, an isobutyl group, a sec-butyl group and a tert-butyl group. More preferable are a methyl group, an ethyl group, a propyl group, an isopropyl group, an n-butyl group, an s-butyl group and a t-butyl group.

As the alkenyl group, a substituent having an unsaturated bond in the molecule of the above-mentioned alkyl groups can be given.

As the cycloalkyl group, a cyclopropyl group, a cyclobutyl group, a cyclopentyl group, a cyclohexyl group, a cyclopentylmethyl group, a cyclohexylmethyl group, a cyclohexylethyl group, a 4-fluorocyclohexyl group, a 1-adamantyl group, a 2-adamantyl group, a 1-norbornyl group, a 2-norbornyl group and the like can be given. A cyclopentyl group and a cyclohexyl group are preferable.

As the trialkylsilyl group, a trimethylsilyl group, a vinyldimethylsilyl group, a triethylsilyl group, a tripropylsilyl group, a propyldimethylsilyl group, a tributylsilyl group, a t-butyldimethylsilyl group, a tripenthylsilyl group, a triheptylsilyl group, a trihexylsilyl group and the like can be given. A trimethylsilyl group and a triethylsilyl group are preferable.

The alkyl groups substituting the silyl group may be the same or different.

As the triarylsilyl group, a triphenylsilyl group, a trinaphthylsilyl group and the like can be given. Preferable is a triphenylsilyl group.

The aryl groups substituting the silyl group may be the same or different.

As the alkylarylsilyl group, a dimethylphenylsilyl group, a diethylphenylsilyl group, a diphenylmethylsilyl group, an ethyldiphenylsilyl group and the like can be given. Preferable are a diphenylmethylsilyl group and an ethyldiphenylsilyl group.

The alkyl groups and the aryl groups substituting the silyl group may be the same or different.

As the heteroaryl group, a 1-pyrrolyl group, a 2-pyrrolyl group, a 3-pyrrolyl group, a pyradinyl group, a 2-pyrydinyl group, a 3-pyrydinyl group, a 4-pyrydinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 2-quinoxalynyl group, a 5-quinoxalynyl group, a 6-quinoxalynyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, a 8-phenanthridinyl group, a 9-phenanthridinyl group, a 10-phenanthridinyl group, a 1-acrydinyl group, a 2-acrydinyl group, a 3-acrydinyl group, a 4-acrydinyl group, a 9-acrydinyl group, a 1,7-phenanthroline-2-yl group, a 1,7-phenanthroline-3-yl group, a 1,7-phenanthroline-4-yl group, a 1,7-phenanthroline-5-yl group, a 1,7-phenanthroline-6-yl group, a 1,7-phenanthroline-8-yl group, a 1,7-phenanthroline-9-yl group, a 1,7-phenanthroline-10-yl group, a 1,8-phenanthroline-2-yl group, a 1,8-phenanthroline-3-yl group, a 1,8-phenanthroline-4-yl group, a 1,8-phenanthroline-5-yl group, a 1,8-phenanthroline-6-yl group, a 1,8-phenanthro-line-7-yl group, a 1,8-phenanthroline-9-yl group, a 1,8-phenanthroline-10-yl group, a 1,9-phenanthroline-2-yl group, a 1,9-phenanthroline-3-yl group, a 1,9-phenanthroline-4-yl group, a 1,9-phenanthroline-5-yl group, a 1,9-phenanthroline-6-yl group, a 1,9-phenanthroline-7-yl group, a 1,9-phenanthroline-8-yl group, a 1,9-phenanthroline-10-yl group, a 1,10-phenanthroline-2-yl group, a 1,10-phenanthroline-3-yl group, a 1,10-phenanthroline-4-yl group, a 1,10-phenanthroline-5-yl group, a 2,9-phenanthroline-1-yl group, a 2,9-phenanthroline-3-yl group, a 2,9-phenanthroline-4-yl group, a 2,9-phenanthroline-5-yl group, a 2,9-phenanthroline-6-yl group, a 2,9-phenanthroline-7-yl group, a 2,9-phenanthroline-8-yl group, a 2,9-phenanthroline-10-yl group, a 2,8-phenanthroline-1-yl group, a 2,8-phenanthroline-3-yl group, a 2,8-phenanthroline-4-yl group, a 2,8-phenanthroline-5-yl group, a 2,8-phenanthroline-6-yl group, a 2,8-phenanthroline-7-yl group, a 2,8-phenanthroline-9-yl group, a 2,8-phenanthroline-10-yl group, a 2,7-phenanthroline-1-yl group, a 2,7-phenanthroline-3-yl group, a 2,7-phenanthroline-4-yl group, a 2,7-phenanthroline-5-yl group, a 2,7-phenanthroline-6-yl group, a 2,7-phenanthroline-8-yl group, a 2,7-phenanthroline-9-yl group, a 2,7-phenanthroline-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrole-1-yl group, a 2-methylpyrrole-3-yl group, a 2-methylpyrrole-4-yl group, a 2-methylpyrrole-5-yl group, a 3-methylpyrrole-1-yl group, a 3-methylpyrrole-2-yl group, a 3-methylpyrrole-4-yl group, a 3-methylpyrrole-5-yl group, a 2-t-butylpyrrole-4-yl group, a 3-(2-phenylpropyl)pyrrole-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, a 4-t-butyl-3-indolyl group and the like can be given.

A 1-pyrrolyl group, a 2-pyrrolyl group, a 3-pyrrolyl group, a 1-carbazolyl group, a 2-carbazolyl group, a 3-carbazolyl group, a 4-carbazolyl group and a 9-carbazolyl group are preferable.

As the halogen atom, fluorine, chlorine and bromine can be given, with fluorine being preferable.

As the alkane residue and cycloalkane residue of L, residues corresponding to the above-mentioned alkyl group and cycloalkyl group can be given.

As the trialkylamine residue, triarylamine residue and alkylarylamine residue of L, residues in which the amine is substituted with the above-mentioned aryl group and alkyl group can be given.

As the aromatic hydrocarbon group and aromatic heterocyclic group of L, $Ar_1$, $Ar_2$ and $Ar_a$, residues corresponding to the above-mentioned aryl and heteroaryl groups can be given.

Specific examples of the aromatic amine derivative of the invention are shown below:

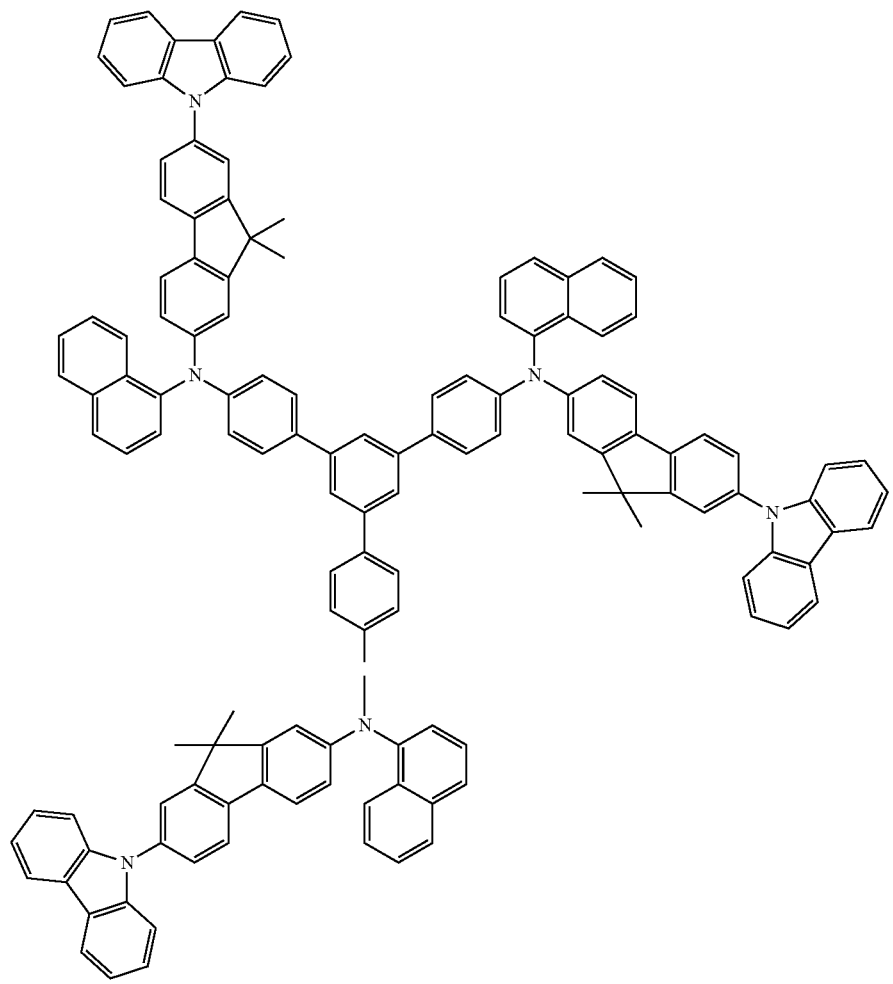 [SMILES: CC1(C)c2cc(N(c3ccc(-c4cc(-c5ccc(N(c6ccc7c(c6)C(C)(C)c6cc(-n8c9ccccc9c9ccccc98)ccc6-7)c6cccc7ccccc67)cc5)cc(-c5ccc(N(c6ccc7c(c6)C(C)(C)c6cc(-n8c9ccccc9c9ccccc98)ccc6-7)c6cccc7ccccc67)cc5)c4)cc3)c3cccc4ccccc34)ccc2-c2ccc(-n3c4ccccc4c4ccccc43)cc21]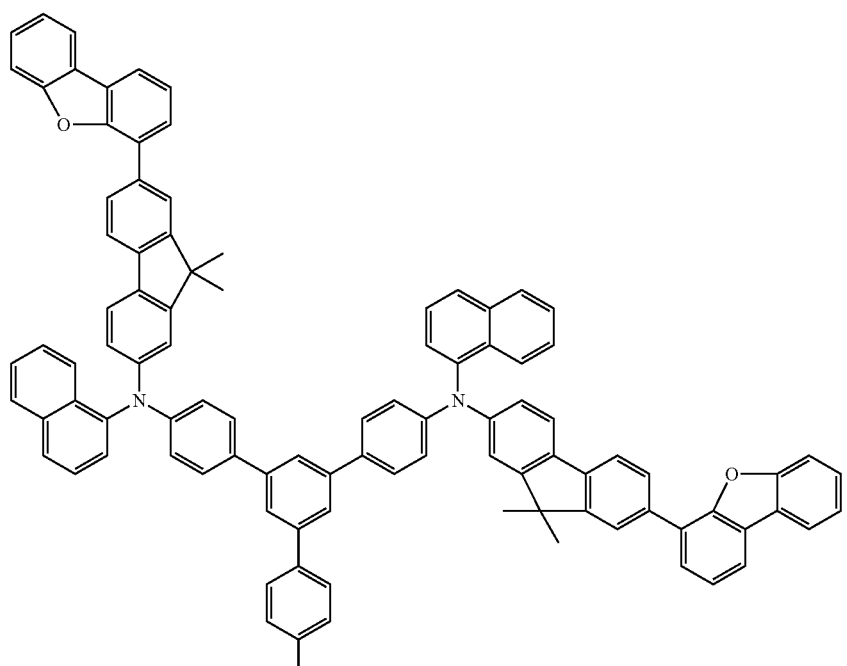

-continued
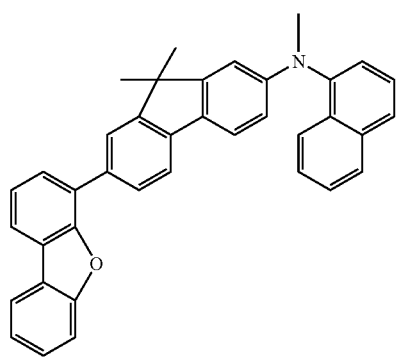
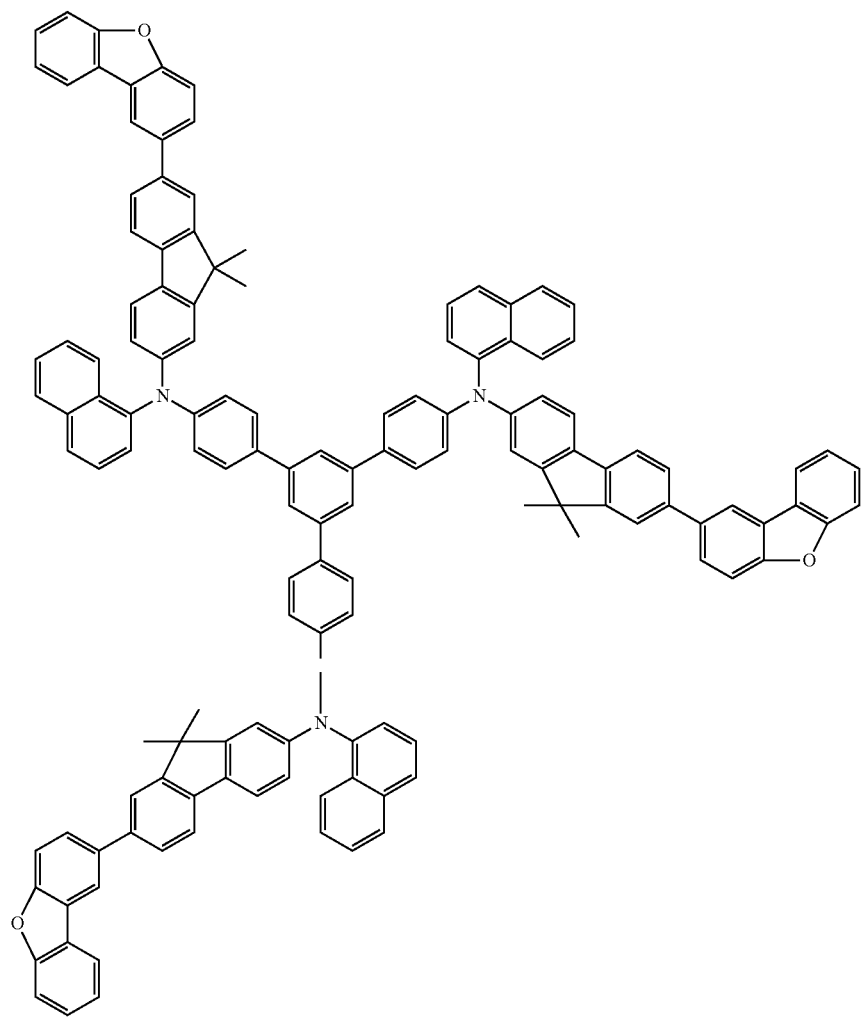

-continued
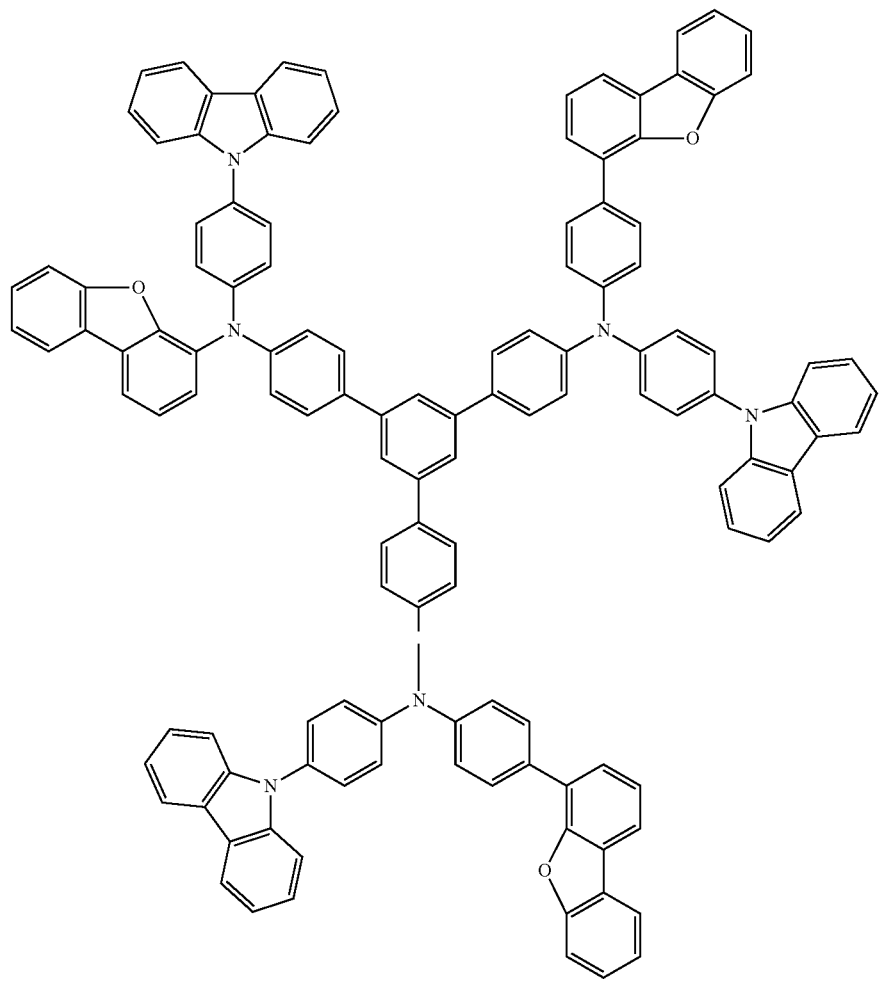 [SMILES: c1ccc2c(c1)oc1c(-c3ccc(N(c4ccc(-c5cc(-c6ccc(N(c7ccc(-c8cccc9c8oc8ccccc89)cc7)c7ccc(-n8c9ccccc9c9ccccc98)cc7)cc6)cc(-c6ccc(N(c7ccc(-n8c9ccccc9c9ccccc98)cc7)c7cccc8c7oc7ccccc78)cc6)c5)cc4)c4ccc(-n5c6ccccc6c6ccccc65)cc4)cc3)cccc12]
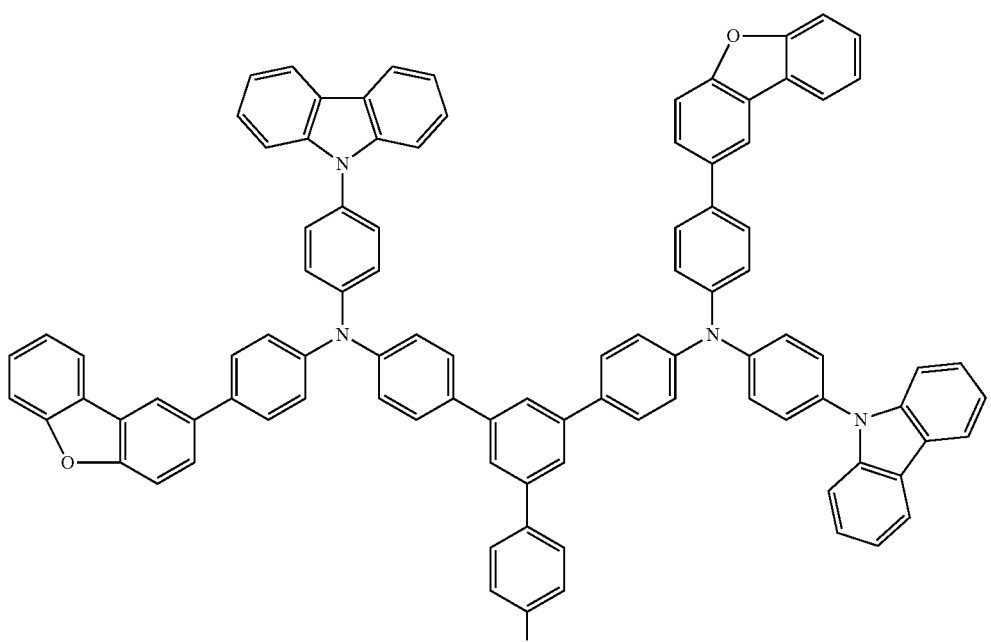

-continued
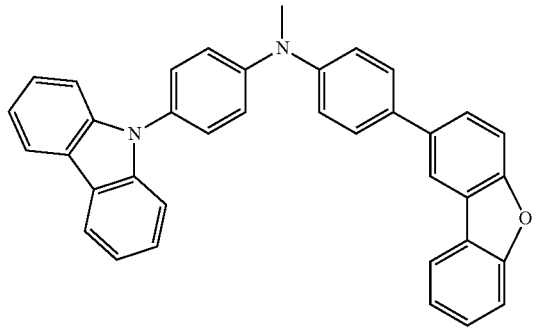
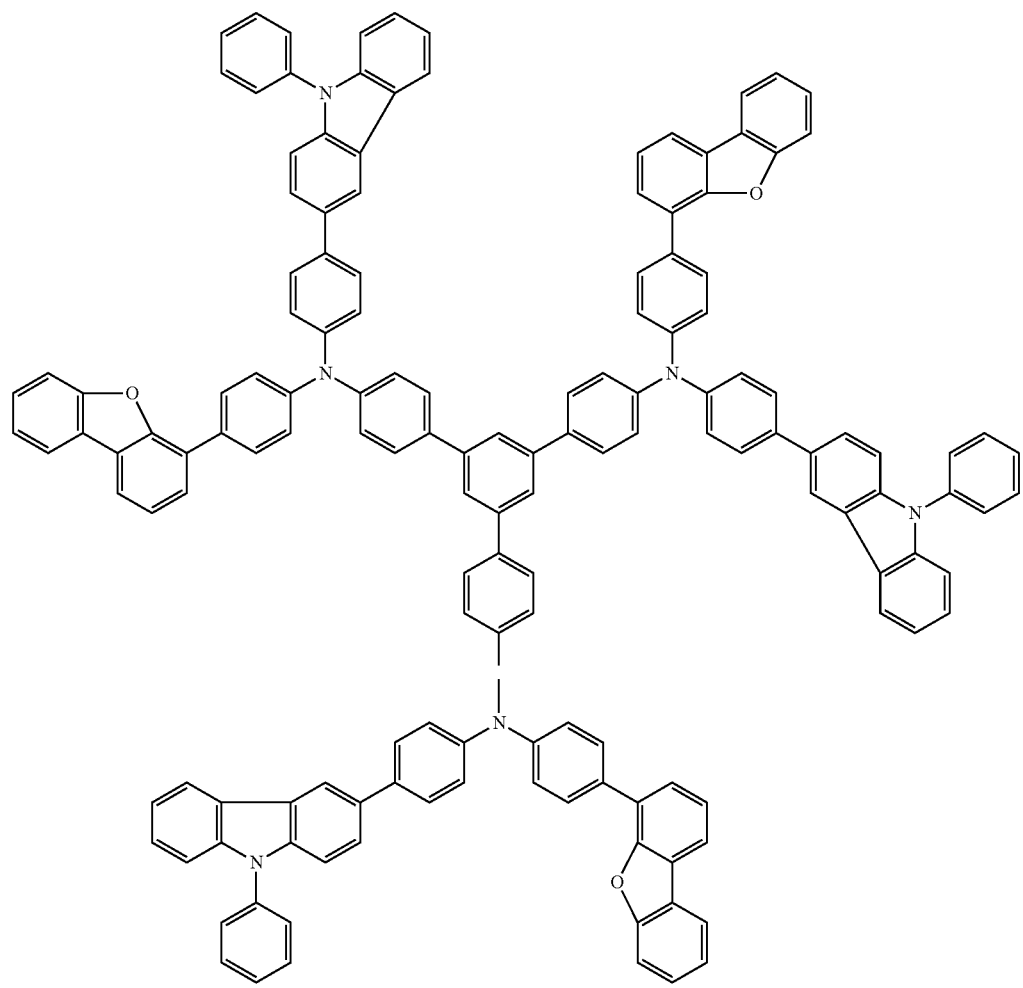 [SMILES: c1ccc(-n2c3ccccc3c3cc(-c4ccc(N(c5ccc(-c6cc(-c7ccc(N(c8ccc(-c9ccc%10c(c9)c9ccccc9n%10-c9ccccc9)cc8)c8ccc(-c9cccc%10c9oc9ccccc9%10)cc8)cc7)cc(-c7ccc(N(c8ccc(-c9ccc%10c(c9)c9ccccc9n%10-c9ccccc9)cc8)c8ccc(-c9cccc%10c9oc9ccccc9%10)cc8)cc7)c6)cc5)c5ccc(-c6cccc7c6oc6ccccc67)cc5)cc4)ccc32)cc1]

-continued
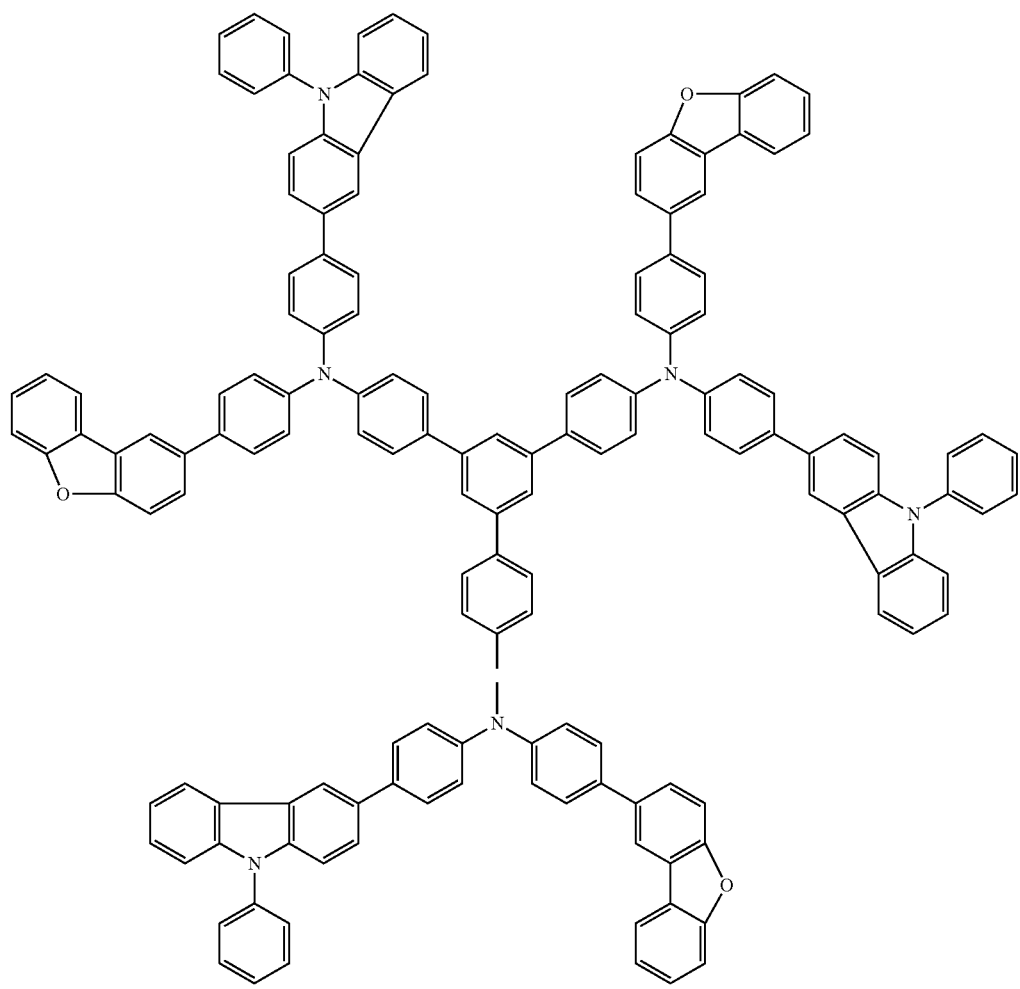 [SMILES: c1ccc(-n2c3ccccc3c3cc(-c4ccc(N(c5ccc(-c6cc(-c7ccc(N(c8ccc(-c9ccc%10oc%11ccccc%11c%10c9)cc8)c8ccc(-c9ccc%10c(c9)c9ccccc9n%10-c9ccccc9)cc8)cc7)cc(-c7ccc(N(c8ccc(-c9ccc%10oc%11ccccc%11c%10c9)cc8)c8ccc(-c9ccc%10c(c9)c9ccccc9n%10-c9ccccc9)cc8)cc7)c6)cc5)c5ccc(-c6ccc7oc8ccccc8c7c6)cc5)cc4)ccc32)cc1]
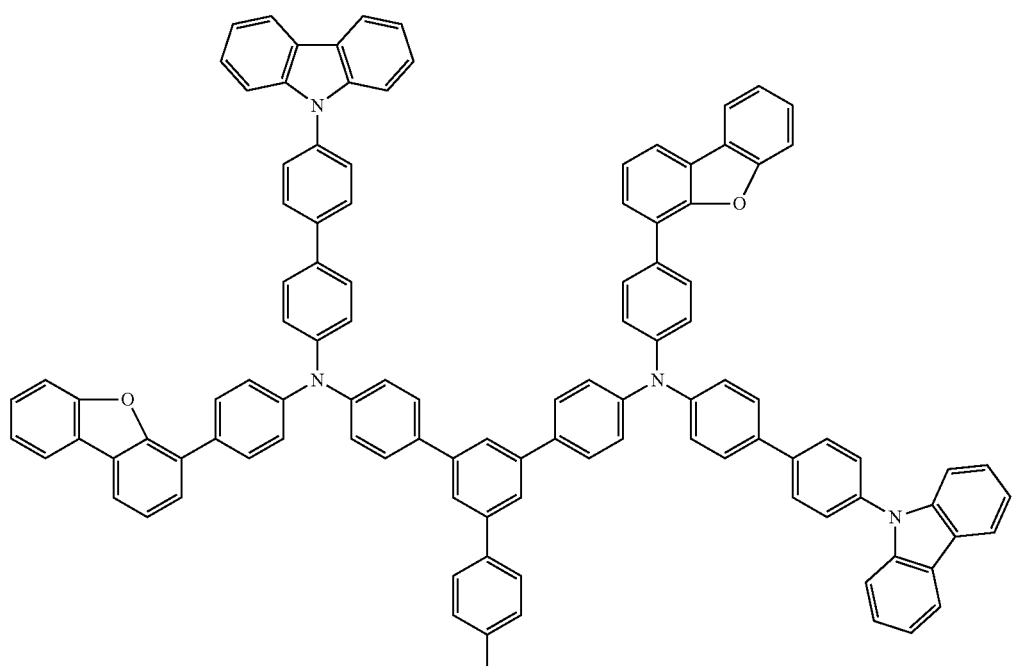

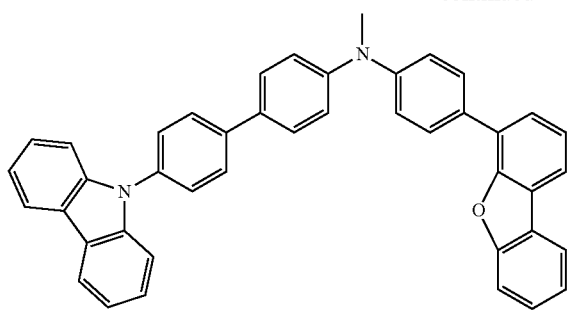
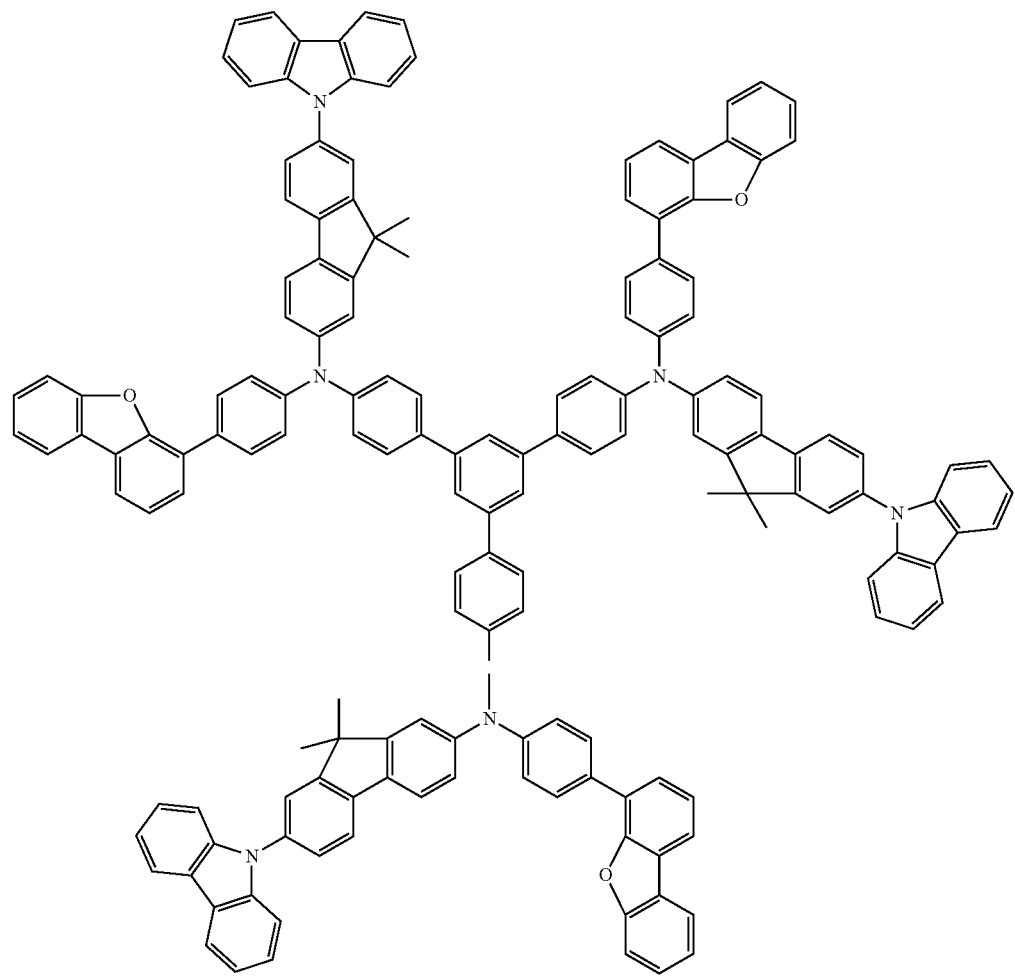 [SMILES: CC1(C)c2cc(N(c3ccc(-c4cc(-c5ccc(N(c6ccc(-c7cccc8c7oc7ccccc78)cc6)c6ccc7c(c6)C(C)(C)c6cc(-n8c9ccccc9c9ccccc98)ccc6-7)cc5)cc(-c5ccc(N(c6ccc(-c7cccc8c7oc7ccccc78)cc6)c6ccc7c(c6)C(C)(C)c6cc(-n8c9ccccc9c9ccccc98)ccc6-7)cc5)c4)cc3)c3ccc(-c4cccc5c4oc4ccccc45)cc3)ccc2-c2ccc(-n3c4ccccc4c4ccccc43)cc21]

-continued
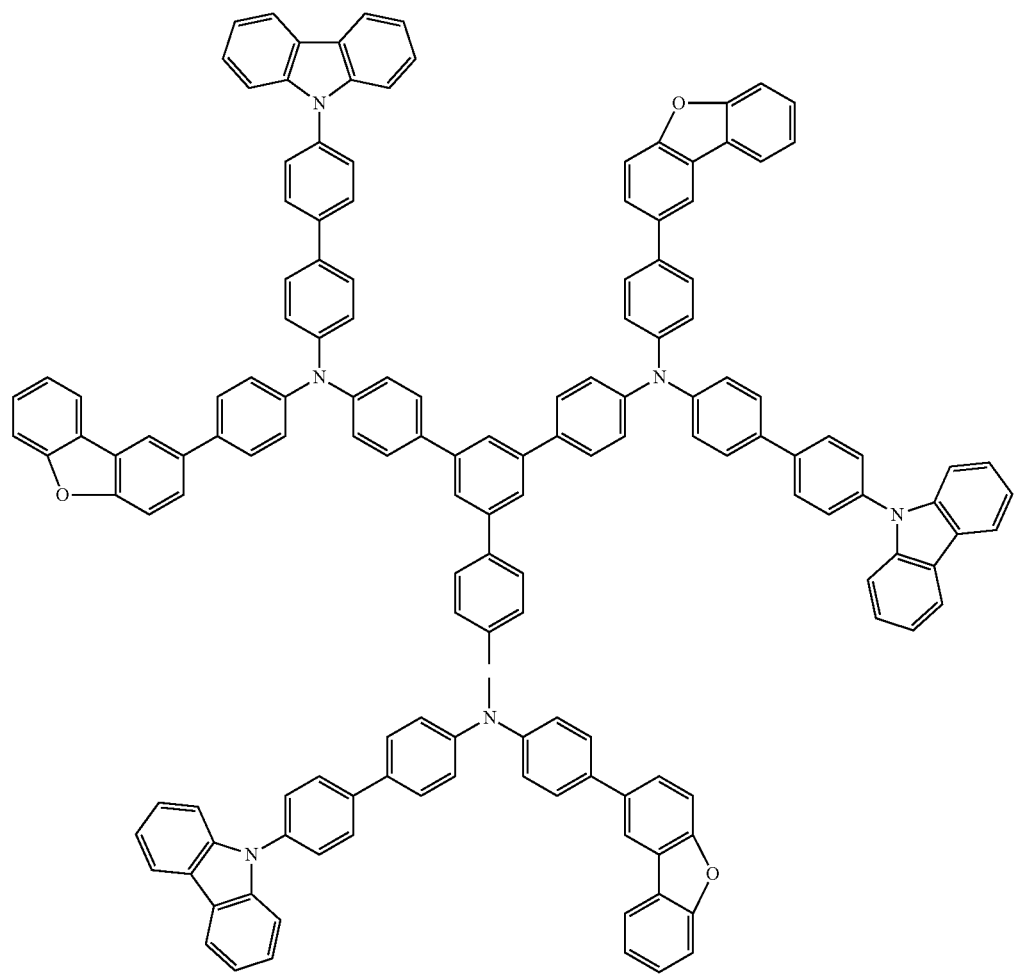 [SMILES: c1ccc2c(c1)oc1ccc(-c3ccc(N(c4ccc(-c5ccc(-n6c7ccccc7c7ccccc76)cc5)cc4)c4ccc(-c5cc(-c6ccc(N(c7ccc(-c8ccc(-n9c%10ccccc%10c%10ccccc%109)cc8)cc7)c7ccc(-c8ccc9oc%10ccccc%10c9c8)cc7)cc6)cc(-c6ccc(N(c7ccc(-c8ccc(-n9c%10ccccc%10c%10ccccc%109)cc8)cc7)c7ccc(-c8ccc9oc%10ccccc%10c9c8)cc7)cc6)c5)cc4)cc3)cc12]
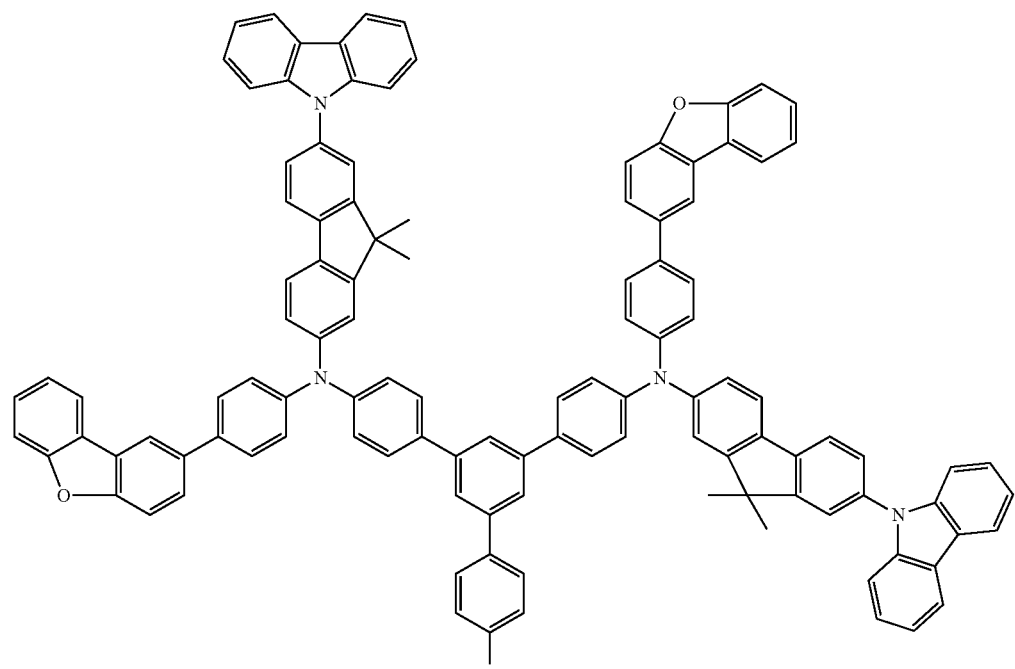

-continued
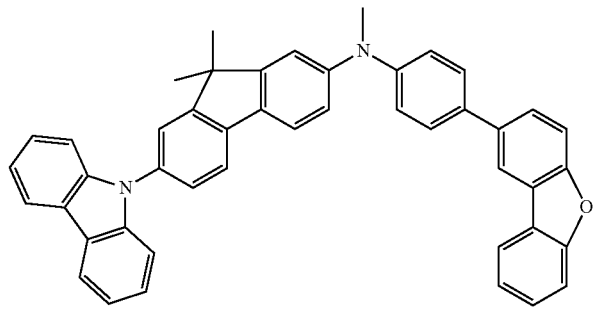
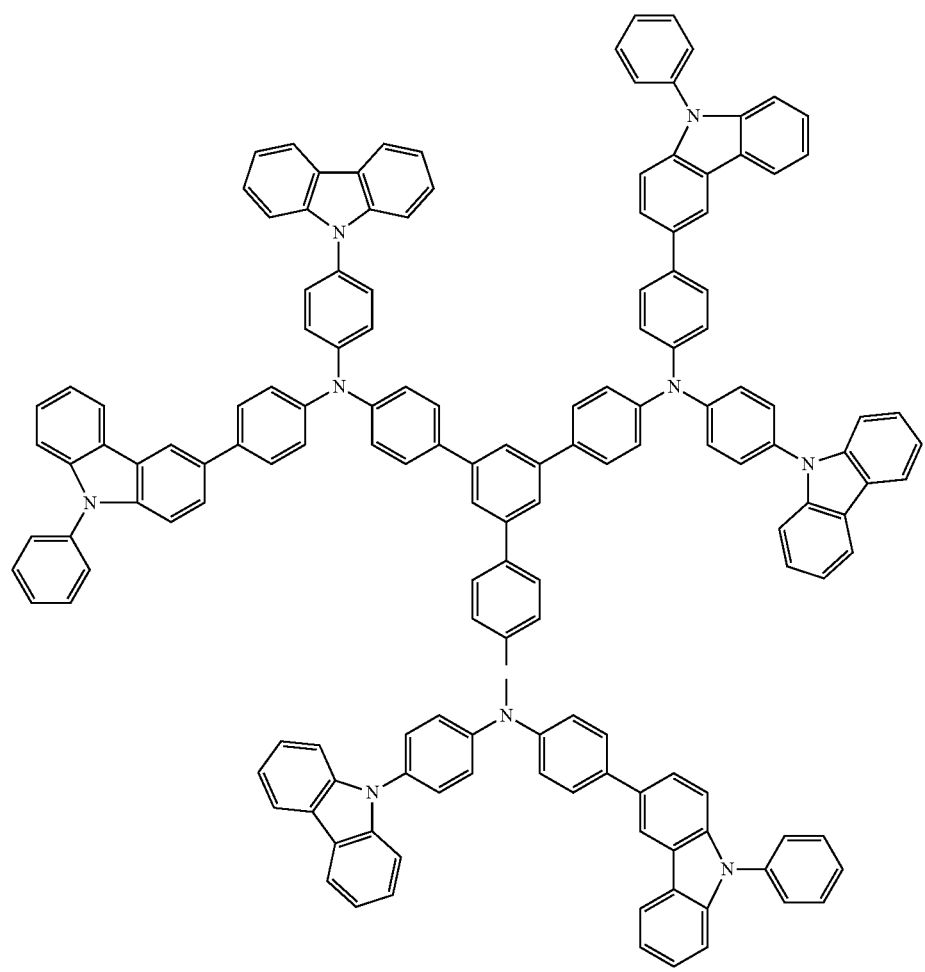 [SMILES: c1ccc(-n2c3ccccc3c3cc(-c4ccc(N(c5ccc(-c6cc(-c7ccc(N(c8ccc(-c9ccc%10c(c9)c9ccccc9n%10-c9ccccc9)cc8)c8ccc(-n9c%10ccccc%10c%10ccccc%109)cc8)cc7)cc(-c7ccc(N(c8ccc(-c9ccc%10c(c9)c9ccccc9n%10-c9ccccc9)cc8)c8ccc(-n9c%10ccccc%10c%10ccccc%109)cc8)cc7)c6)cc5)c5ccc(-n6c7ccccc7c7ccccc76)cc5)cc4)ccc32)cc1]

-continued
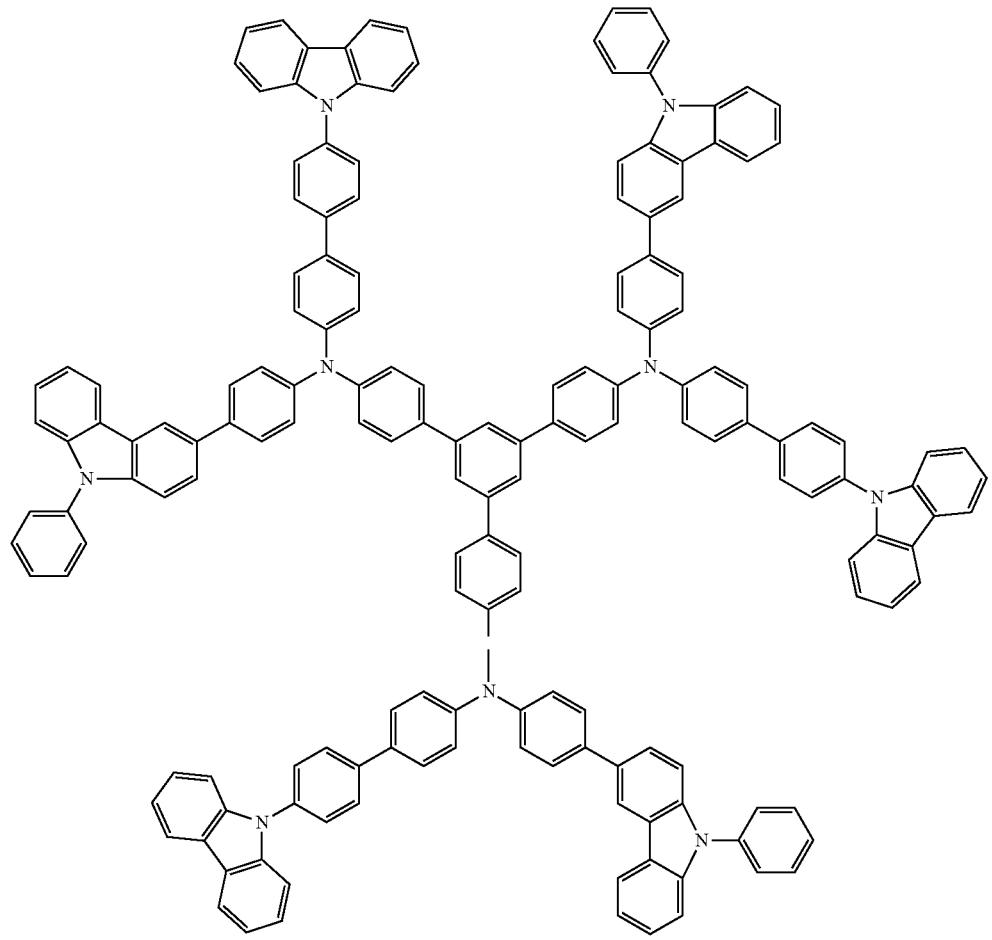 [SMILES: c1ccc(-n2c3ccccc3c3cc(-c4ccc(N(c5ccc(-c6ccc(-n7c8ccccc8c8ccccc87)cc6)cc5)c5ccc(-c6cc(-c7ccc(N(c8ccc(-c9ccc(-n%10c%11ccccc%11c%11ccccc%11%10)cc9)cc8)c8ccc(-c9ccc%10c(c9)c9ccccc9n%10-c9ccccc9)cc8)cc7)cc(-c7ccc(N(c8ccc(-c9ccc(-n%10c%11ccccc%11c%11ccccc%11%10)cc9)cc8)c8ccc(-c9ccc%10c(c9)c9ccccc9n%10-c9ccccc9)cc8)cc7)c6)cc5)cc4)ccc32)cc1]
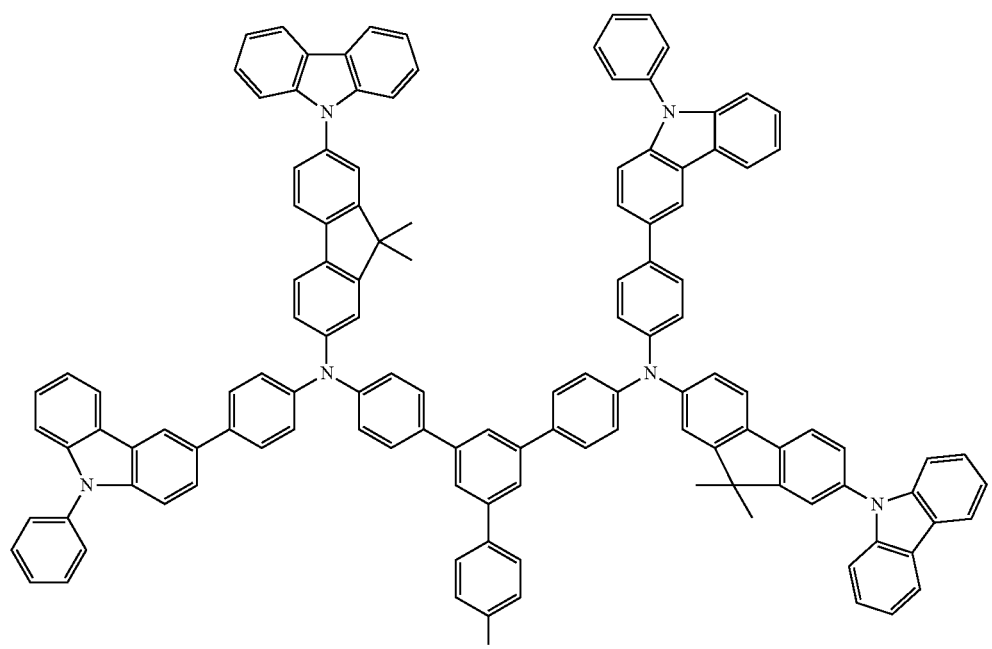

-continued
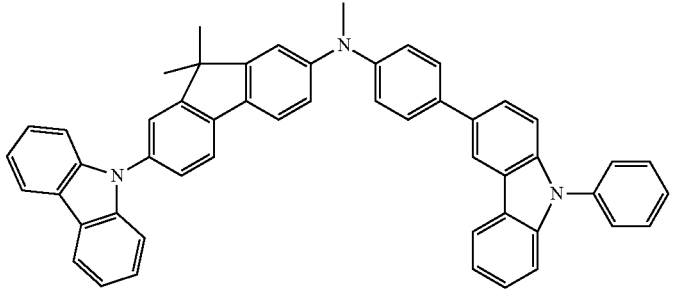
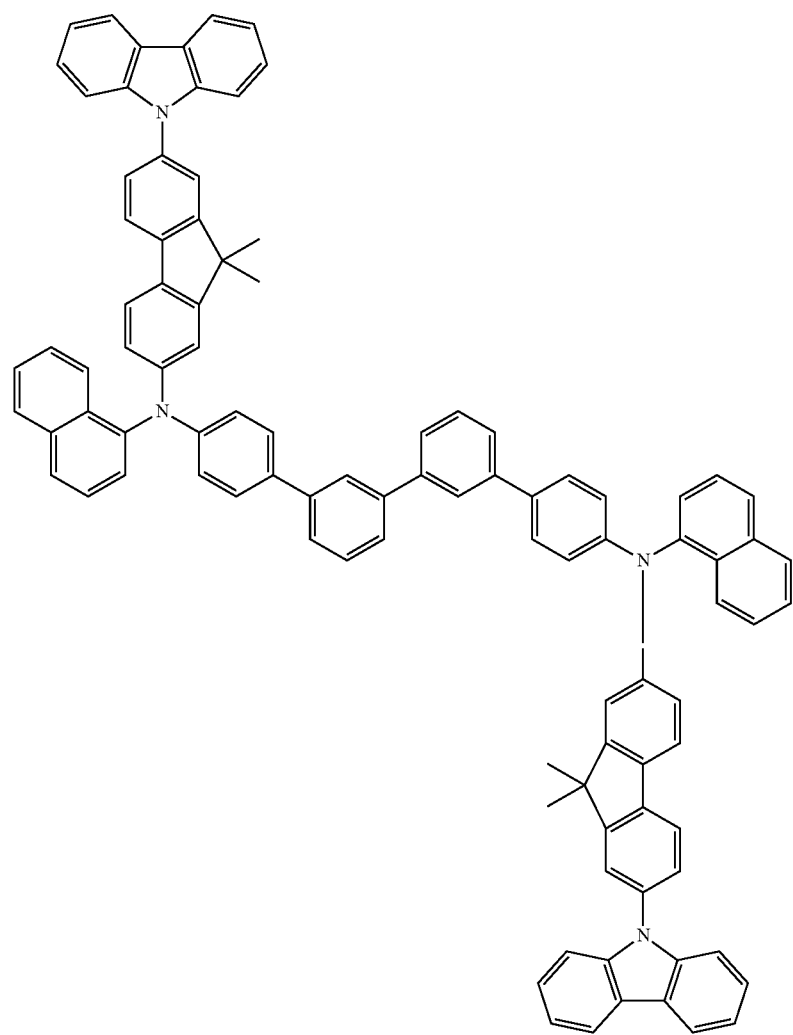 [SMILES: CC1(C)c2cc(N(c3ccc(-c4cccc(-c5cccc(-c6ccc(N(c7ccc8c(c7)C(C)(C)c7cc(-n9c%10ccccc%10c%10ccccc%109)ccc7-8)c7cccc8ccccc78)cc6)c5)c4)cc3)c3cccc4ccccc34)ccc2-c2ccc(-n3c4ccccc4c4ccccc43)cc21]

-continued
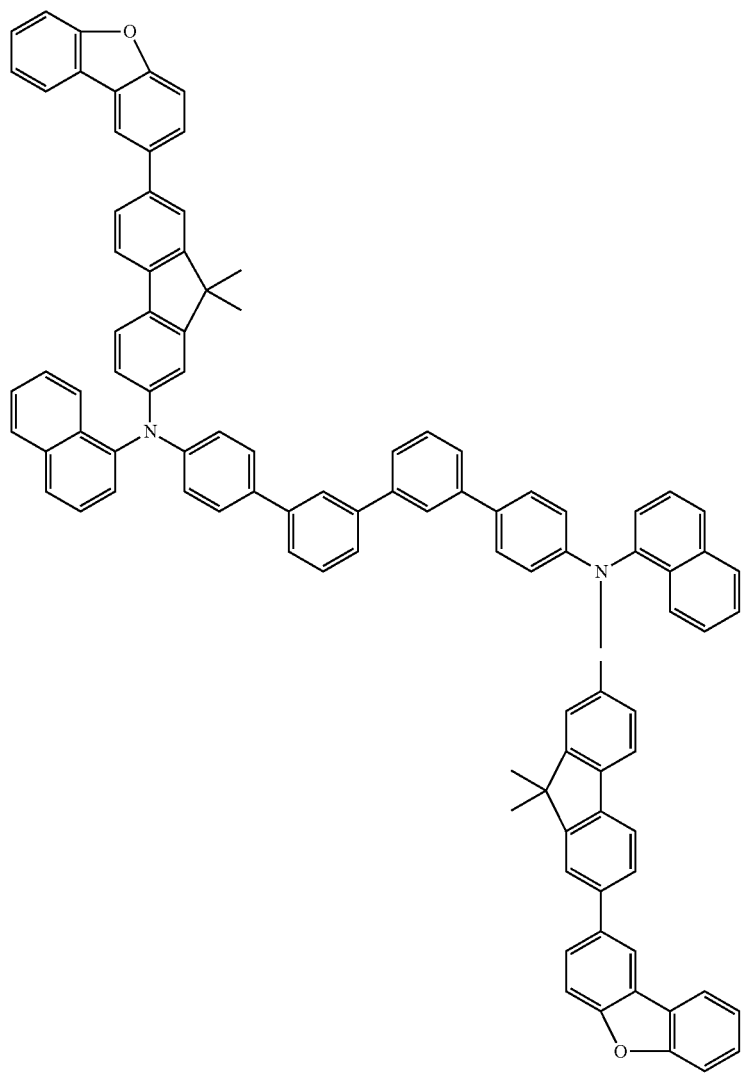 [SMILES: CC1(C)c2cc(-c3ccc4oc5ccccc5c4c3)ccc2-c2ccc(N(c3ccc(-c4cccc(-c5cccc(-c6ccc(N(c7ccc8c(c7)C(C)(C)c7cc(-c9ccc%10oc%11ccccc%11c%10c9)ccc7-8)c7cccc8ccccc78)cc6)c5)c4)cc3)c3cccc4ccccc34)cc21]
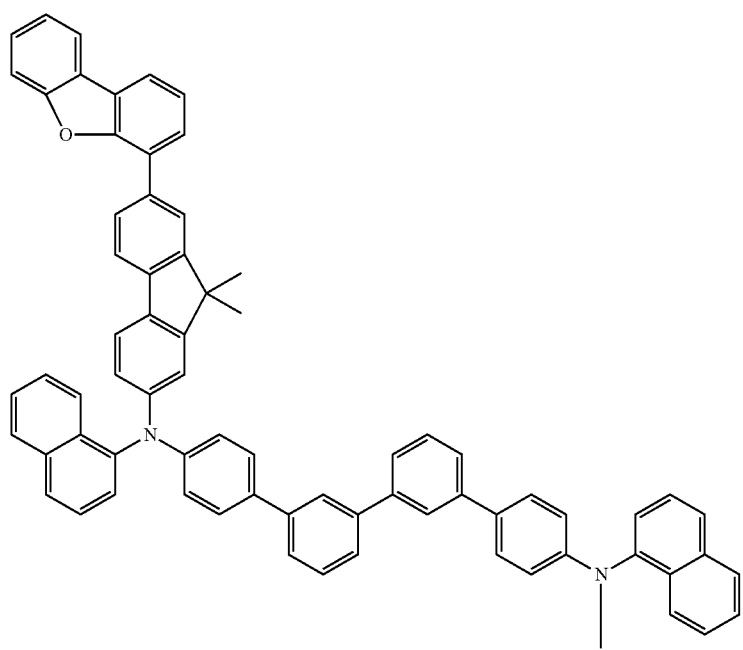

-continued
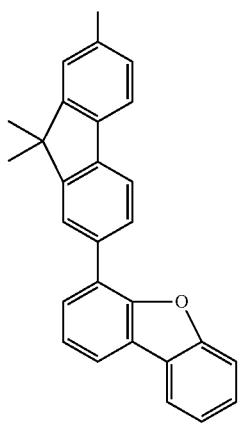
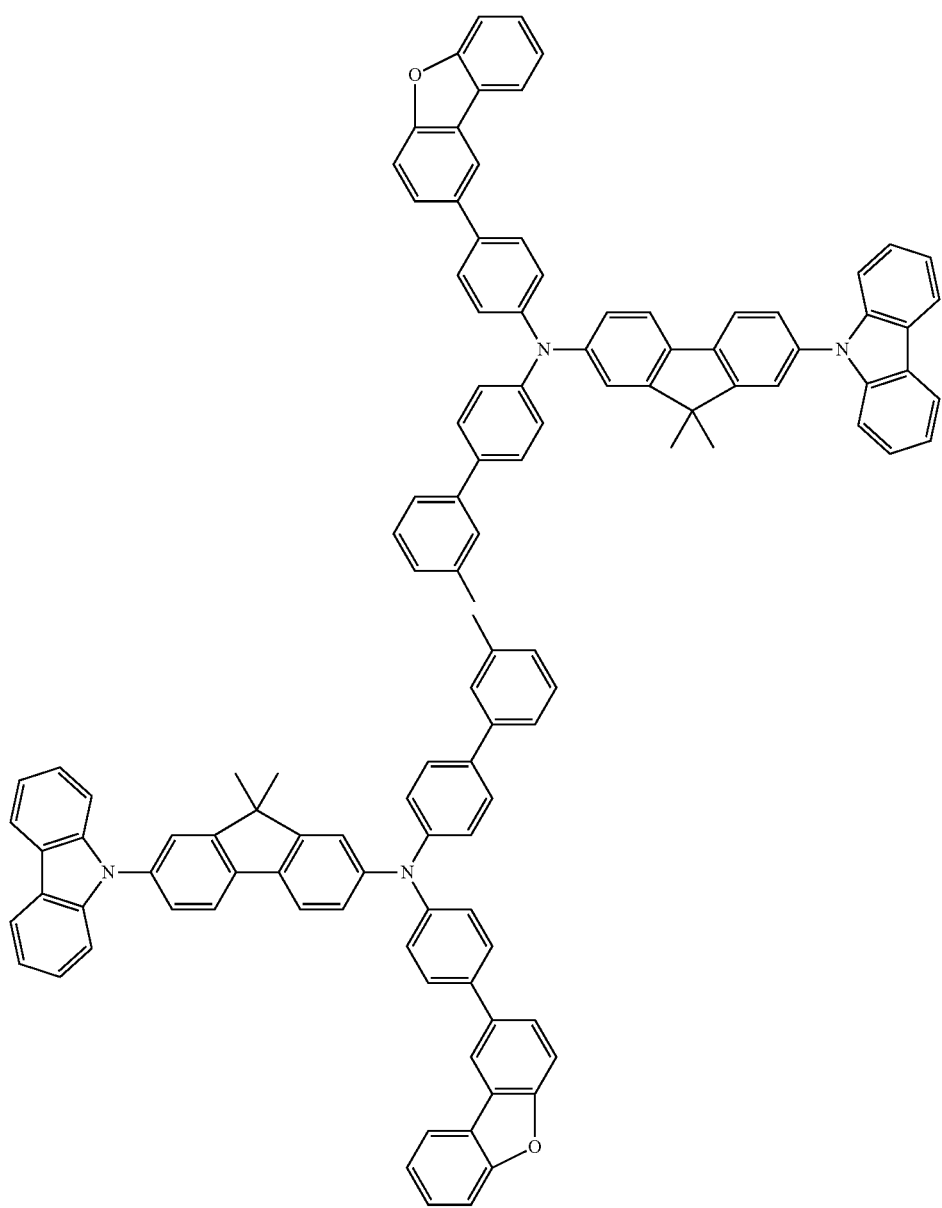 [SMILES: CC1(C)c2cc(N(c3ccc(-c4cccc(-c5cccc(-c6ccc(N(c7ccc(-c8ccc9oc%10ccccc%10c9c8)cc7)c7ccc8c(c7)C(C)(C)c7cc(-n9c%10ccccc%10c%10ccccc%109)ccc7-8)cc6)c5)c4)cc3)c3ccc(-c4ccc5oc6ccccc6c5c4)cc3)ccc2-c2ccc(-n3c4ccccc4c4ccccc43)cc21]

-continued
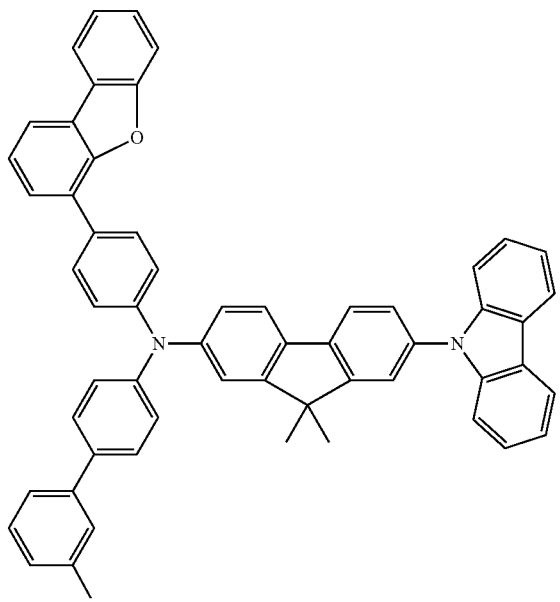
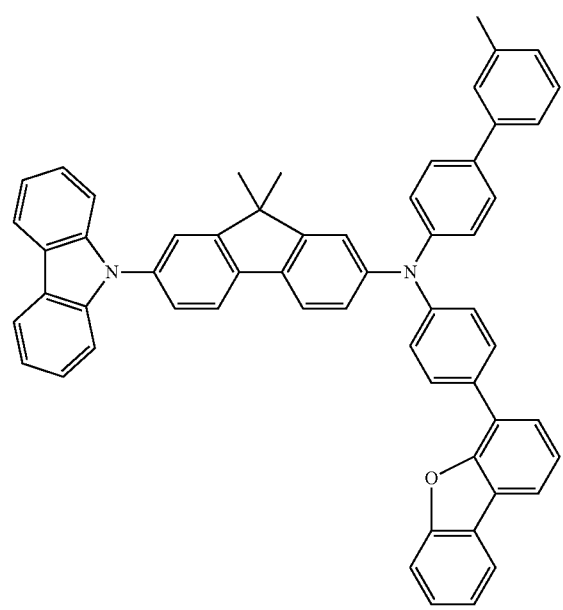

-continued
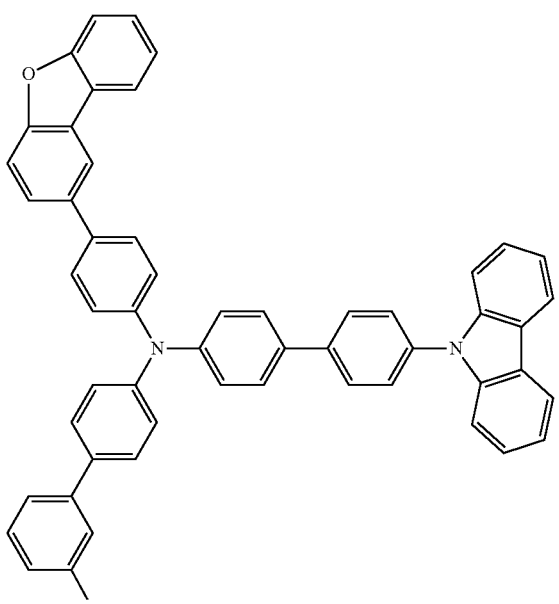
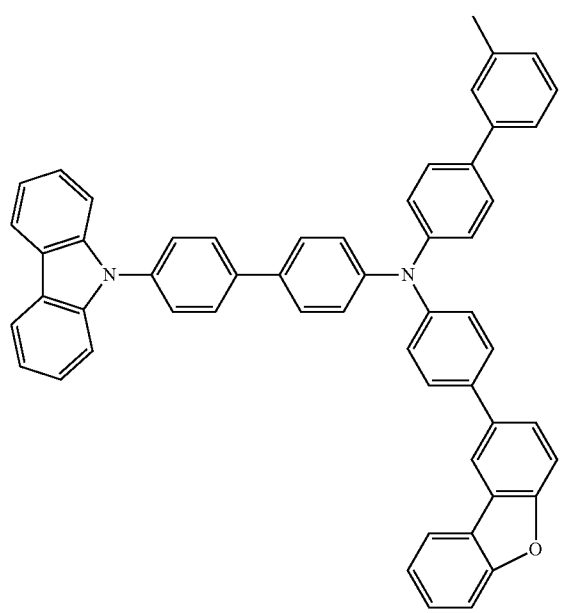

-continued
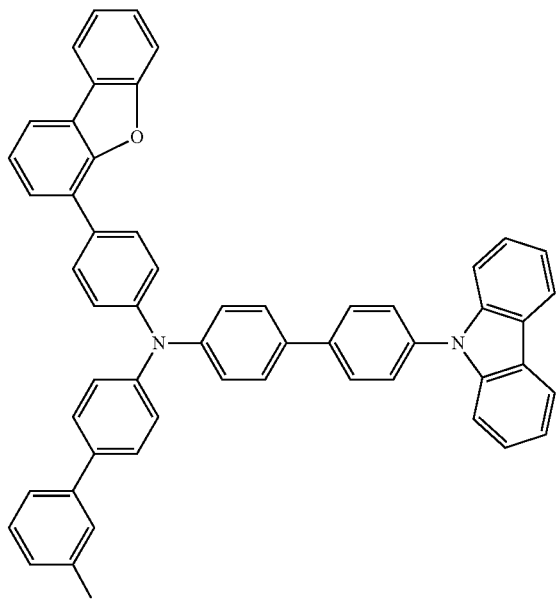
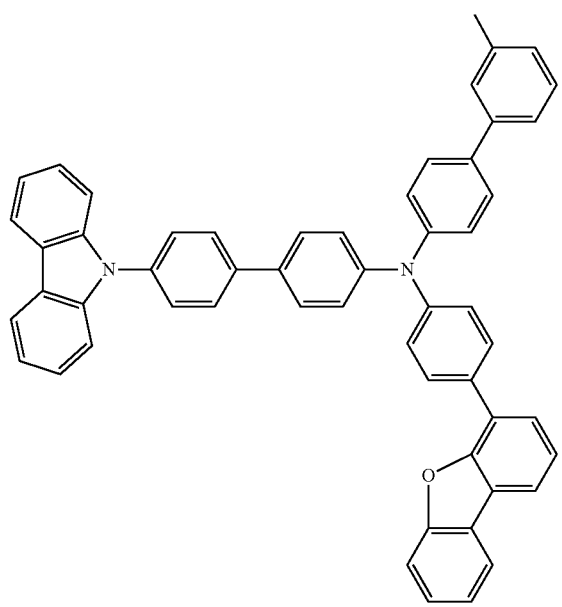

-continued
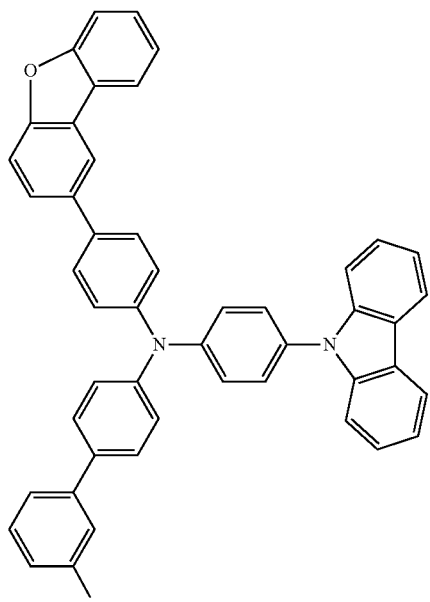
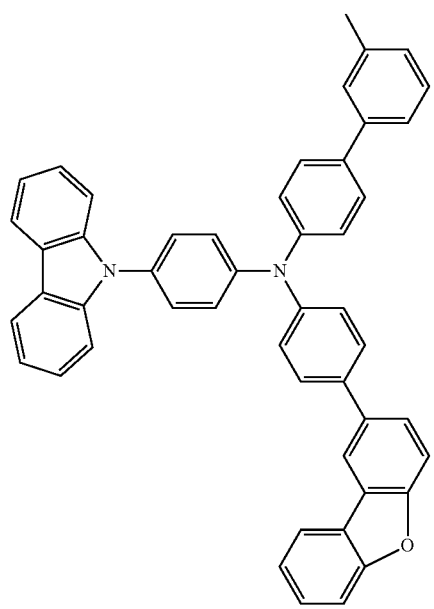

-continued
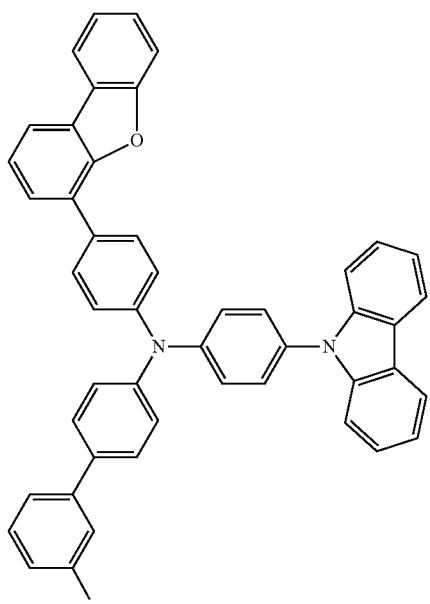
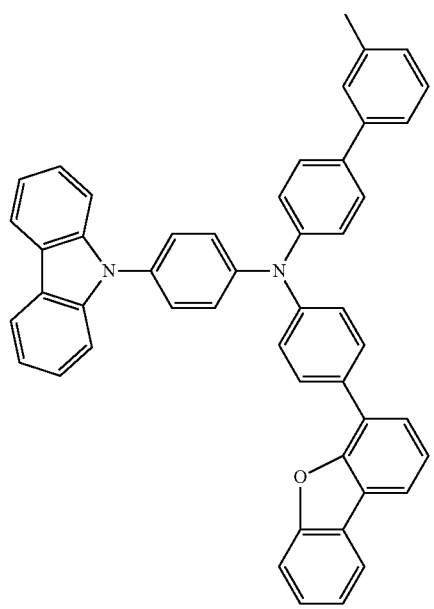

-continued
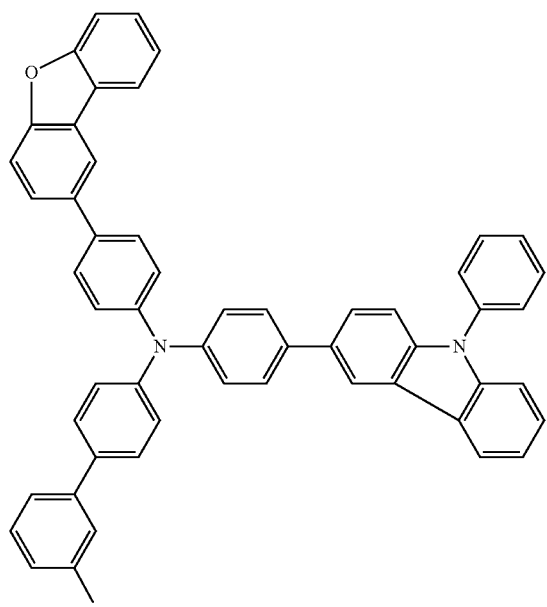
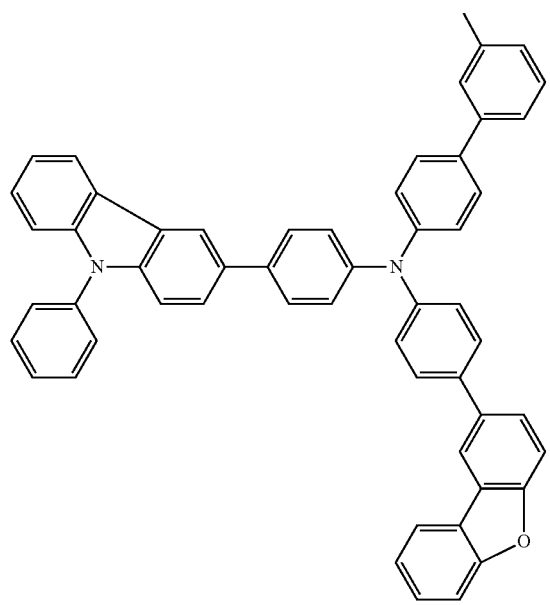

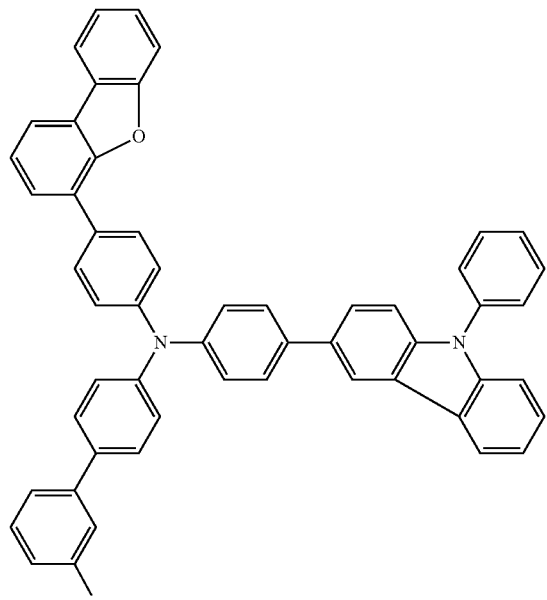
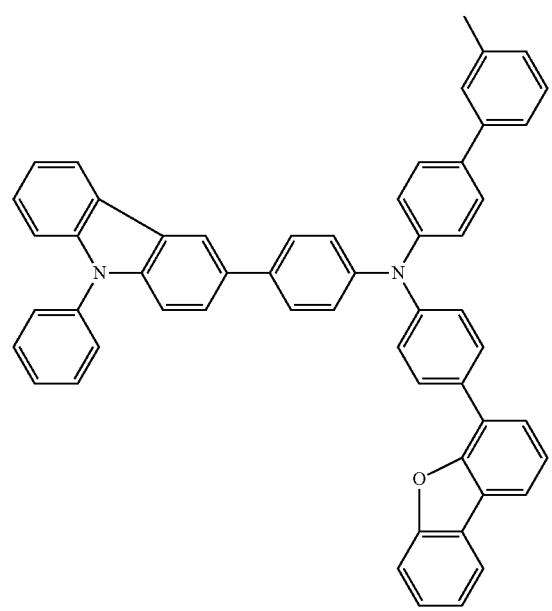

-continued
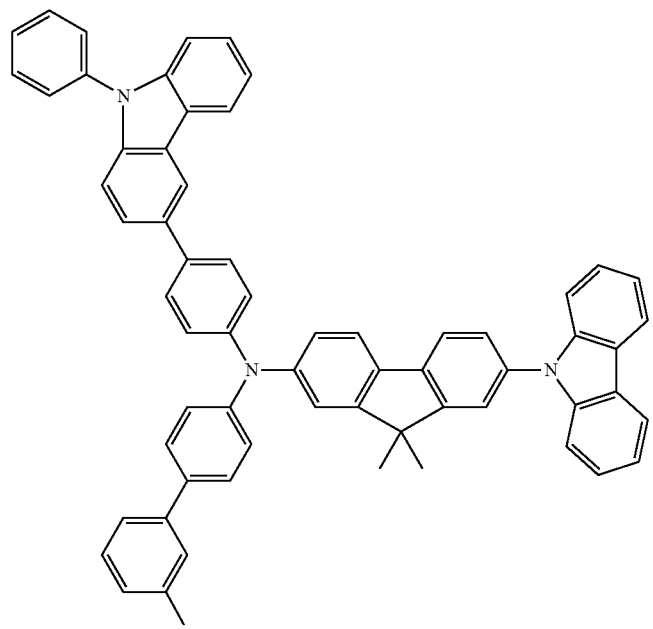
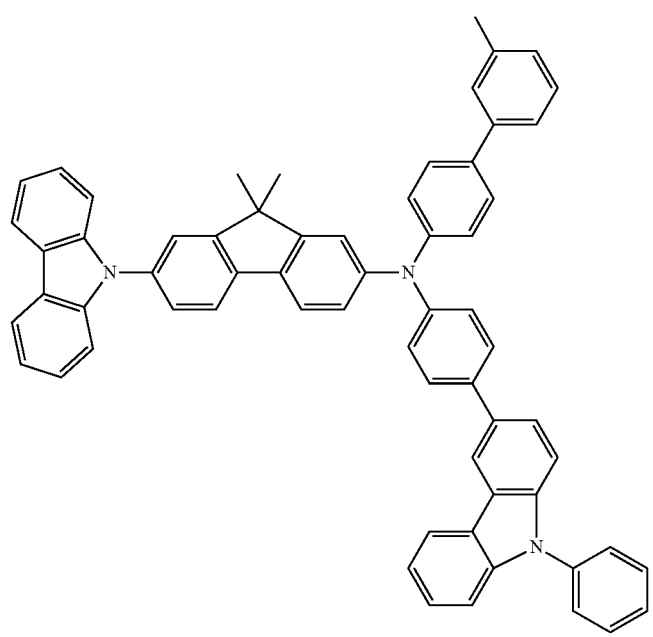

-continued
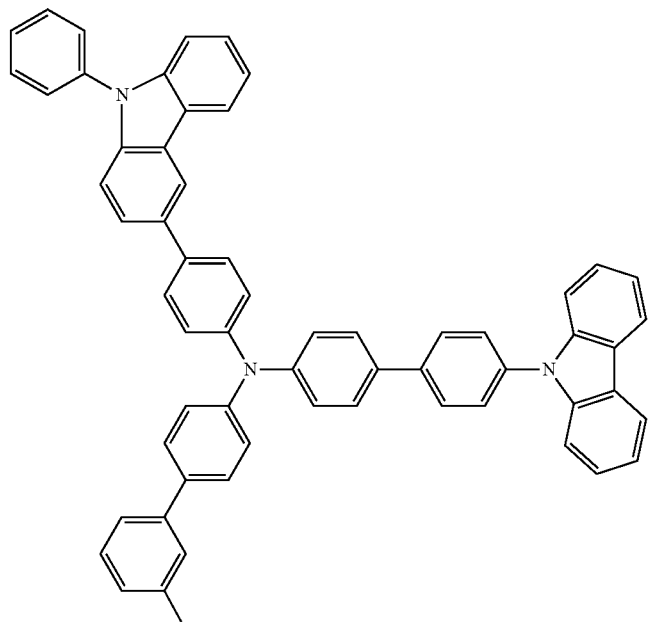
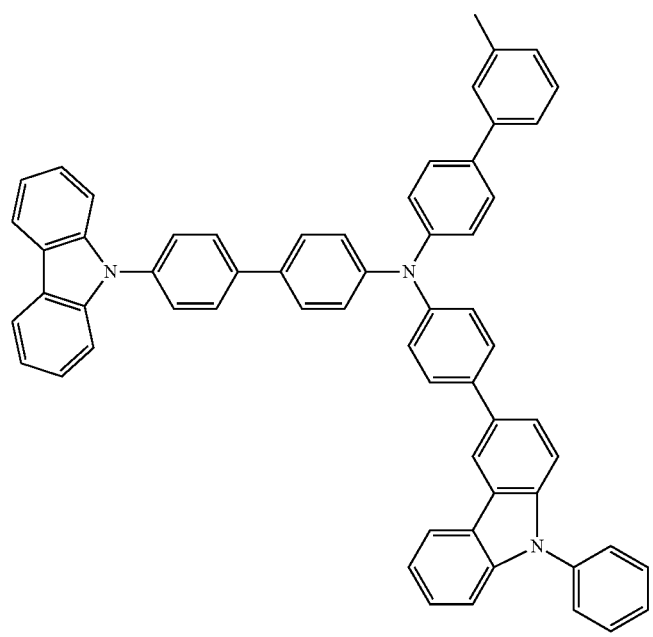

-continued
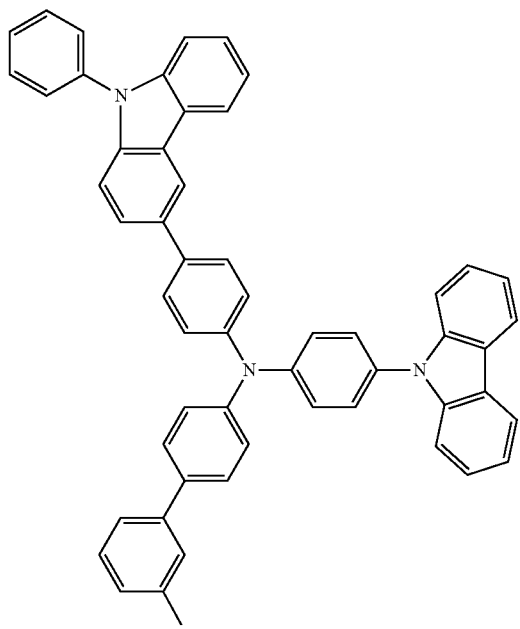
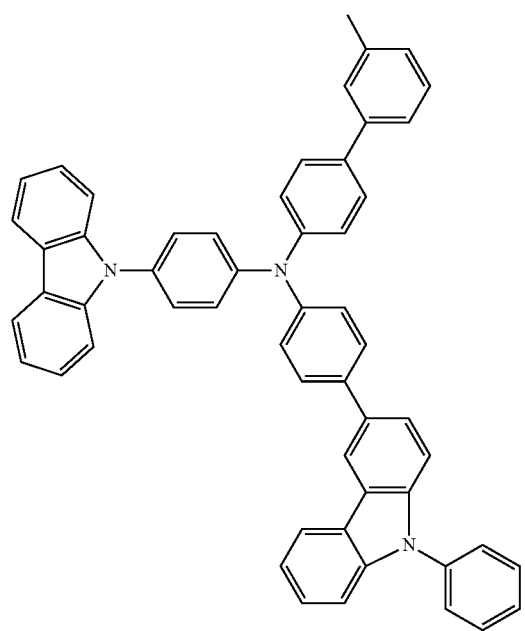

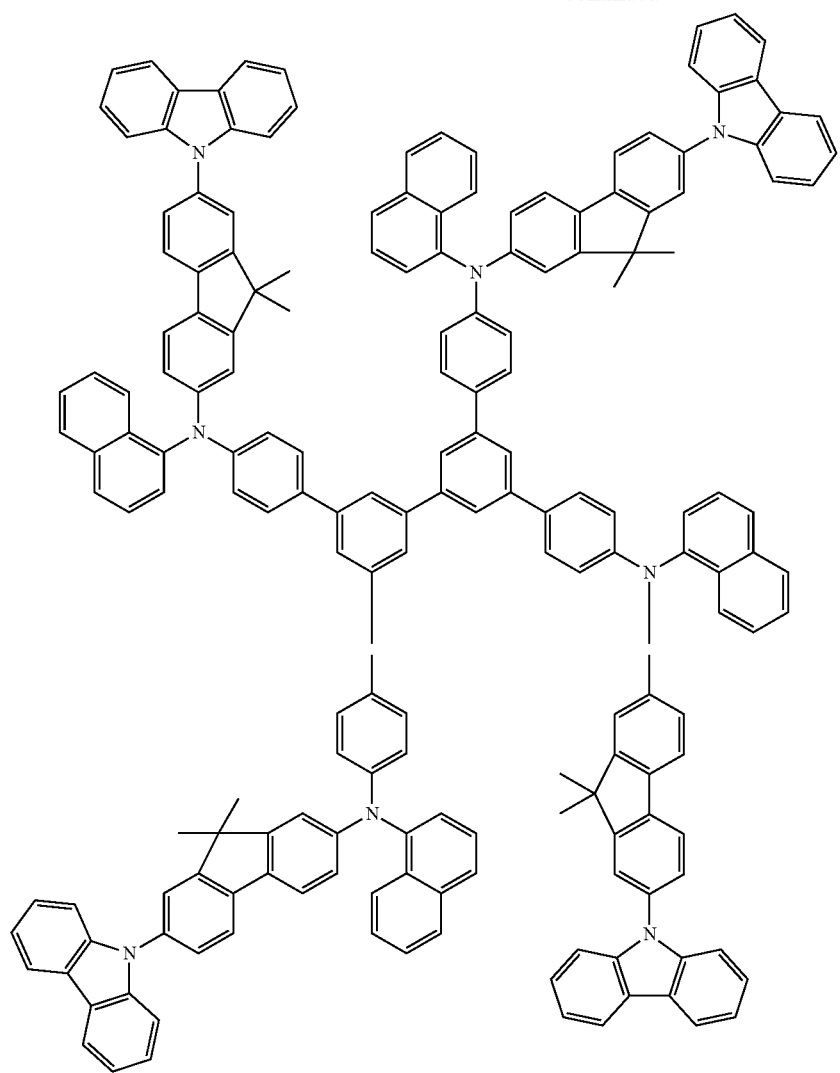 [SMILES: CC1(C)c2cc(N(c3ccc(-c4cc(-c5ccc(N(c6ccc7c(c6)C(C)(C)c6cc(-n8c9ccccc9c9ccccc98)ccc6-7)c6cccc7ccccc67)cc5)cc(-c5cc(-c6ccc(N(c7ccc8c(c7)C(C)(C)c7cc(-n9c%10ccccc%10c%10ccccc%109)ccc7-8)c7cccc8ccccc78)cc6)cc(-c6ccc(N(c7ccc8c(c7)C(C)(C)c7cc(-n9c%10ccccc%10c%10ccccc%109)ccc7-8)c7cccc8ccccc78)cc6)c5)c4)cc3)c3cccc4ccccc34)ccc2-c2ccc(-n3c4ccccc4c4ccccc43)cc21]
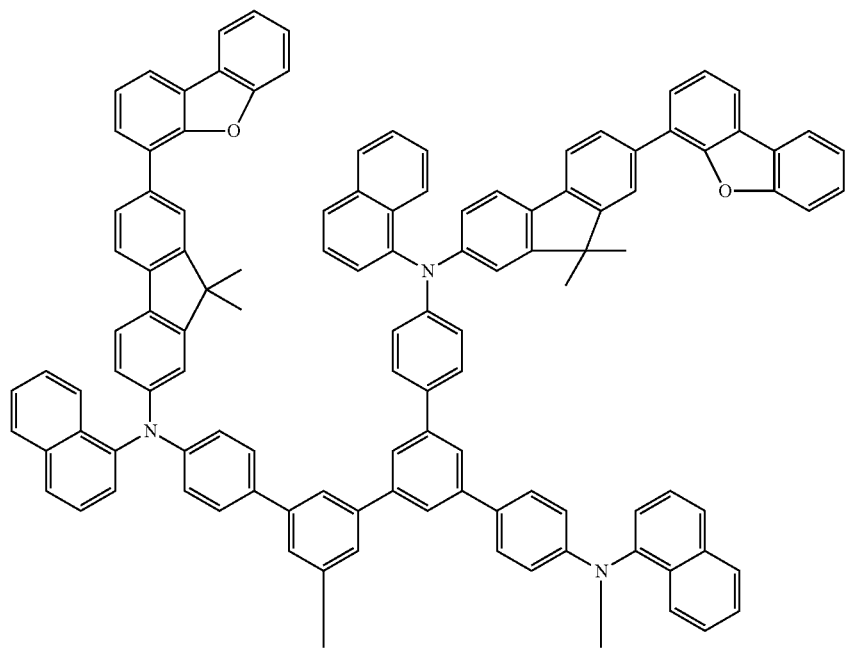

-continued
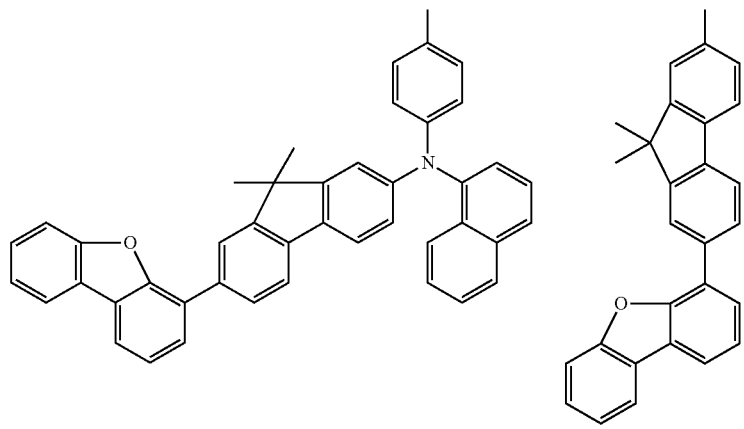
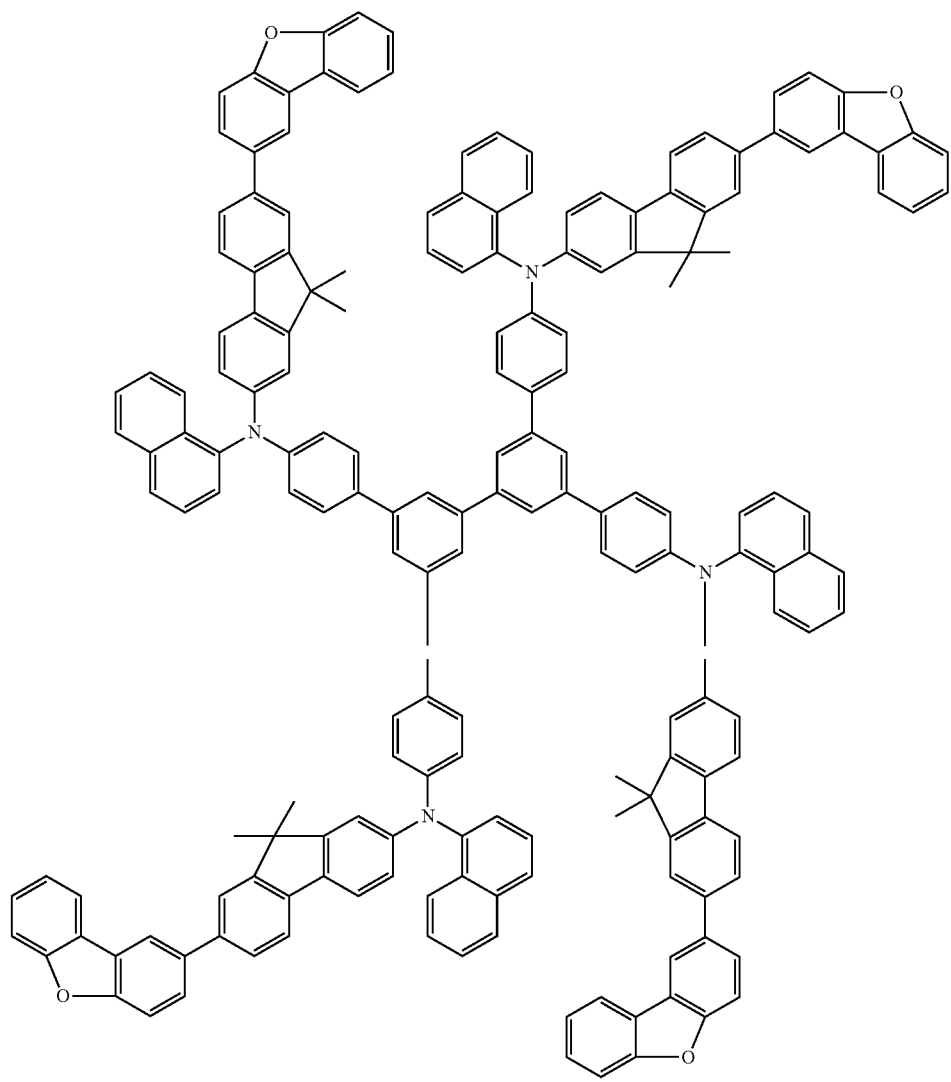 [SMILES: CC1(C)c2cc(-c3ccc4oc5ccccc5c4c3)ccc2-c2ccc(N(c3ccc(-c4cc(-c5ccc(N(c6ccc7c(c6)C(C)(C)c6cc(-c8ccc9oc%10ccccc%10c9c8)ccc6-7)c6cccc7ccccc67)cc5)cc(-c5cc(-c6ccc(N(c7ccc8c(c7)C(C)(C)c7cc(-c9ccc%10oc%11ccccc%11c%10c9)ccc7-8)c7cccc8ccccc78)cc6)cc(-c6ccc(N(c7ccc8c(c7)C(C)(C)c7cc(-c9ccc%10oc%11ccccc%11c%10c9)ccc7-8)c7cccc8ccccc78)cc6)c5)c4)cc3)c3cccc4ccccc34)cc21]

-continued
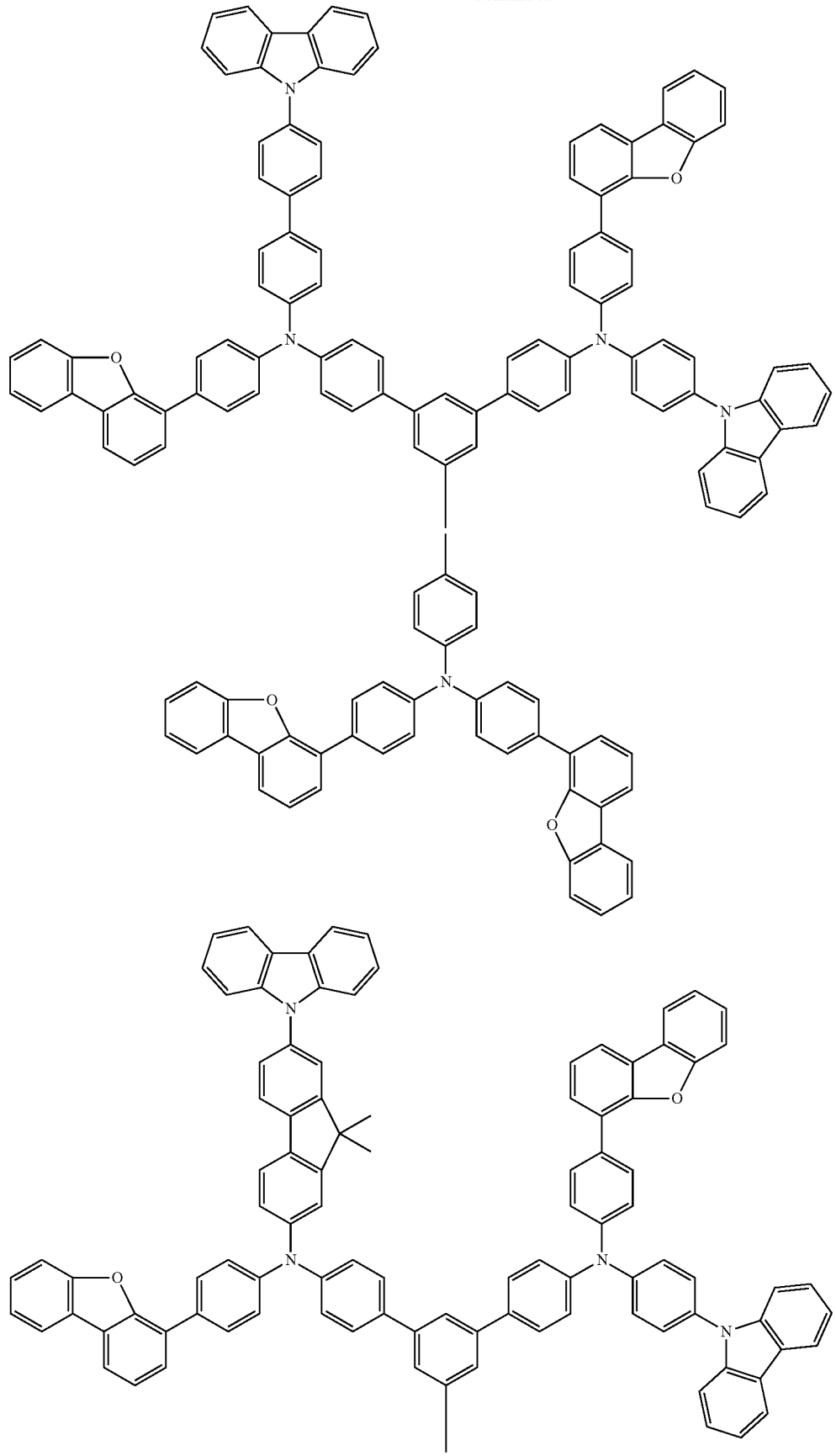

-continued
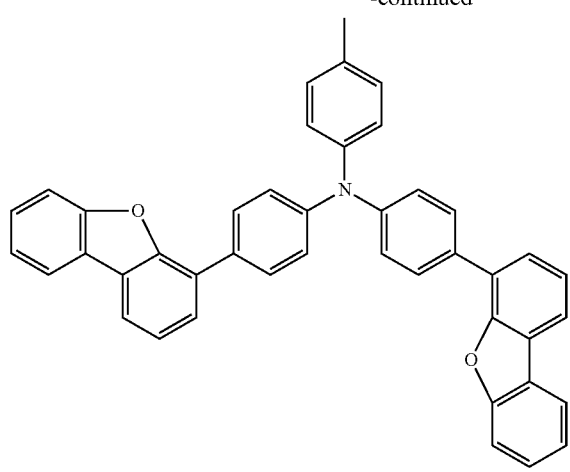
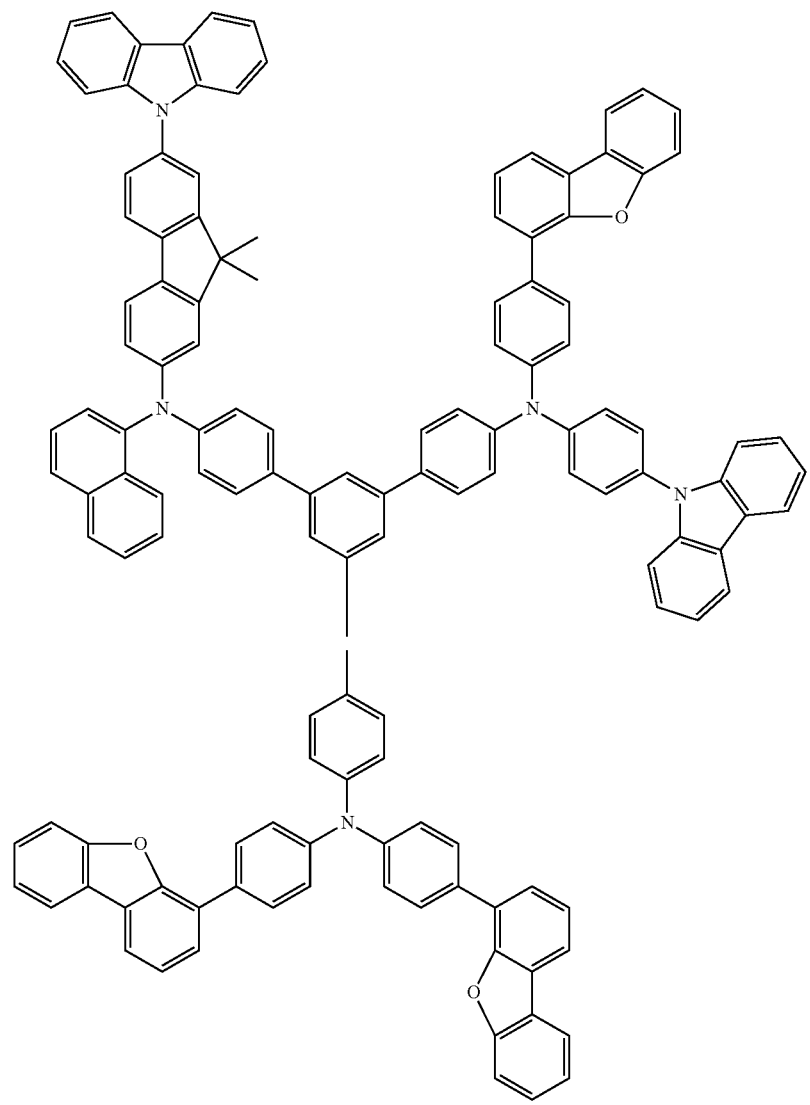 [SMILES: CC1(C)c2cc(N(c3ccc(-c4cc(-c5ccc(N(c6ccc(-c7cccc8c7oc7ccccc78)cc6)c6ccc(-c7cccc8c7oc7ccccc78)cc6)cc5)cc(-c5ccc(N(c6ccc(-c7cccc8c7oc7ccccc78)cc6)c6ccc(-n7c8ccccc8c8ccccc87)cc6)cc5)c4)cc3)c3cccc4ccccc34)ccc2-c2ccc(-n3c4ccccc4c4ccccc43)cc21]

-continued
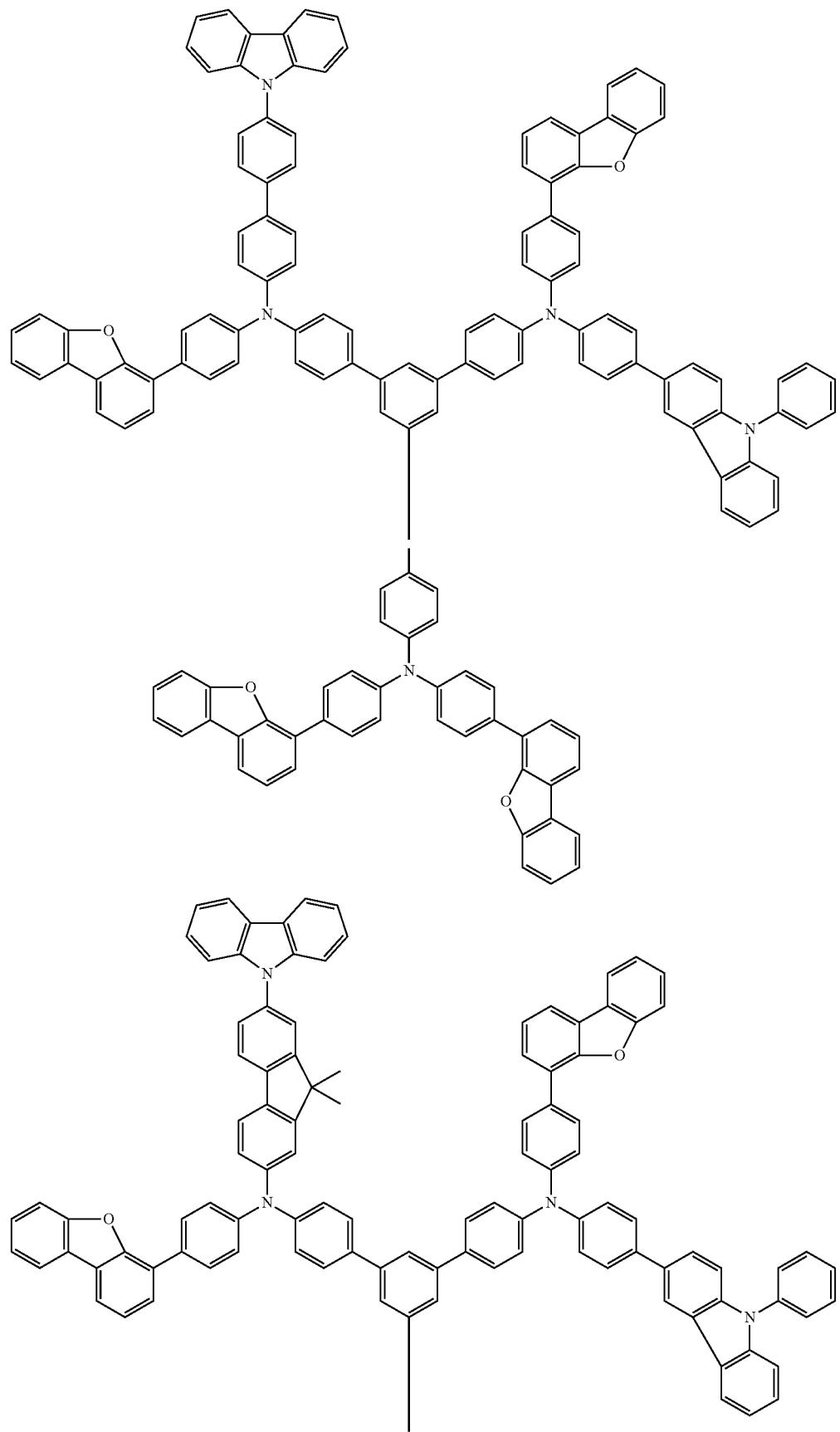

-continued
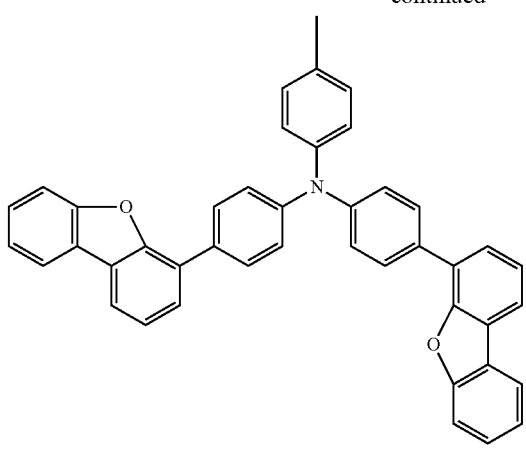
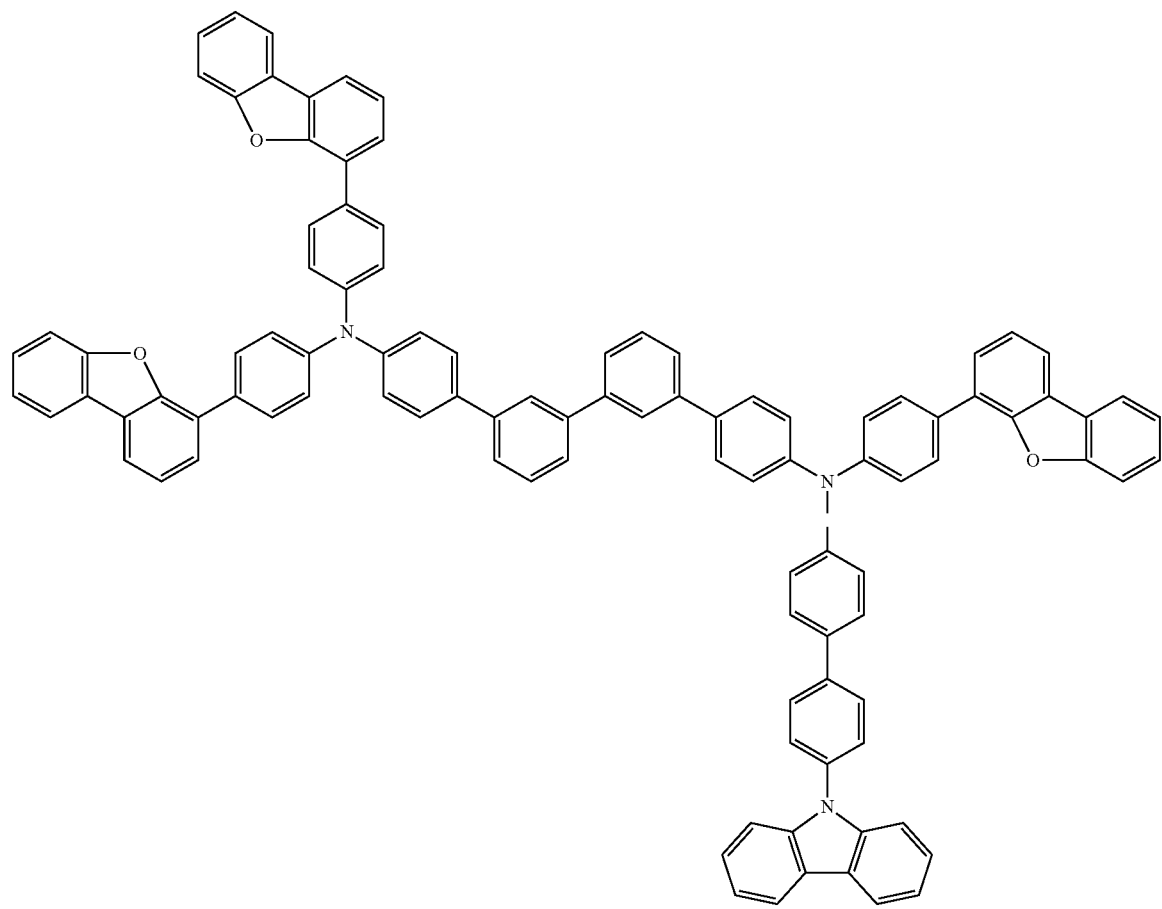

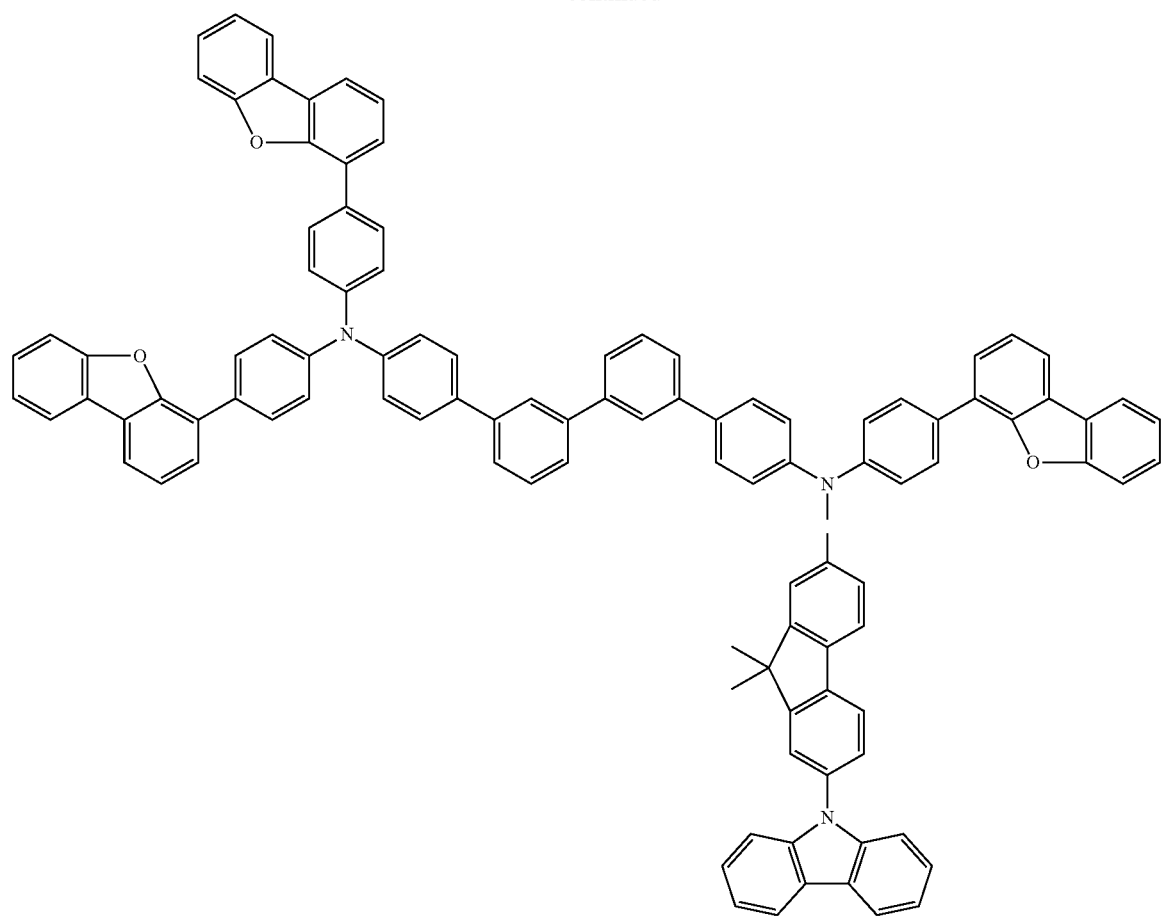
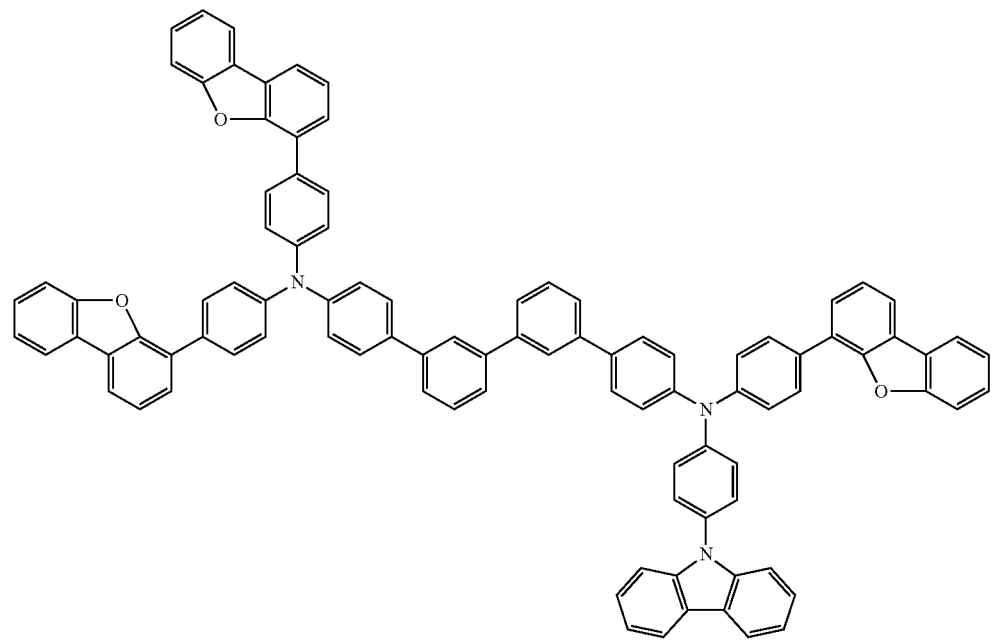

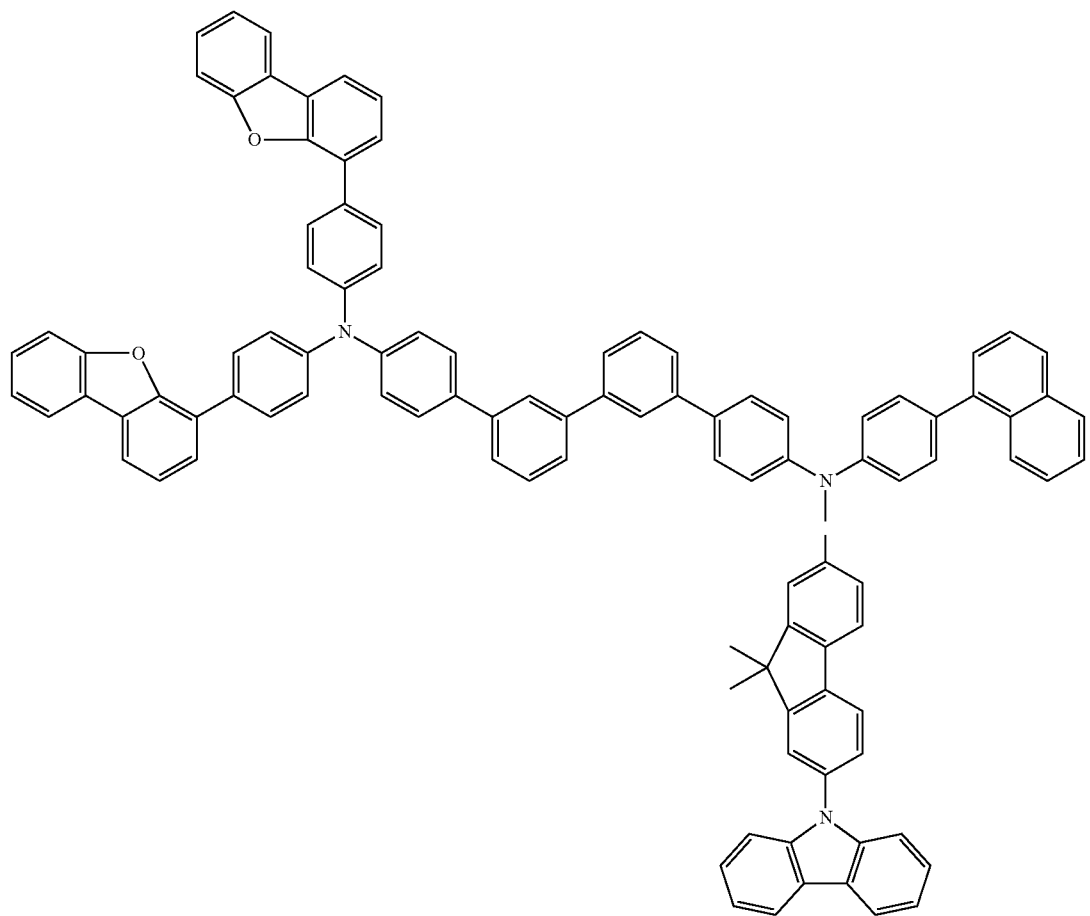
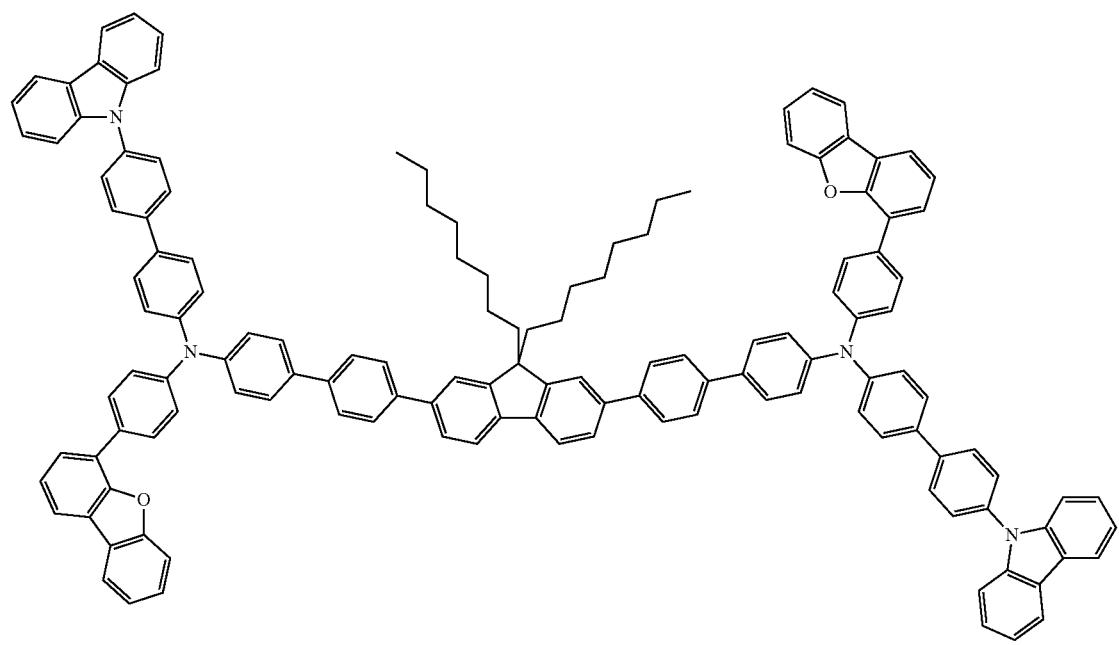

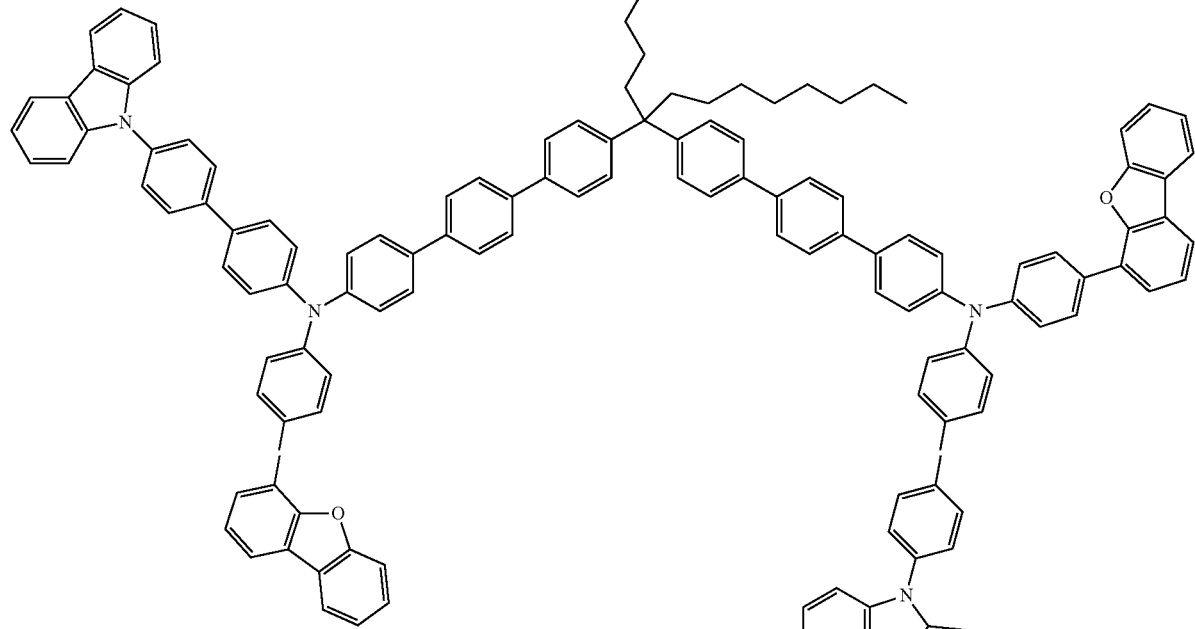
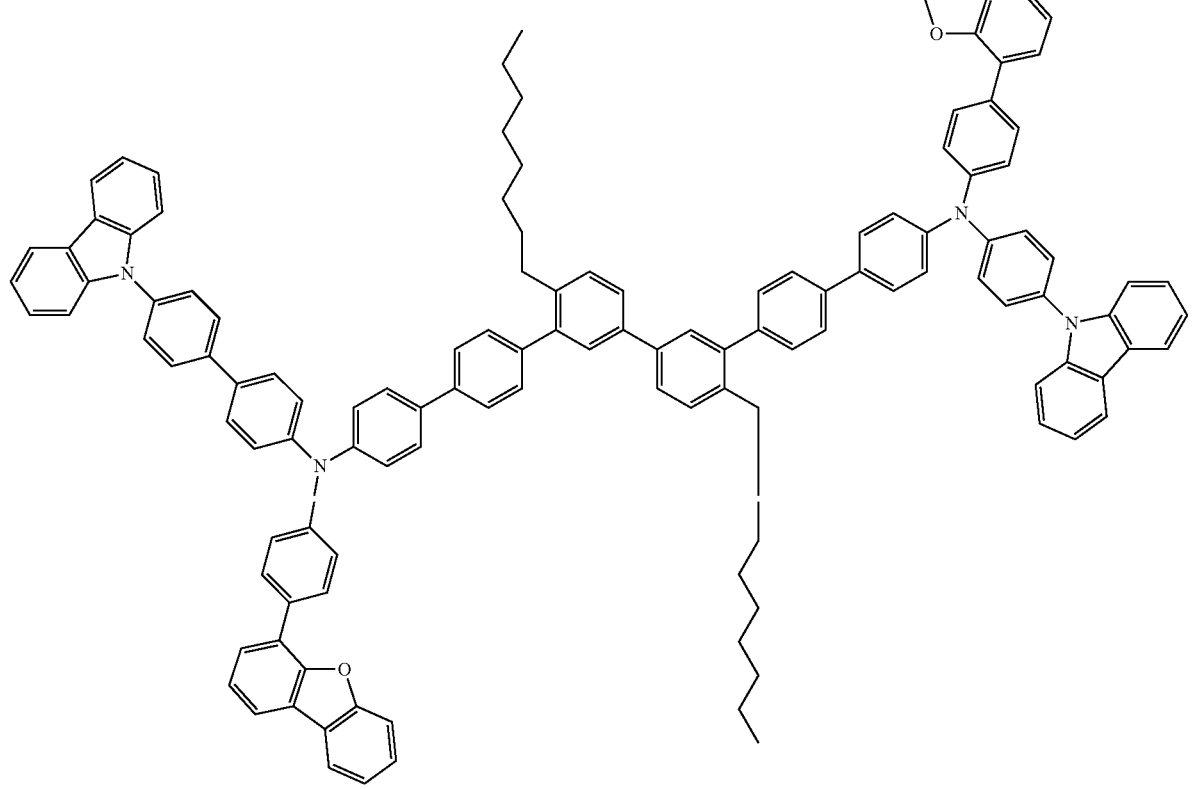

-continued
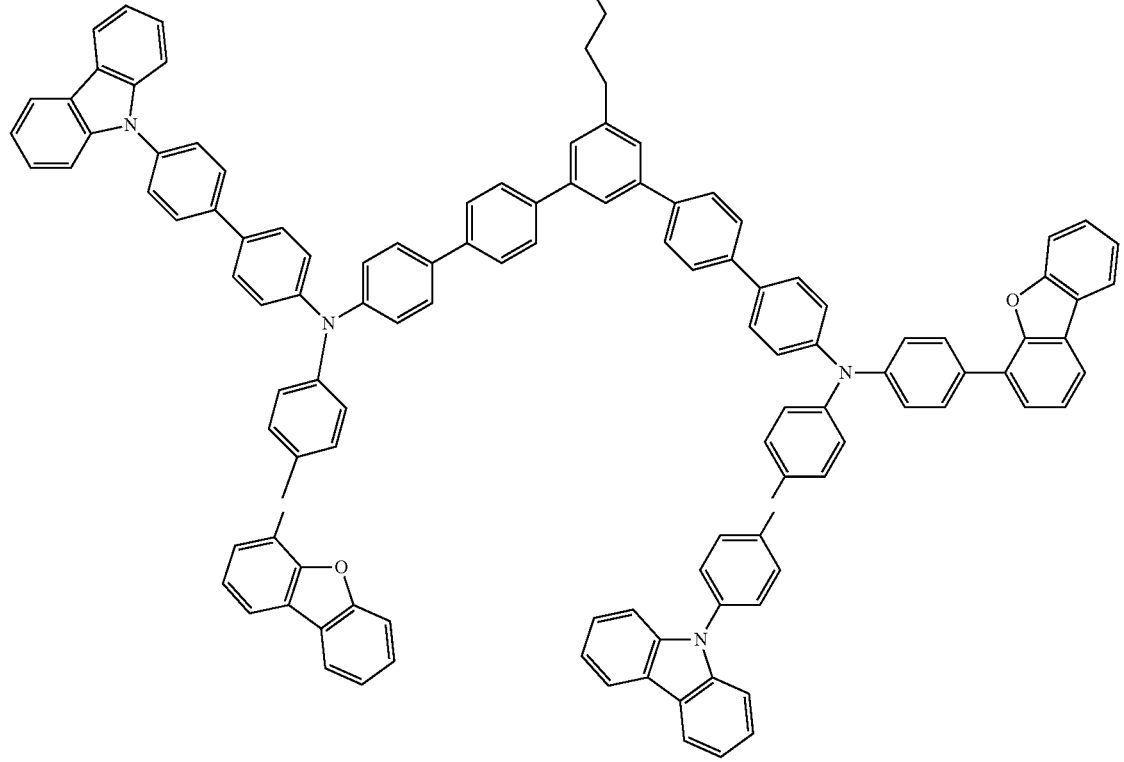
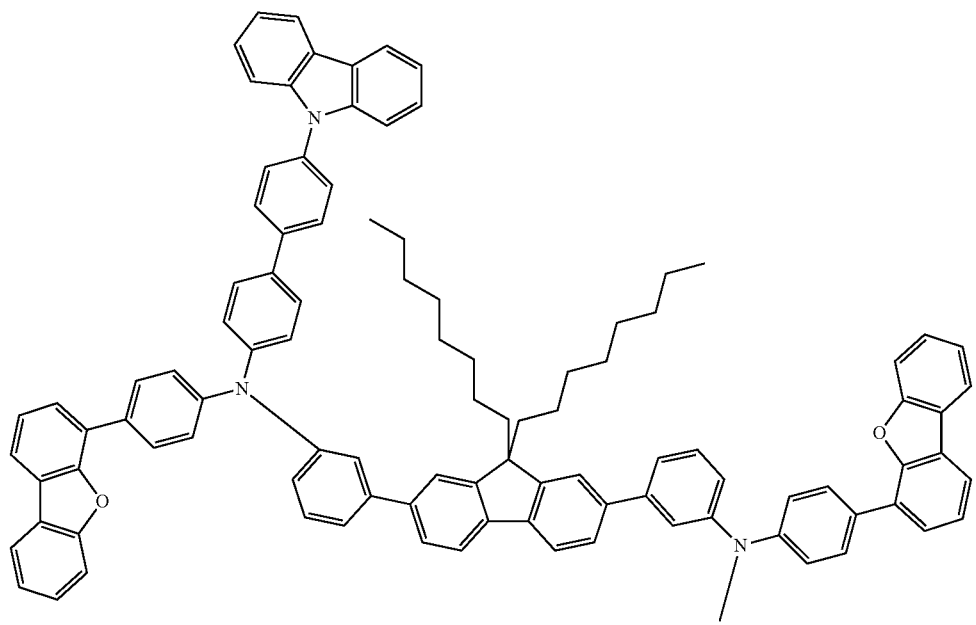

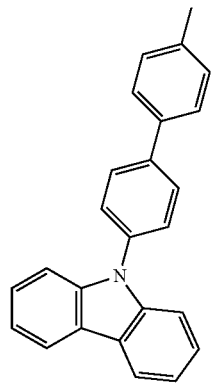
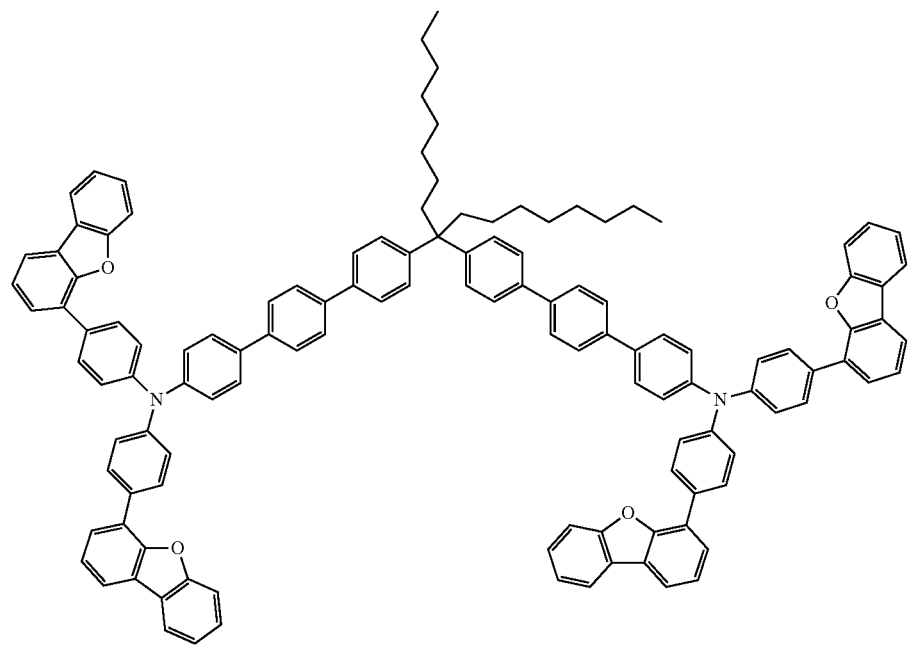
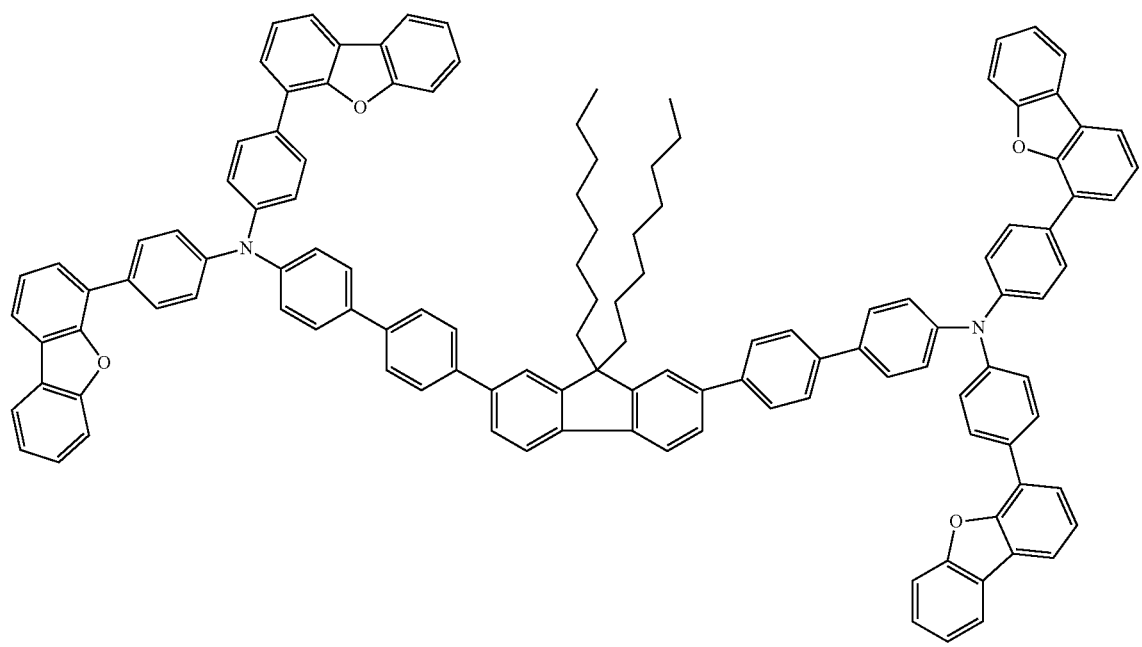

91
92
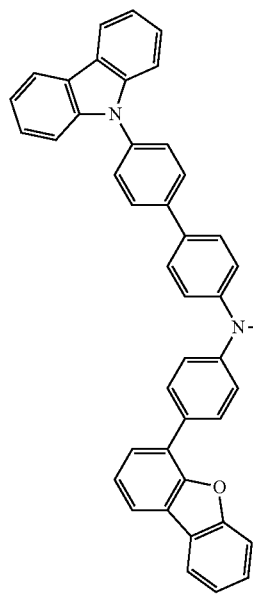
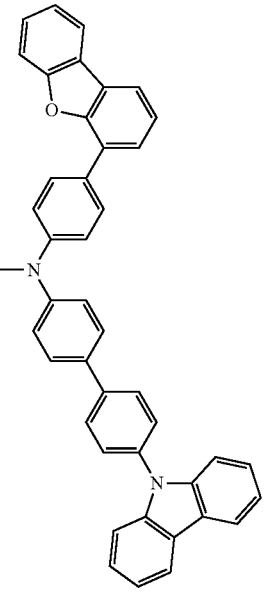
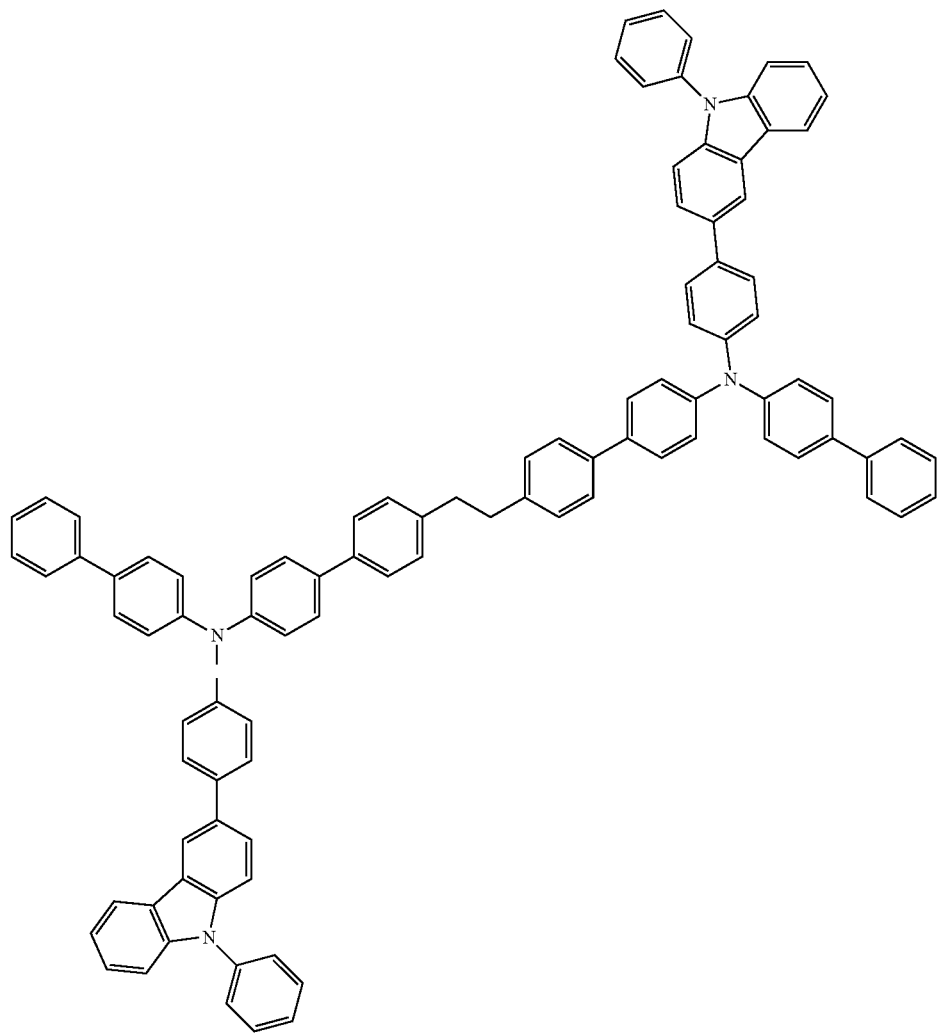

-continued
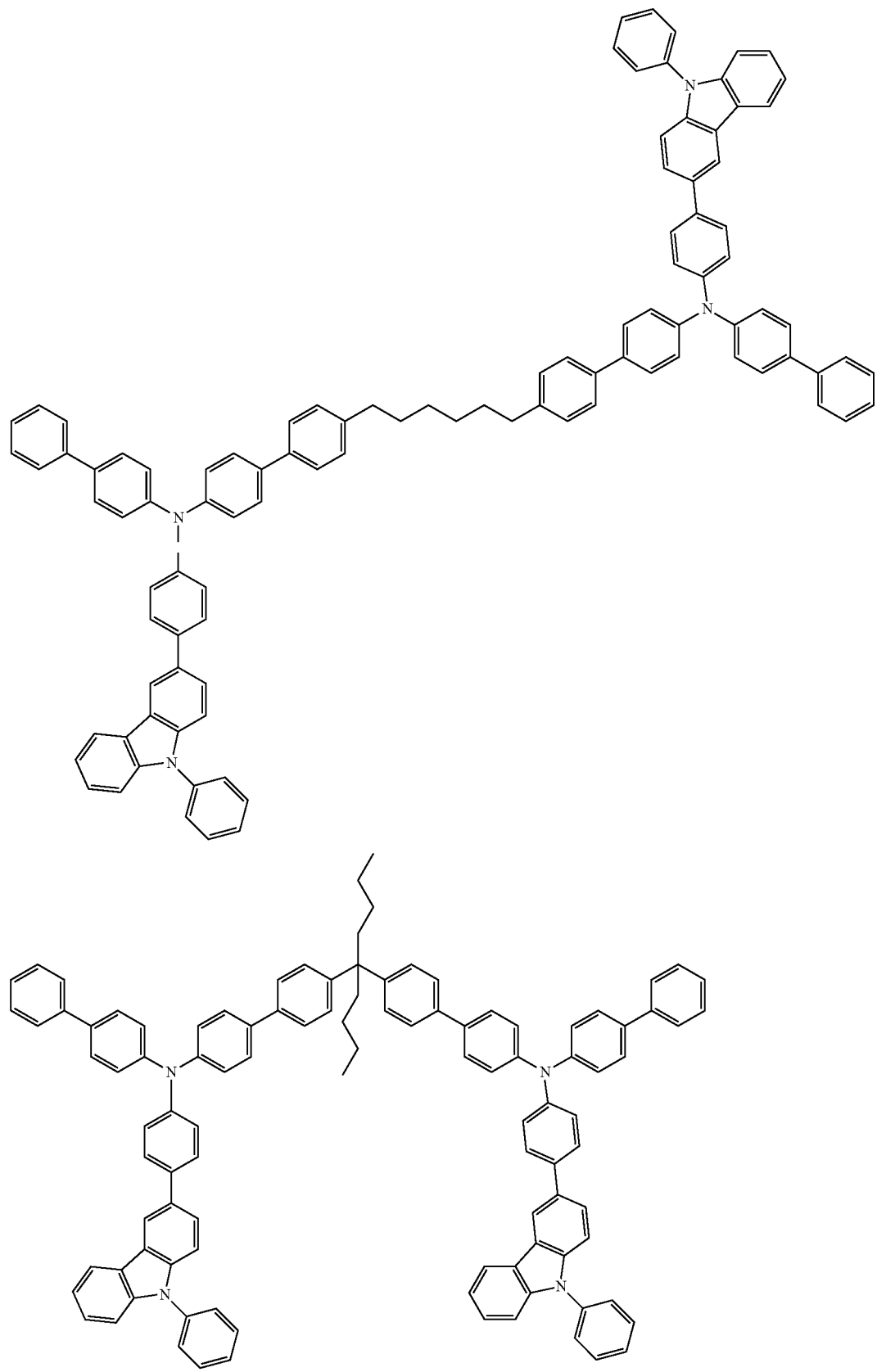 [SMILES: c1ccc(-c2ccc(N(c3ccc(-c4ccc(CCCCCCc5ccc(-c6ccc(N(c7ccc(-c8ccccc8)cc7)c7ccc(-c8ccc9c(c8)c8ccccc8n9-c8ccccc8)cc7)cc6)cc5)cc4)cc3)c3ccc(-c4ccc5c(c4)c4ccccc4n5-c4ccccc4)cc3)cc2)cc1 ; CCCCC(CCCC)(c1ccc(-c2ccc(N(c3ccc(-c4ccccc4)cc3)c3ccc(-c4ccc5c(c4)c4ccccc4n5-c4ccccc4)cc3)cc2)cc1)c1ccc(-c2ccc(N(c3ccc(-c4ccccc4)cc3)c3ccc(-c4ccc5c(c4)c4ccccc4n5-c4ccccc4)cc3)cc2)cc1]

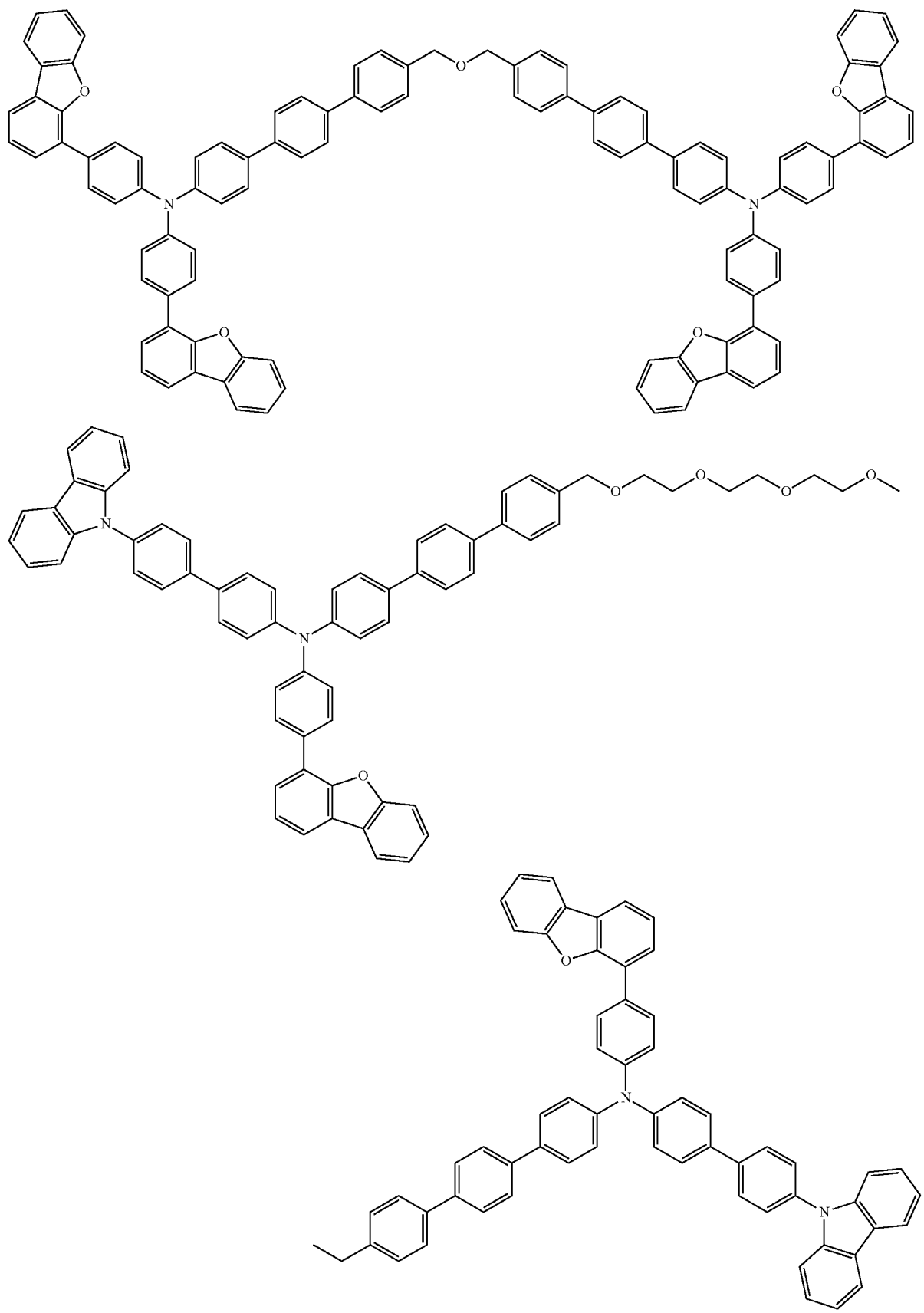

-continued
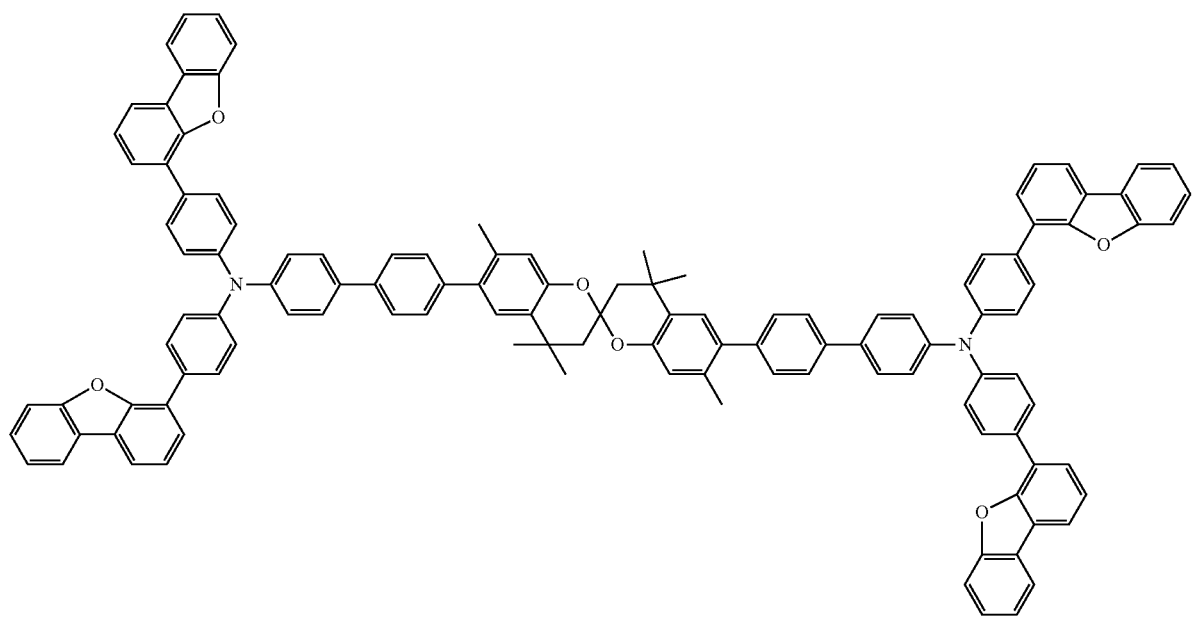
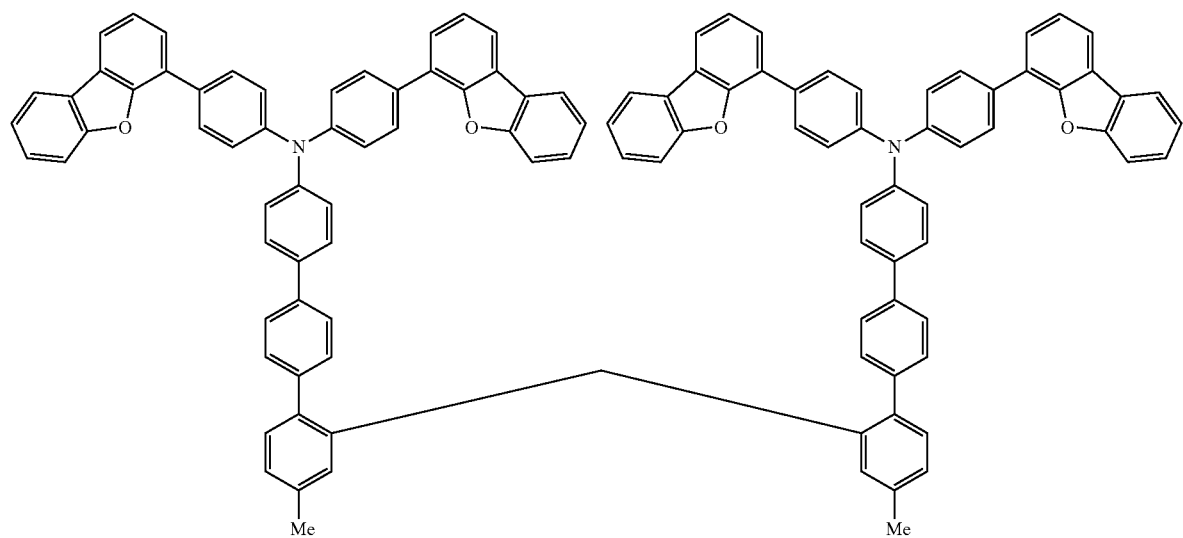

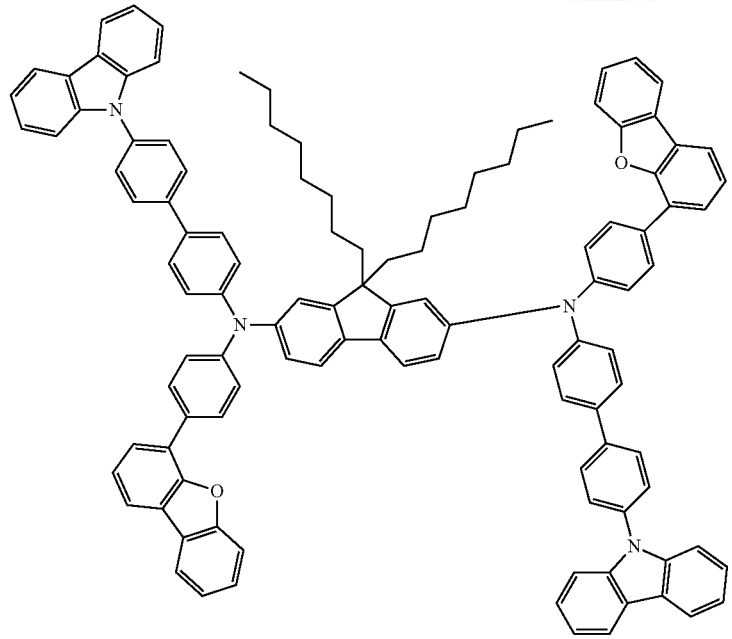 [SMILES: CCCCCCCCC1(CCCCCCCC)c2cc(N(c3ccc(-c4ccc(-n5c6ccccc6c6ccccc65)cc4)cc3)c3ccc(-c4cccc5c4oc4ccccc45)cc3)ccc2-c2ccc(N(c3ccc(-c4ccc(-n5c6ccccc6c6ccccc65)cc4)cc3)c3ccc(-c4cccc5c4oc4ccccc45)cc3)cc21]

The aromatic amine derivative of the invention can be suitably used for an organic device material, a hole-injecting and -transporting material and an organic electroluminescence device material as below. The organic device, in particular organic EL device obtained by using the aromatic amine derivative of the invention, has excellent device performances such a long life and a high luminous efficiency. In addition, the organic EL device suffers only a small degree of deterioration even at a high-temperature driving which is practical for displays and lighting application, thereby to provide a practical organic EL device.

Furthermore, a hole-injecting and -transporting layer can be formed uniformly by a coating method, whereby the device provided by the invention is suitable for reducing cost and growing in size of screen in displays and lighting application.

Here, examples of the organic device include an organic TFT, photoelectric conversion elements such an organic solar cell and an image sensor, in addition to an organic EL device.

The organic EL device can be used for a planar luminous body such as a flat panel display of a wall-hanging television, general or special lighting, a copier, a printer, a light resource of a backlight of a liquid crystal display, indicators or the like, an display panel, a beacon light and the like.

The aromatic amine derivative of the invention can be also used as a material for an electron photoreceptor.

The organic EL device of the invention comprises an anode, a cathode, and one or more organic thin film layers including at least an emitting layer between the anode and the cathode, in which at least one of the organic thin film layers comprises the aromatic amine derivative of the invention.

In the organic EL device of the invention, the organic thin film layers have at least one of a hole-transporting layer and a hole-injecting layer, and the at least one of a hole-transporting layer and a hole-injecting layer preferably comprises the aromatic amine derivative of the invention.

It is more preferable that the at least one of a hole-transporting layer and a hole-injecting layer comprise the aromatic amine derivative of the invention as a main component. Specifically, the hole-transporting layer or the hole-injecting layer contains the aromatic amine derivative of the invention preferably in an amount of 51 to 100 weight %.

By adding various cross-linkers (known cross-linkers disclosed in Chem. Mater. 2008, 20, 413-422, Chem. Mater. 2011, 23(3), 658-681 and etc., for example) to the aromatic amine derivative of the invention as other components, the hole-transporting layer or the hole-injecting layer may be subjected to an insoluble treatment using heat, light or the like.

If the organic EL device has at least one of a hole-transporting layer and hole-injecting layer, it is preferred that the at least one of a hole-transporting layer and a hole-injecting layer contain an acceptor material. In particular, it is preferred that the layer adjacent to the anode contain an acceptor material.

Due to the presence of an acceptor material, the hole density in a hole-injecting and -transporting layer and the hole mobility is increased, the driving voltage of an organic EL device obtained can be reduced and the carrier balance thereof can be improved, thereby prolonging the lifetime.

The acceptor material is preferably an organic compound having an electron-attracting substituent or an electron-deficient ring.

As the electron-attracting substituent, halogen, CN—, a carbonyl group, an aryl boron group and the like can be given, for example.

Examples of the electron-deficient ring include, but not limited to, compounds selected from the group consisting of 2-pyridyl, 3-pyridyl, 4-pyridyl, 2-quinolyl, 3-quinolyl, 4-quinolyl, 2-imidazole, 4-imidazole, 3-pyrazole, 4-pyrazole, pyridazine, pyrimidine, pyrazine, cinnoline, phthalazine, quinazoline, quinoxaline, 3-(1,2,4-N)-triazolyl, 5-(1,2,4-N)-triazolyl, 5-tetrazolyl, 4-(1-O,3-N)-oxazole, 5-(1-O,3-N)-oxazole, 4-(1-S,3-N)-thiazole, 5-(1-S,3-N)-thiazole, 2-benzoxazole, 2-benzothiazole, 4-(1,2,3-N)-benzotriazole and benzimidazole, for example.

The above-mentioned acceptor material is preferably a quinoid derivative.

As the quinoid derivative, compounds represented by the following formulas (1a) to (1i) can be given, more preferably compounds represented by the formula (1a) or (1b).

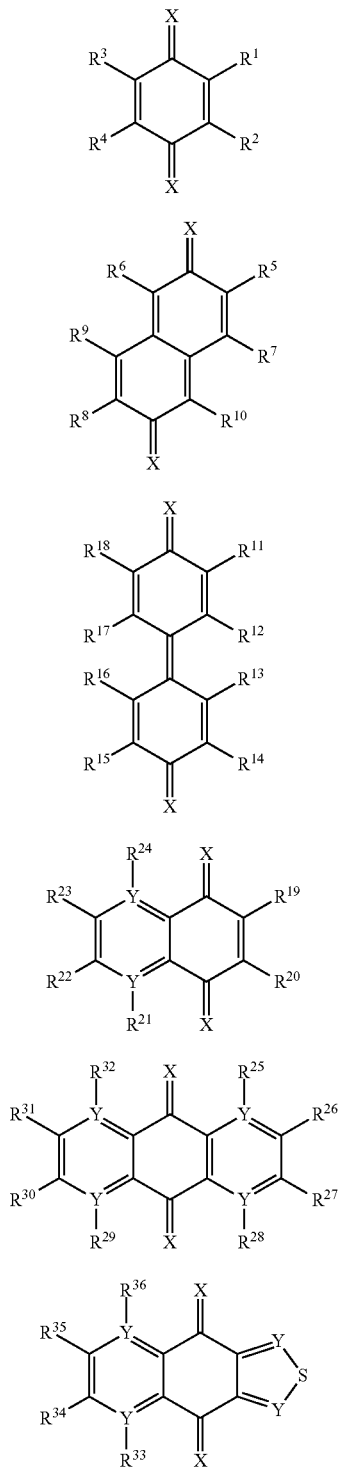

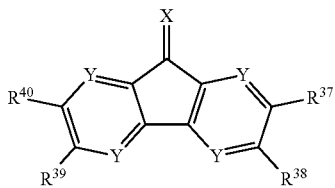

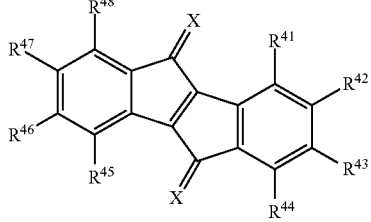

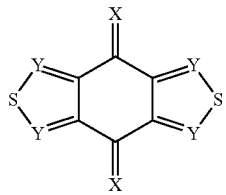

In the formulas (1a) to (1i), $R^1$ to $R^{48}$ are independently hydrogen, halogen, a fluoroalkyl group, a cyano group, an alkoxy group, an alkyl group or an aryl group, with hydrogen or a cyano group being preferable.

In the formulas (1a) to (1i), X is an electron-attracting group, and composed of any of structures represented by the following formulas (j) to (p), with the structures represented by (j), (k) and (l) being preferable:

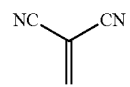

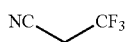

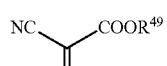

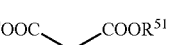

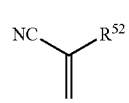

In the formulas, $R^{49}$ to $R^{52}$ are independently hydrogen, a fluoroalkyl group, an alkyl group, an aryl group or a heterocyclic group, and $R^{50}$ and $R^{51}$ may form a ring.

In the formulas (1a) to (1i), Y is —N= or —CH=.

As the halogen represented by $R^1$ to $R^{48}$, fluorine and chlorine are preferable.

As the fluoroalkyl group represented by $R^1$ to $R^{48}$, a trifluoromethyl group and a pentafluoroethyl group are preferable.

As the alkoxyl group represented by $R^1$ to $R^{48}$, a methoxy group, an ethoxy group, an iso-propoxy group, and a tert-butoxy group are preferable.

As the alkyl group represented by $R^1$ to $R^{48}$, a methyl group, an ethyl group, a propyl group, an iso-propyl group, a tert-butyl group and a cyclohexyl group are preferable.

As the aryl group represented by $R^1$ to $R^{48}$, a phenyl group and a naphthyl group are preferable.

The fluoroaklyl group, the alkyl group and the aryl group represented by $R^{49}$ to $R^{52}$ are the same as those of $R^1$ to $R^{48}$.

The heterocyclic ring of $R^{49}$ to $R^{52}$ is preferably a substituent represented by the following formulas:

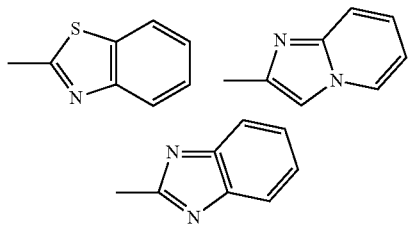

When $R^{50}$ and $R^{51}$ form a ring, X is preferably a substituent represented by the following formula:

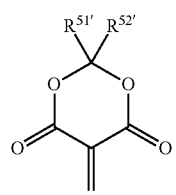

In the formula, $R^{51'}$ and $R^{52'}$ are independently a methyl group, an ethyl group, a propyl group or a tert-butyl group.

Specific examples of the quinoid derivative include the following compounds:

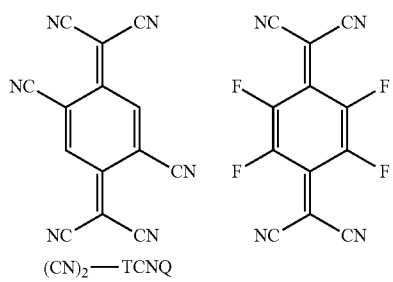

(CN)₂—TCNQ

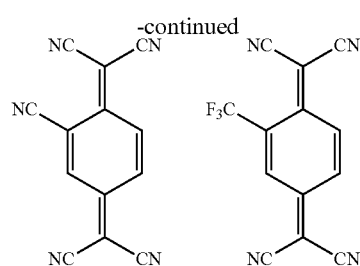

It is also preferred that a hexaazatriphenylene derivative represented by the following formula (A) be used as the above-mentioned acceptor material:

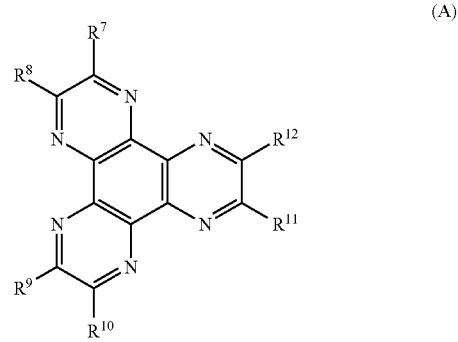

(A)

wherein $R^7$ to $R^{12}$ are independently a cyano group, —CONH₂, a carboxyl group or —COOR¹³ wherein $R^{13}$ is an alkyl group having 1 to 20 carbon atoms, and $R^7$ and $R^8$, $R^9$ and $R^{10}$, or $R^{11}$ and $R^{12}$ may be bonded to each other to form a group represented by —CO—O—CO—.

As the alkyl group of $R^{13}$, a methyl group, an ethyl group, an n-propyl group, an iso-propyl group, an n-butyl group, an iso-butyl group, a tert-butyl group, a cyclopentyl group, a cyclohexyl group and the like can be given.

Specific examples of the hexaazatriphenylene derivative include the following compound:

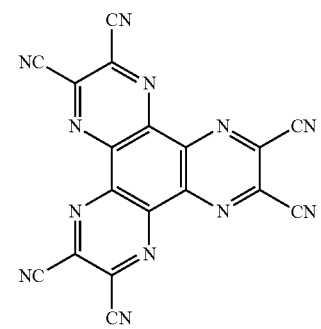 [SMILES: N#Cc1nc2c3nc(C#N)c(C#N)nc3c3nc(C#N)c(C#N)nc3c2nc1C#N]

It is preferred that the organic EL device of the invention emit blue light. Since the aromatic amine derivative of the invention has a wide band gap, use of the derivative of the invention in an organic thin film layer allows the organic EL device emitting blue light to have a longer lifetime even if the device is driven at a practically high luminance and under high temperatures.

Representative examples of the configuration of the organic EL device of the invention are given below.

(1) Anode/emitting layer/cathode
(2) Anode/hole-injecting layer/emitting layer/cathode
(3) Anode/emitting layer/electron-injecting layer/cathode
(4) Anode/hole-injecting layer/emitting layer/electron-injecting layer/cathode
(5) Anode/organic semiconductor layer/emitting layer/cathode
(6) Anode/organic semiconductor layer/electron-blocking layer/emitting layer/cathode
(7) Anode/organic semiconductor layer/emitting layer/adhesion-improving layer/cathode
(8) Anode/hole-injecting layer/hole-transporting layer/emitting layer/electron-injecting layer/cathode
(9) Anode/insulating layer/emitting layer/insulating layer/cathode
(10) Anode/inorganic semiconductor layer/insulating layer/emitting layer/insulating layer/cathode
(11) Anode/organic semiconductor layer/insulating layer/emitting layer/insulating layer/cathode
(12) Anode/insulating layer/hole-injecting layer/hole-transporting layer/emitting layer/insulating layer/cathode
(13) Anode/insulating layer/hole-injecting layer/hole-transporting layer/emitting layer/electron-injecting layer/cathode Of these, usually, configuration (8) is preferably used. However, the device configuration of the invention is not limited to these.

<Transparent Substrate>

The organic EL device of the invention is produced by stacking a plurality of layers having each of the above-mentioned layer configurations on a transparent substrate. The transparent substrate is a substrate for supporting the organic EL device, and is preferably a flat and smooth substrate having a transmittance of 50% or more in the visible range of 400 to 700 nm.

Specific examples thereof include a glass palate and a polymer plate. As the glass plate, particularly, soda-lime glass, barium/strontium-containing glass, lead grass, aluminosilicate glass, borosilicate glass, barium borosilicate glass, quartz and the like can be given. As the polymer plate, polycarbonate, acrylic polymer, polyethylene terephthalate, polyethersulfone, polysulfone and the like can be given.

<Anode>

For the conductive material used in the anode of the organic EL devise of the invention, a material having a work function greater than 4 eV is suitable, and carbon, aluminum, vanadium, iron, cobalt, nickel, tungsten, silver, gold, platinum, palladium and the like and alloys thereof, metal oxides such as tin oxide or indium oxide used in ITO substrates or NESA substrates, and organic conductive resins such as polythiophen and polypyrrole can be used.

<Cathode>

For the conductive material used in the cathode, a material having a work function smaller than 4 eV is suitable, and magnesium, calcium, tin, lead, titanium, yttrium, lithium, ruthenium, manganese, aluminum, lithium fluoride and the like, and alloys thereof are used, though not limited thereto. Representative examples of the alloy include, but not limited to, a magnesium/silver alloy, a magnesium/indium alloy and a lithium/aluminum alloy. The ratio of the alloy is controlled by the temperature of an evaporation resource, atmosphere, the degree of vacuum and the like and is selected appropriately. If necessary, the anode and the cathode can be composed of two or more layers.

This cathode can be produced by forming the above-mentioned conductive substance into a thin film using a method such as deposition or sputtering.

Here, if emission from an emitting layer is outcoupled from the cathode, it is preferred that the transmittance relative to the emission from the cathode be larger than 10%.

In addition, the sheet resistance of the cathode is preferably several hundred $\Omega/\square$ or lower. The film thickness is usually 10 nm to 1 μm, preferably 50 to 200 nm.

<Insulating Layer>

In an organic EL device, pixel defects tend to occur due to leakage and short circuit since an electric field is impressed to super thin films. In order to prevent this problem, it is preferred that an insulating thin film layer be provided between a pair of electrodes.

As the material used in the insulating layer, for example, aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, vanadium oxide and the like can be given. A mixture or multilayer stack thereof can be used.

<Emitting Layer>

The emitting layer of the organic EL device has the following functions (1) to (3) in combination.

(1) Injection function: function of allowing injection of holes from the anode or hole-injecting layer and injection of electrons from the cathode or electron-injecting layer upon application of an electric field (2) Transporting function: function of moving injected carriers (electrons and holes) due to the force of an electric field (3) Emitting function: function of allowing electrons and holes to recombine therein to emit light Note that electrons and holes may be injected into the emitting layer with different degrees, or the transportation capabilities indicated by the mobility of holes and electrons may differ. It is preferable that the emitting layer move either electrons or holes.

In the above-mentioned plural layers, if necessary, the aromatic amine derivative of the invention can be used. In addition thereto, known emitting materials, doping materials, hole-injecting materials and electron-injecting materials can be used. The organic EL device wherein the organic thin film layer is composed of plural layers can prevent the decrease of luminance and lifetime by quenching. If necessary, an emitting material, a doping material, a hole-injecting material and an electron injecting material can be used in combination with the aromatic amine derivative of the invention. Furthermore, by adding of a doping material, the luminance and luminous efficiency can be improved, and emission of red light or blue light can be obtained. Moreover, the hole-injecting layer, the emitting layer and the electron-injecting layer may independently be composed of two or more layers. Then, in the case where the hole-injecting layer is composed of two or more layers, the layer into which holes are injected from the electrode is referred to as a hole-injecting layer, and the layer which receives holes from the hole-injecting layer and transports the holes to the emitting layer is referred to as a hole-transporting layer. Similarly, in the case where the electron-injecting layer is composed of two or more layers, the layer into which electrons are injected from the electrode is referred to as an electron-injecting layer, and the layer which receives electrons from the electron-injecting layer and transports the electrons to the emitting layer is referred to as an electron-transporting layer. Each layer of these is selected and used based on each factor such as the energy level of a material, heat resistance, adhesion property to an organic layer or a metal electrode or the like.

Examples of the host material or the doping material which can be used with the aromatic amine derivative of the invention include, but are not limited to, fused polycyclic aromatic compounds such as naphthalene, phenanthrene, rubrene, anthracene, tetracene, pyrene, perylene, chrysene, decacyclene, coronene, tetraphenylcyclopentadiene, pentaphenylcyclopentadiene, fluorene, spirofluorene, 9,10-diphenylanthracene, 9,10-bis(phenylethynyl)anthracene and 1,4-bis(9'-ethynylanthracenyl)benzene, and derivatives thereof; organic metal complexes such as tris(8-quinolinolato)aluminum and bis-(2-methyl-8-quinolinolato)-4-(phenylphenolinato)aluminum; triarylamine derivatives, styrylamine derivatives, stilbene derivatives, coumarin derivatives, pyrane derivatives, oxazon derivatives, benzothiazole derivatives, benzoxazole derivatives, benzimidazole derivatives, pyrazine derivatives, cinamic acid ester derivatives, diketopyrrolopyrrole derivatives, acridone derivatives, quinacridone derivatives and fluoranthene derivatives.

The hole-injecting and -transporting layer is a layer which helps holes inject into an emitting layer and transports the holes to the emitting zone, and has a large hole mobility and normally a small ionization energy of 5.6 eV or less. As the hole-injecting and -transporting layer, the material which can transport holes to an emitting layer at a lower electric field strength is preferable. Further preferable is a material having a hole mobility of at least $10^{-4}$ cm$^2$V·second at an impressed electric field of $10^4$ to $10^6$ V/cm, for example.

As described above, the aromatic amine derivative of the invention is particularly preferably used as a hole-injecting and -transporting layer.

When the aromatic amine derivative of the invention is used in a hole-transporting zone, the hole-injecting and/or -transporting layer may be formed of the hole-transporting material of the invention alone, or as a mixture with other materials.

There is no specific restriction imposed on the other materials to be mixed with the aromatic amine derivative of the invention to form a hole-injecting and -transporting layer, in so far as it has the above-mentioned preferable properties. As the other materials, any material can be selected and used from materials traditionally used as a charge-transporting material for holes in photoconductive materials and known materials used in a hole-injecting and -transporting layer of an organic EL device. In the invention, the material which has a hole-transporting ability and can be used in the hole-transporting zone is referred to as a hole-transporting material.

Specific examples of the materials for the hole-injecting and -transporting layer other than the aromatic amine derivative of the invention include, but not limited to, phthalocyanine derivatives, naphthalocyanine derivatives, porphyrin derivatives, oxazole, oxadiazole, triazole, imidazole, imidazolone, imidazolethione, pyrazoline, pyrazolone, tetrahydroimidazole, oxazole, oxadiazole, hydrazone, acylhydrazone, polyarylalkane, stilbene, butadiene, benzidine-type triphenyl amine, styrylamine-type triphenylamine, diamine-type triphenylamine and the like, and derivatives thereof, and polymer materials such as polyvinylcarbazoles, polysilanes and conductive polymers (polyaniline, polythiophene).

Of the hole-injecting materials usable in the organic EL device of the invention, more efficient hole-injecting materials are aromatic tertiary amine derivatives and phthalocyanine derivatives.

Examples of the aromatic tertiary amine derivative include, but not limited to, triphenylamine, tritolylamine, tolyldiphenylaimine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cyclohexane and the like, and oligomers or polymers having these aromatic tertiary amine skeletons.

Examples of the phthalocyanine (Pc) derivative include, but not limited to, phthalocyanine derivatives and naphthalocyanine derivatives such as H$_2$Pc, CuPc, CoPc, NiPc, ZnPc, PdPc, FePc, MnPc, ClAlPc, ClGaPc, ClInPc, ClSnPc, Cl$_2$SiPc, (HO)AlPc, (HO)GaPc, VOPc, TiOPc, MoOPc, and GaPc-O—GaPc. In the organic EL device of the invention, a layer containing these aromatic tertiary amine derivatives and/or phthalocyanine derivatives, for example, as the hole-transporting layer or the hole-injecting layer, is preferably provided between the emitting layer and the anode.

Next, the electron-injecting and -transporting layer will be described. The electron-injecting and -transporting layer is a layer which helps electrons injecting into the emitting layer and transports the electrons to the emitting zone, and has a large electron-mobility. The adhesion-improving layer is a layer formed of a material having an especially good adherability to the cathode among these electron-injecting layers.

It is known that in an organic EL device, due to reflection of emitted light at the electrode (in this case, cathode), emitting light outcoupled directly from an anode is interfered with emitting light outcoupled via reflection by the electrode. In order to utilize efficiently this interference effect, the film thickness of the electron-transporting layer is appropriately selected to be in the range of several nm to several μm. When the thickness is particularly large, in order to avoid an increase in voltage, it is preferred that the electron-mobility be at least $10^{-5}$ cm$^2$/Ns or more at an impressed electric field of $10^4$ to $10^6$ V/cm.

Specific examples of the material used in the electron-injecting layer include, but not limited to, fluorenone, anthraquinodimethane, diphenoquinone, thiopyranedioxide, oxazole, oxadiazole, triazole, imidazole, perylenetetracarbonic acid, fluorenylidene methane, anthraquinodimethane, anthrone and the like, and derivatives thereof. It is also possible to add an electron-accepting substance to the hole-injecting material, and an electron-donating substance to the electron-injecting material, thereby sensitizing the materials.

In the organic EL device of the invention, more efficient electron-injecting materials are metal complex compounds and nitrogen-containing five-membered ring derivatives.

Examples of the metal complex compound include, but not limited to, 8-hydroxyquinolinatolithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum and bis(2-methyl-8-quinolinato)(2-naphtholato)gallium.

As the nitrogen-containing five-membered ring derivative, for example, oxazole, thiazole, oxadiazole, thiadiazole and triazole derivatives are preferable. Specific examples thereof include, but not limited to, 2,5-bis(1-phenyl)-1,3,4- oxazole, dimethyl POPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis (1-naphthyl)-1,3,4-thiadiazole, 1,4-bis[2-(5-phenylthiadiazolyl)]benzene, 2-(4'-tert-butylphenyl)-5-(4"-biphenyl)-1,3, 4-triazole, 2,5-bis(1-naphthyl)-1,3,4-triazole and 1,4-bis[2-(5-phenyltriazolyl)]benzene.

In the organic EL device of the invention, the emitting layer may contain at least one of an emitting material, a doping material, a hole-injecting material and an electron-injecting material with the aromatic amine derivative of the invention. In order to improve the stability against temperature, humidity, atmosphere or the like of the organic EL device obtained according to the invention, a protective layer can be provided on the surface of the device, or it is possible to protect the entire device with silicone oil, resins or the like.

In the organic EL device of the invention, for efficient emission, it is preferred that at least one surface of the device be sufficient transparent in the range of emission wavelength of the device. In addition, the substrate is desirably transparent. The transparent electrode is formed of the above-mentioned conductive material, thereby to ensure predetermined transparency by a method such as deposition, sputtering or the like. The electrode on the emitting surface has preferably a light transmittance of 10% or more. The substrate is not limited in so far as it has mechanical and thermal strength and transparency. As the substrate, a glass substrate and a transparent resin film can be given. Examples of the transparent resin film include polyethylene, ethylene-vinyl acetate copolymer, ethylene-vinyl alcohol copolymer, polypropylene, polystyrene, polymethyl methacrylate, polyvinyl chloride, polyvinyl alcohol, polyvinyl butyral, nylon, polyetheretherketone, polysulfone, polyethersulfone, tetrafluoroethylene-perfluoroalkylvinylether copolymer, polyvinyl fluoride, tetrafluoroethylene-ethylene copolymer, tetrafluoroethylene-hexafluoropropylene copolymer, polychlorotrifluoroethylene, polyvinylidene fluoride, polyester, polycarbonate, polyurethane, polyimide, polyetherimide, polyimide and polypropylene.

Each layer of the organic EL device of the invention can be formed by applying known methods, for example, a dry-type film-forming process such as vacuum deposition, sputtering or plasma ion-plating, or a wet-type film-forming process such as spin coating, dipping or flow-coating. The film thickness is not particularly limited, but is required to be set to an appropriate value. If the film thickness is too large, a large applied voltage may be required in order to obtain a certain light output, thereby resulting in a decreased efficiency. If the film thickness is too small, pinholes and the like may be generated, whereby sufficient luminance cannot be obtained even if an electric field is impressed. The normal film thickness is suitably in the range of 5 nm to 10 µm, with the range of 10 nm to 0.2 µm being more preferable.

As the method for forming the layer containing the aromatic amine derivative of the invention (particularly hole-injecting and -transporting layer), a method for forming a solution of the organic amine derivative into a film can be given, for example. Examples of the film-forming method include spin-coating, casting, micro gravure coating, gravure coating, bar coating, roll coating, slit coating, wire-bar coating, dip coating, spray coating, the screen printing method, the flexographic printing method, the offset printing method, the ink-jet printing method and the nozzle printing method. In the case of pattern formation, the screen printing method, the flexographic printing method, the offset printing method and the ink-jet printing method are preferable. Film formation by these methods can be conducted under conditions known to those skilled in the art, which will not be explained in detail.

After film formation, it is only necessary to dry the films obtained in a vacuum with heating (200° C. or lower) and to remove the solvent. Polymerization reaction by light or heating at high temperatures (200° C. or higher) is not required, thereby to suppress the performance degradation due to light or heating at high temperatures.

On the other hand, adding various cross-linkers (known cross-linkers disclosed in Chem. Matter. 2008, 20, 413-422, Chem. Matter. 2011, 23(3), 658-681 and etc., for example) can make a hole-transporting layer or a hole-injecting layer insoluble by using heat or light while suppressing the performance degradation as much as possible.

It suffices that the solution for film formation contain at least one of the aromatic amine derivatives of the invention. The solution may contain other hole-transporting materials, electron-transporting materials, emitting materials, acceptor materials, solvents and additives such as a stabilizer, in addition to the above-mentioned materials. The content of the aromatic amine derivative in the above-mentioned solution for film formation is preferably 20 to 100 weight % relative to the total weight of the composition excluding the solvent. It is more preferable that the content be 51 to 100 weight %, and the aromatic amine derivative be the main component of the composition excluding the solvent. The ratio of the solvent is preferably 1 to 99.9 weight % of the solution for film formation, with 80 to 99 weight % being more preferable.

The solution for film formation may contain an additive agent for adjusting the viscosity and/or the surface tension such as a thickener (a high-molecular-weight compound, a poor solvent for the aromatic amine derivative of the invention, etc.), a viscosity depressant (a low-molecular-weight compound, etc.) and a surfactant. Also, for improving the storage stability, the solution may contain an antioxidant, such as a phenolic antioxidant and a phosphorous antioxidant, which does not affect adversely the performance of the organic EL device.

Examples of the usable high-molecular-weight compound include insulating resins such as polystyrene, polycarbonate, polyarylate, polyester, polyamide, polyurethane, polysulfone, polymethylmethacrylate, polymethylacrylate and cellulose and copolymers thereof, and photoconductive resins such as poly-N-vinylcarbazole and polysilane, and conductive resins such as polythiophene and polypyrrole.

Examples of the solution for film-forming include chlorine solvents such as chloroform, methylene chloride, 1,2-dichloroethane, 1,1,2-trichloroethane, chlorobenzene and o-dichlorobenzene; ether-type solvents such as tetrahydrofuran, dioxane, dioxolane and anisole; aromatic hydrocarbon-type solvents such as toluene and xylene; aliphatic hydrocarbon-type solvents such as cyclohexane, methycyclohexane, n-pentane, n-hexane, n-heptane, n-octane, n-nonane and n-decane; ketone-type solvents such as acetone, methylethylketone, cyclohexanone, benzophenone and acetophenone; ester-type solvents such as ethyl acetate, butyl acetate, ethyl cellosolbe acetate, methyl benzoate and phenyl acetate; polyols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerine and 1,2-hexanediol, and derivatives thereof; alcohol-type solvents such as methanol, ethanol, propanol, isopropanol and cyclohexanol; sulfoxide-type solvents such as dimethylsulfoxide; and amide-type solvents such as N-methyl-2-pyrrolidone and N,N-dimethylorma-mide. These organic solvents can be used singly or in combination of 2 or more. Among these, in terms of solubility, uniformity of formed film, viscosity and the like, aromatic hydrocarbon-type solvents, ether-type solvents, aliphatic hydrocarbon-type solvents, ester-type solvents and ketone-type solvents are preferable. More preferable are toluene, xylene, ethylbenzene, diethylbenzene, trimethylbenzene, n-propylbenzene, isopropylbenzene, n-butylbenzene, isobutylbenzene, 5-butylbenzene, n-hexylbenzene, cyclohexylbenzene, 1-methylnaphthalene, tetraline, 1,3-dioxane, 1,4-dioxane, 1,3-dioxolane, anisole, ethoxybenzene, cyclohexane, bicyclohexyl, cyclohexenyl cyclohexanone, n-heptylcyclohexane, n-hexylcyclohexane, decaline, methyl benzoate, cyclohexanone, 2-propylcyclohexanone, 2-heptanone, 3-heptanone, 4-heptanone, 2-octanone, 2-nonanone, 2-decanone, dicyclohexylketone, acetophenone and benzophenone.

<Method for Producing an Organic EL Device>

An organic EL device can be produced by forming an anode, an emitting layer, if needed, a hole-injecting and -transporting layer, and, if needed, an electron-injecting and -transporting layer, and further a cathode by using the various materials and layer-forming methods exemplified above. Alternatively, an organic EL device can be produced in the reverse order to the above one, i.e. from a cathode to an anode.

EXAMPLES

The invention will be explained in more detail below with reference to the following Examples which should not be construed as limiting the scope of the invention.

Synthesis Example 1

Synthesis of Intermediate 1

Under a stream of argon, 47 g of 4-bromobiphenyl, 23 g of iodine, 9.4 g of periodic acid dehydrate, 42 ml of water, 360 ml of acetic acid and 11 ml of sulfuric acid were placed in a 1000 ml three-necked flask, stirred at 65° C. for 30 minutes, and reacted at 90° C. for 6 hours. The reactant was poured into iced water and filtrated. The resulting matter was washed with water and then methanol to obtain 67 g of white powder.

As a result of analysis of the white powder obtained using field desorption mass spectrometry (hereinafter referred to as FD-MS), the main peaks of m/z=358, 360 were obtained relative to $C_{12}H_8BrI=359$. Therefore, the white powder was identified as Intermediate 1.

Synthesis Example 2

Synthesis of Intermediate 2

The reaction was conducted in the same manner as in Synthesis Example 1 except that 2-bromo-9,9-dimethylfluorene was used instead of 4-bromobiphenyl to obtain 61 g of white powder.

The white powder obtained was identified as Intermediate 2 by the FD-MS analysis.

Synthesis Example 3

Synthesis of Intermediate 3

Under argon atmosphere, 2 ml of trans-1,2-cyclohexanediamine and 300 ml of 1,4-dioxane were added to 28.3 g of 4-iodobromobenzene, 16.7 g of carbazole, 0.2 g of copper iodide (CuI) and 42.4 g of tripotassium phosphate. The resulting mixture was stirred at 100° C. for 20 hours.

After completion of the reaction, 300 ml of water was added to the resultant and then separated to remove the aqueous layer. The organic layer was dried with sodium sulfate and then concentrated. The residue was purified by silica-gel column chromatography to obtain 18.3 g of white crystals.

The white crystals obtained were identified as Intermediate 3 by the FD-MS analysis.

Synthesis Example 4

Synthesis of Intermediate 4

The reaction was conducted in the same manner as in Synthesis Example 3 except that 36 g of Intermediate 1 was used instead of 4-iodobromobenzene to obtain 23.1 g of white powder.

The white powder obtained was identified as Intermediate 4 by the FD-MS analysis.

Synthesis Example 5

Synthesis of Intermediate 5

The reaction was conducted in the same manner as in Synthesis Example 3 except that 40 g of Intermediate 2 was used instead of 4-iodobromobenzene to obtain 25.4 g of white powder.

The white powder obtained was identified as Intermediate 5 by the FD-MS analysis.

Synthesis Example 6

Synthesis of Intermediate 6

Under argon atmosphere, 300 ml of toluene and 150 ml of a 2M aqueous solution of sodium carbonate were added to 28.3 g of 4-iodobromobenzene, 22.3 g of dibenzofuran-4-boronic acid and 2.31 g of tetrakis(triphenylphosphine) palladium(0). The resulting mixture was heated under reflux for 10 hours.

Immediately after the reaction, the resultant was filtered, and then the aqueous layer was removed. The organic layer was dried with sodium sulfate and then concentrated. The residue was purified by silica-gel column chromatography to obtain 26.2 g of white crystals.

The white crystals obtained were identified as Intermediate 6 by the FD-MS analysis.

Synthesis Example 7

Synthesis of Intermediate 7

Under a stream of argon, 58 g of 1-acetamidenaphthalene, 44 g of Intermediate 5, 54 g of potassium carbonate, 1.3 g of copper powder and 200 ml of decaline were placed and reacted at 190° C. for 4 days. After the reaction, the reactant was cooled. 200 ml of toluene was added thereto, and an insoluble matter was filtered off. The matter which was filtered off was dissolved in 450 ml of chloroform and an insoluble matter was removed, followed by an active carbon treatment and concentration. 300 ml of acetone was added thereto, and 27 g of precipitated crystals were filtered off.

The crystals obtained were identified as Intermediate 7 by the FD-MS analysis.

Synthesis Example 8

Synthesis of Intermediate 8

Under a stream of argon, Intermediate 7 (27 g) was suspended in 500 ml of ethylene glycol and 5 ml of water. After adding 21 g of an 85% aqueous solution of potassium hydroxide to the suspension, the resulting mixture was reacted at 120° C. for 8 hours. After the reaction, the reaction liquid was poured into 1 L of water. Precipitated crystals were filtered off and washed with water and ethanol. The crystals obtained were dissolved in 300 ml of tetrahydrofuran while heating, subjected to an active carbon treatment and then concentrated. Acetone was added to the resulting matter to precipitate crystals. The precipitated crystals were filtered off to obtain 21 g of white powder.

The white powder obtained was identified as Intermediate 8 by the FD-MS analysis.

Synthesis Example 9

Synthesis of Intermediate 9

The reaction was conducted in the same manner as in Synthesis Example 7 except that acetamide was used instead of 1-acetamidenaphthalene and Intermediate 6 was used instead of Intermediate 5 to obtain 17 g of white powder.

The white powder obtained was identified as Intermediate 9 by the FD-MS analysis.

Synthesis Example 10

Synthesis of Intermediate 10

The reaction was conducted in the same manner as in Synthesis Example 7 except that Intermediate 9 was used instead of 1-acetamidenaphthalene and Intermediate 4 was used instead of Intermediate 5 to obtain 16.3 g of white powder.

The white powder obtained was identified as Intermediate 10 by the FD-MS analysis.

Synthesis Example 11

Synthesis of Intermediate 11

The reaction was conducted in the same manner as in Synthesis Example 8 except that Intermediate 10 was used instead of Intermediate 7 to obtain 15 g of white powder.

The white powder obtained was identified as Intermediate 11 by the FD-MS analysis.

Synthesis Example 12

Synthesis of Intermediate 12

The reaction was conducted in the same manner as in Synthesis Example 7 except that Intermediate 9 was used instead of 1-acetamidenaphthalene and Intermediate 3 was used instead of Intermediate 5 to obtain 28.5 g of white powder.

The white powder obtained was identified as Intermediate 12 by the FD-MS analysis.

Synthesis Example 13

Synthesis of Intermediate 13

The reaction was conducted in the same manner as in Synthesis Example 8 except that Intermediate 12 was used instead of Intermediate 7 to obtain 26.8 g of white powder.

The white powder obtained was identified as Intermediate 13 by the FD-MS analysis.

Synthesis Example 14

Synthesis of Intermediate 14

The reaction was conducted in the same manner as in Synthesis Example 7 except that Intermediate 9 was used instead of 1-acetamidenaphthalene and Intermediate 6 was used instead of Intermediate 5 to obtain 29.5 g of white powder.

The white powder obtained was identified as Intermediate 14 by the FD-MS analysis.

Synthesis Example 15

Synthesis of Intermediate 15

The reaction was conducted in the same manner as in Synthesis Example 8 except that Intermediate 14 was used instead of Intermediate 7 to obtain 26.7 g of white powder.

The white powder obtained was identified as Intermediate 15 by the FD-MS analysis.

Synthesis Example 16

Synthesis of Intermediate 16

The reaction was conducted in the same manner as in Synthesis Example 6 except that Intermediate 2 was used instead of 4-iodobromobenzene to obtain 35.7 g of white powder.

The white powder obtained was identified as Intermediate 16 by the FD-MS analysis.

Synthesis Example 17

Synthesis of Intermediate 17

The reaction was conducted in the same manner as in Synthesis Example 7 except that acetamide was used instead of 1-acetamidenaphthalene and Intermediate 16 was used instead of Intermediate 5 to obtain 32.5 g of white powder.

The white powder obtained was identified as Intermediate 17 by the FD-MS analysis.

Synthesis Example 18

Synthesis of Intermediate 18

The reaction was conducted in the same manner as in Synthesis Example 8 except that Intermediate 17 was used instead of Intermediate 7 to obtain 30.7 g of white powder.

The white powder obtained was identified as Intermediate 18 by the FD-MS analysis.

Synthesis Example 19

Synthesis of Intermediate 19

5.90 ml of sulfuric acid and 75 ml of ethanol were added to 17.7 g of 9-phenylcarbazole, 6.03 g of potassium iodide and 7.78 g of potassium iodate, and reacted at 75° C. for 2 hours.

After cooling, clean water and ethyl acetate were added, followed by separation and extraction. Subsequently, the organic layer was washed with sodium bicarbonate water and clean water and concentrated. The crude product obtained was purified by silica-gel chromatography (toluene), and the solids obtained were dried under reduced pressure to obtain 21.8 g of white solids.

The white solids obtained were identified as Intermediate 19 by the FD-MS analysis.

Synthesis Example 20

Synthesis of Intermediate 20

Under a stream of argon, dehydrated toluene and dehydrated ether were added to 13.1 g of Intermediate 19, and the mixture was cooled to −45° C. 25 ml of a hexane solution of n-butyllithium (1.58M) was added dropwise to the mixture. The resulting mixture was heated to −5° C. over 1 hour while stirring. The mixture was cooled to −45° C. again, and 25 ml of boronic acid triisopropyl ester was added dropwise slowly thereto, followed by reaction for 2 hours.

After the resultant was returned to room temperature, a 10% solution of dilute hydrochloric acid was added thereto and stirred to extract an organic layer. The organic layer was washed with saturated saline, and then dried with anhydrous magnesium sulfate. After filtration, concentration was conducted. The solids thus obtained were purified by silica-gel chromatography (toluene). The solids obtained were washed with n-hexane and dried under reduced pressure to obtain 7.10 g of solids.

The solids obtained were identified as Intermediate 20 by the FD-MS analysis.

Synthesis Example 21

Synthesis of Intermediate 21

Under argon atmosphere, 300 ml of toluene and 150 ml of a 2M aqueous solution of sodium carbonate were added to 28.3 g of 4-iodobromobenzene, 30.1 g of Intermediate 20 and 2.31 g of tetrakis(triphenylphosphine)palladium(0). The resulting mixture was heated under reflux for 10 hours.

Immediately after the reaction, the resultant was filtered, and then the aqueous layer was removed. The organic layer was dried with sodium sulfate and then concentrated. The residue was purified by silica-gel column chromatography to obtain 20.2 g of white crystals.

The white crystals obtained were identified as Intermediate 21 by the FD-MS analysis.

Synthesis Example 22

Synthesis of Intermediate 22

The reaction was conducted in the same manner as in Synthesis Example 7 except that acetamide was used instead of 1-acetamidenaphthalene and Intermediate 21 was used instead of Intermediate 5 to obtain 25.4 g of white powder.

The white powder obtained was identified as Intermediate 22 by the FD-MS analysis.

Synthesis Example 23

Synthesis of Intermediate 23

The reaction was conducted in the same manner as in Synthesis Example 8 except that Intermediate 22 was used instead of Intermediate 7 to obtain 22.7 g of white powder.

The white powder obtained was identified as Intermediate 23 by the FD-MS analysis.

Synthesis Example 24

Synthesis of Intermediate 24

The reaction was conducted in the same manner as in Synthesis Example 7 except that Intermediate 4 was used instead of Intermediate 5 to obtain 23.4 g of white powder.

The white powder obtained was identified as Intermediate 24 by the FD-MS analysis.

Synthesis Example 25

Synthesis of Intermediate 25

The reaction was conducted in the same manner as in Synthesis Example 8 except that Intermediate 24 was used instead of Intermediate 7 to obtain 20.3 g of white powder.

The white powder obtained was identified as Intermediate 25 by the FD-MS analysis.

Synthesis Example 26

Synthesis of Intermediate 26

Under a stream of argon, 300 ml of toluene and 150 ml of a 2M aqueous solution of sodium carbonate were added to 28.3 g of 3-iodobromobenzene, 15.6 g of 3-chlorophenylboronic acid and 2.31 g of tetrakis(triphenylphosphine) palladium(0). The resulting mixture was heated under reflux for 10 hours.

Immediately after the reaction, the resultant was filtered, and then the aqueous layer was removed. The organic layer was dried with sodium sulfate and then concentrated. The residue was purified by silica-gel column chromatography to obtain 15.2 g of white crystals.

The white crystals obtained were identified as Intermediate 26 by the FD-MS analysis.

Synthesized Intermediates 1 to 26 were shown below.

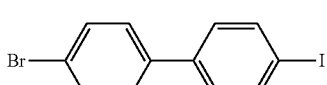

Intermediate 1

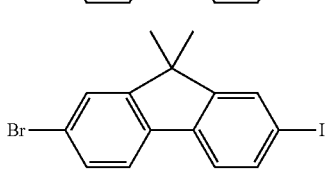

Intermediate 2

Intermediate 3
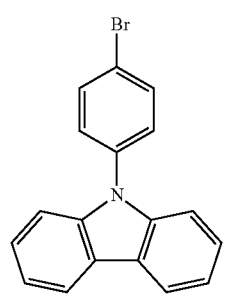
Intermediate 4
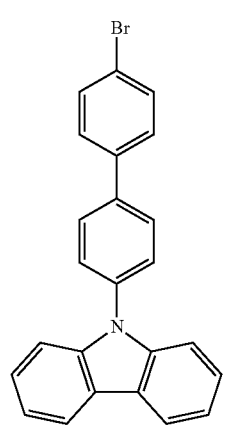
Intermediate 5
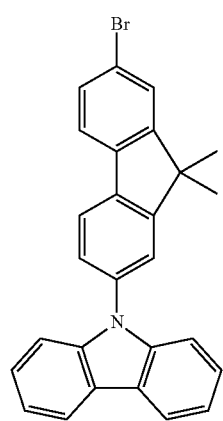
Intermediate 6
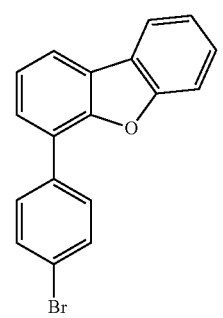
Intermediate 7
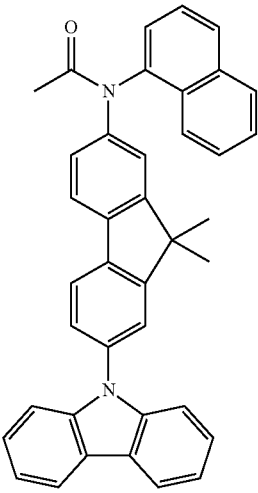
Intermediate 8
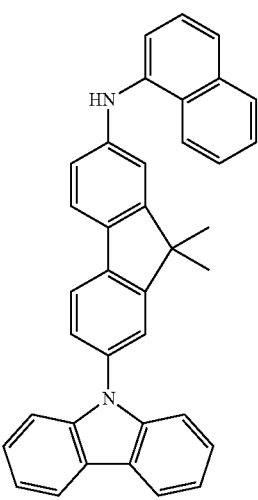
Intermediate 9
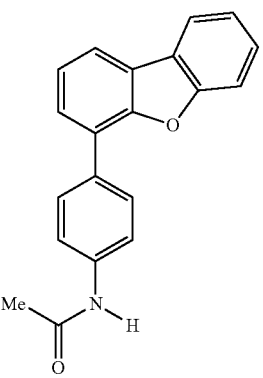

Intermediate 10
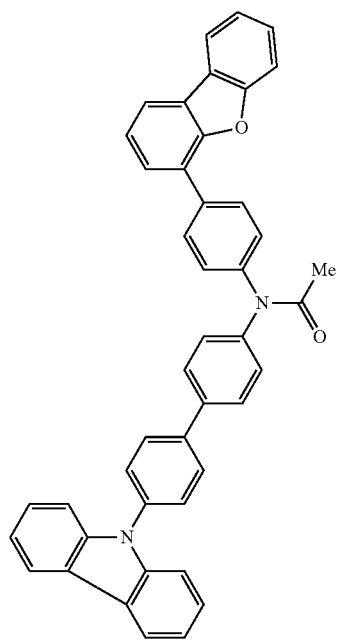
Intermediate 11
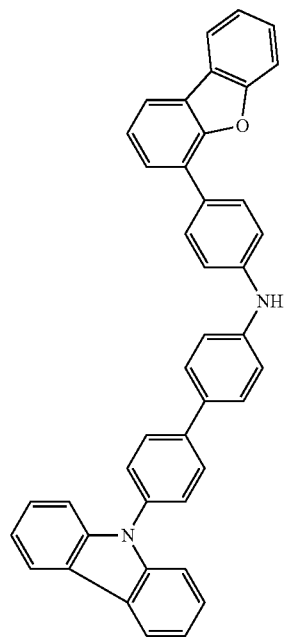
Intermediate 12
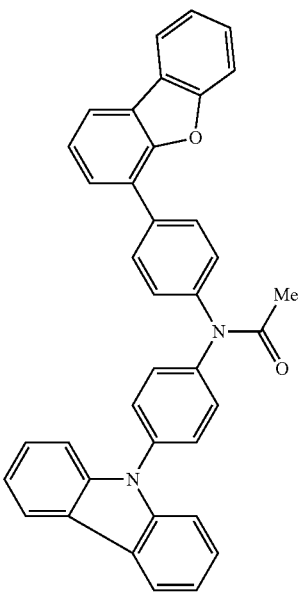
Intermediate 13
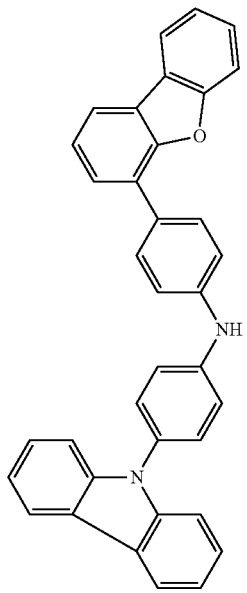

Intermediate 14
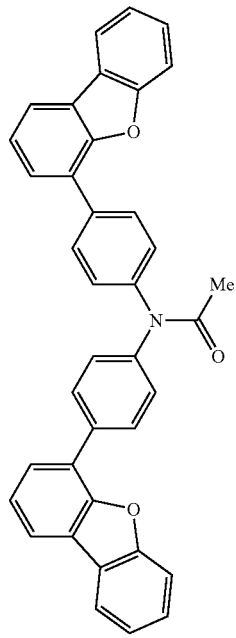
Intermediate 15
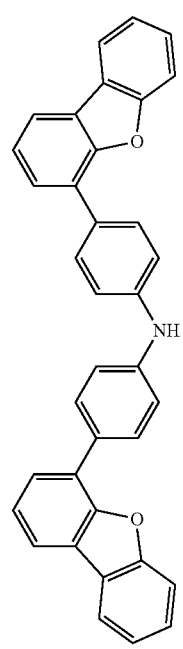
Intermediate 16
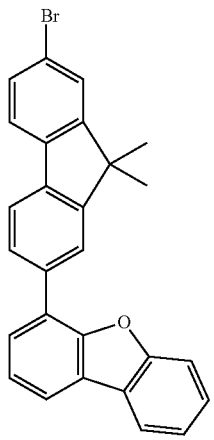
Intermediate 17
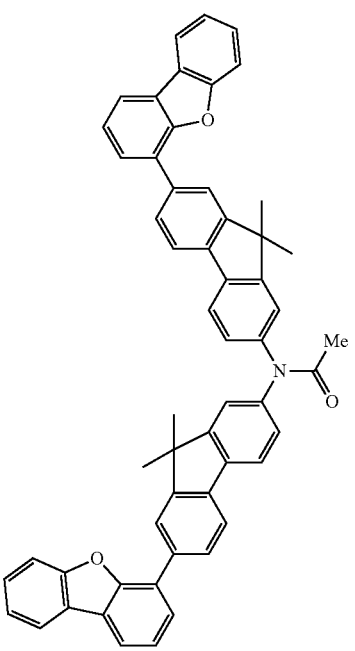

Intermediate 18
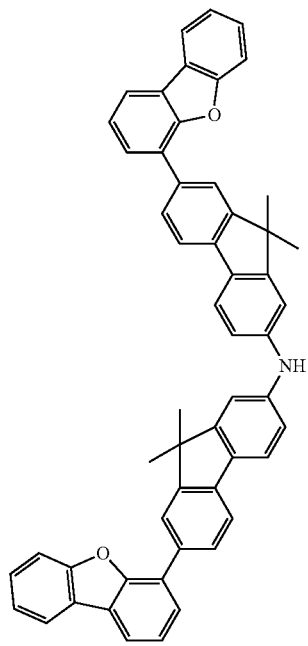
Intermediate 22
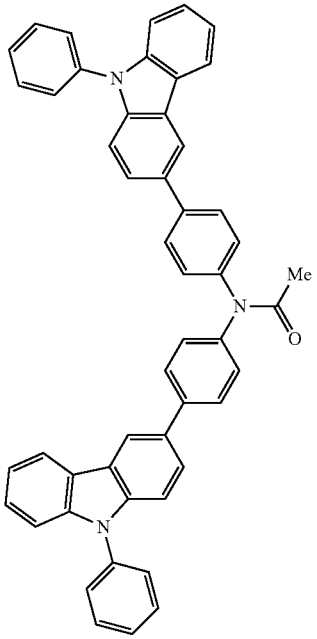
Intermediate 19
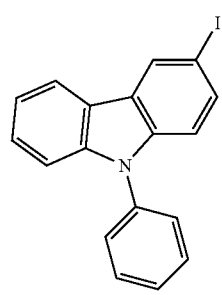
Intermediate 20
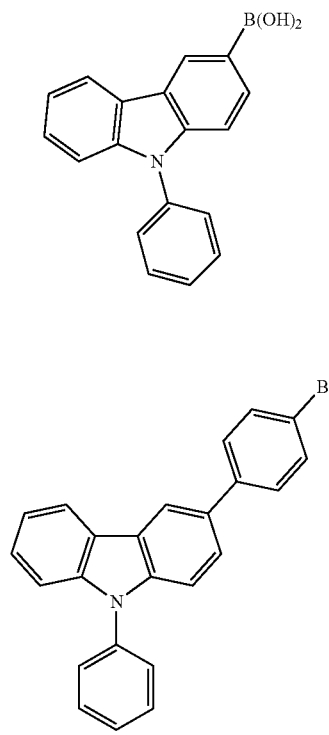
Intermediate 23
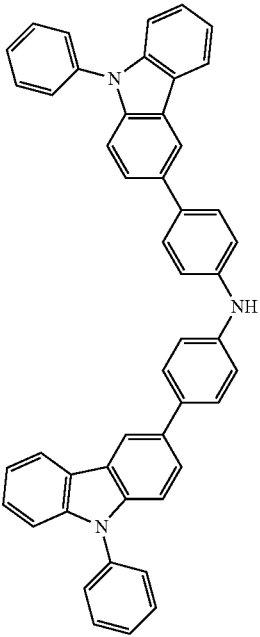
Intermediate 21
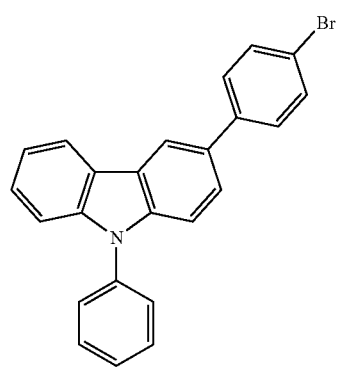

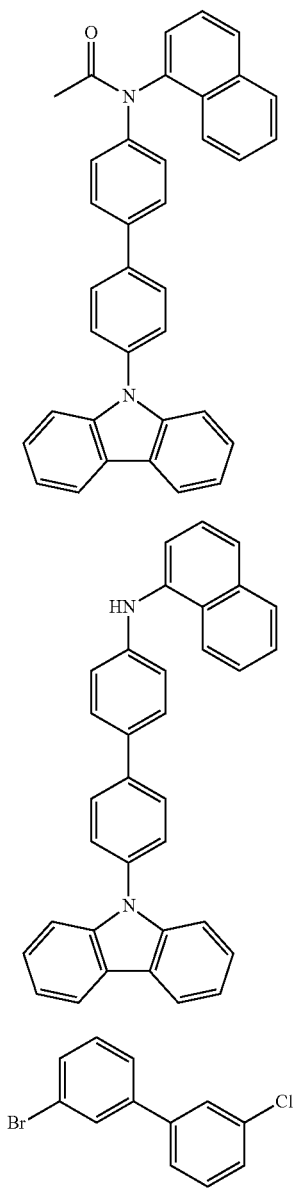

Intermediate 24

Intermediate 25

Intermediate 26

Example 1

Synthesis of Compound H1

Under a stream of argon, 15.0 g of Intermediate 8, 5.4 g of 1,3,5-tris(4-bromophenyl)benzene, 1.3 g of sodium t-butoxide, 46 mg of tris(dibenzilideneacetone)dipalladium(0), 21 mg of tri-t-butylphosphine and 50 ml of dehydrated toluene were placed and reacted at 80° C. for 8 hours.

After cooling, 500 ml of water was added thereto, and the mixture was filtered through celite. The filtrate was extracted with toluene and dried with anhydrous magnesium sulfate. This was concentrated under reduced pressure. The crude product obtained was purified using a column, and recrystallized from toluene. After filtered off, the resulting matter was dried to obtain 5.4 g of pale yellow powder.

The pale yellow powder obtained was identified as Compound H1 by the FD-MS analysis.

Example 2

Synthesis of Compound H2

A reaction was conducted in the same manner as in Example 1 except that 17.3 g of Intermediate 11 was used instead of Intermediate 8 to obtain 4.8 g of pale yellow powder.

The pale yellow powder obtained was identified as Compound H2 by the FD-MS analysis.

Example 3

Synthesis of Compound H3

A reaction was conducted in the same manner as in Example 1 except that 15.0 g of Intermediate 13 was used instead of Intermediate 8 to obtain 4.4 g of pale yellow powder.

The pale yellow powder obtained was identified as Compound H3 by the FD-MS analysis.

Example 4

Synthesis of Compound H4

A reaction was conducted in the same manner as in Example 1 except that 15.0 g of Intermediate 15 was used instead of Intermediate 8 to obtain 5.8 g of pale yellow powder.

The pale yellow powder obtained was identified as Compound H4 by the FD-MS analysis.

Example 5

Synthesis of Compound H5

A reaction was conducted in the same manner as in Example 1 except that 22.0 g of Intermediate 18 was used instead of Intermediate 8 to obtain 5.2 g of pale yellow powder.

The pale yellow powder obtained was identified as Compound H5 by the FD-MS analysis.

Example 6

Synthesis of Compound H6

A reaction was conducted in the same manner as in Example 1 except that 19.6 g of Intermediate 23 was used instead of Intermediate 8 to obtain 4.8 g of pale yellow powder.

The pale yellow powder obtained was identified as Compound H6 by the FD-MS analysis.

Example 7

Synthesis of Compound H7

A reaction was conducted in the same manner as in Example 1 except that 13.8 g of Intermediate 25 was used instead of Intermediate 8 to obtain 4.1 g of pale yellow powder.

The pale yellow powder obtained was identified as Compound H7 by the FD-MS analysis.

Example 8

Synthesis of Compound H8

Under a stream of argon, 10.0 g of Intermediate 15, 5.4 g of Intermediate 26, 2.6 g of sodium t-butoxide, 92 mg of tris(dibenzilideneacetone)dipalladium(0), 42 mg of tri-t-butylphosphine and 100 ml of dehydrated toluene were placed and reacted at 80° C. for 8 hours. After cooling, 500 ml of water was added thereto, and the mixture was filtered through celite. The filtrate was extracted with toluene and dried with anhydrous magnesium sulfate. The resulting matter was concentrated under reduced pressure. The crude product obtained was purified using columns, and recrystallized from toluene. After filtered off, the resulting matter was dried to obtain 8.4 g of pale yellow powder.

Under a stream of argon, 6.9 g of the pale yellow powder prepared, 5.8 g of Intermediate 11, 1.3 g of sodium t-butoxide, 46 mg of tris(dibenzilideneacetone)dipalladium(0), 21 mg of tri-t-butylphosphine and 50 ml of dehydrated toluene were placed and reacted at 80° C. for 16 hours. After cooling, 500 ml of water was added thereto, and the mixture was filtered through celite. The filtrate was extracted with toluene and dried with anhydrous magnesium sulfate. The resulting matter was concentrated under reduced pressure. The crude product obtained was purified using a column, and recrystallized from toluene. After filtered off, the resulting matter was dried to obtain 7.5 g of pale yellow powder.

The pale yellow powder obtained was identified as Compound H8 by the FD-MS analysis.

Example 9

Synthesis of Compound H9

(1) Synthesis of Intermediate 27

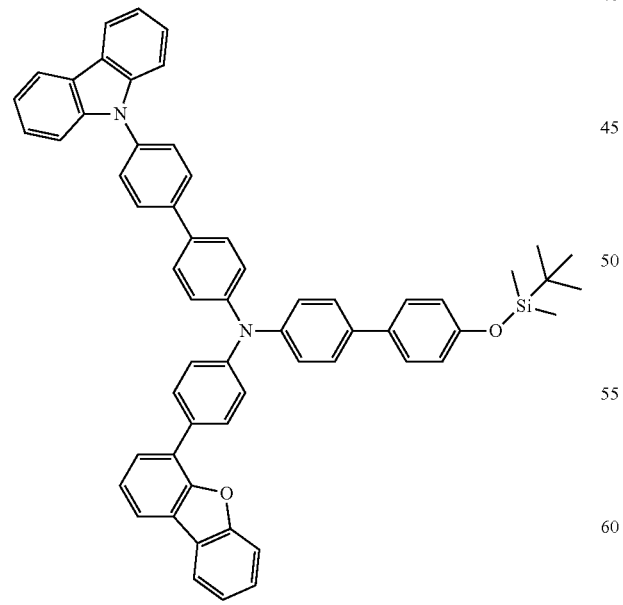

Intermediate 27

Under a stream of argon, 15.0 g of imidazole which is dissolved in 200 ml of methylene chloride was dropped to a mixture of 50.0 g of 4-bromo-4'-hydroxybiphenyl, 33.0 g of tert-butyldimethylchlorosilane, 220 ml of methylene chloride and 50 ml of N,N-dimethylformamide. The mixture was stirred at room temperature for 1 hour. After the reaction was completed, 500 ml of water was added to the reactant, and then the aqueous layer was removed. The organic layer was dried with sodium sulfate and then concentrated. The residue was purified by silica-gel column chromatography to obtain 69.0 g of 4-(4'-bromobiphenyloxy)(tert-butyl)dimethylsilane.

1 liter of toluene was added to 0.61 g of palladium acetate and 5.40 g of tri-tert-butylphosphine, and the mixture was stirred at room temperature for 30 minutes. After that, 49.0 g of 4-(4'-bromobiphenyloxy)(tert-butyl)dimethylsilane, 78.0 g of Intermediate 11 and 700 ml of toluene were added thereto, and the mixture was heated to 90° C. After adding 18.2 g of sodium tert-butoxide to the reaction solution, the resulting mixture was heated at 105° C. for 4 hours. After the reaction was completed, the reactant was washed with 1.5 liter of water, and the aqueous layer was removed. The organic layer was dried with sodium sulfate, and then concentrated. The residue was purified by silica-gel column chromatography to obtain 100 g of white solids.

The white crystals obtained were identified as Intermediate 27 by the FD-MS analysis.

(2) Synthesis of Intermediate 28

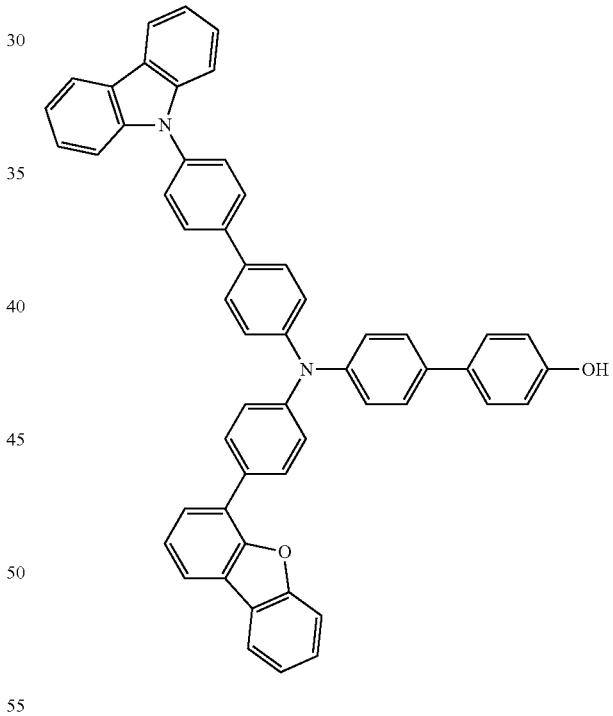

Intermediate 28

Under a stream of argon, 73.4 g of tetrabutylammonium fluoride trihydrate was added to 100 g of Intermediate 27 and 1.5 liter of tetrahydrofuran, and the mixture was stirred at room temperature for 2 hours. After the reaction was completed, the reaction solution was added to 1 liter of an aqueous solution of citric acid, followed by removal of the aqueous layer. The organic layer was dried with sodium sulfate and then concentrated. The residue was purified by silica-gel column chromatography to obtain 78.0 g of white solids.

The white crystals obtained were identified as Intermediate 28 by the FD-MS analysis.

(3) Synthesis of Intermediate 29

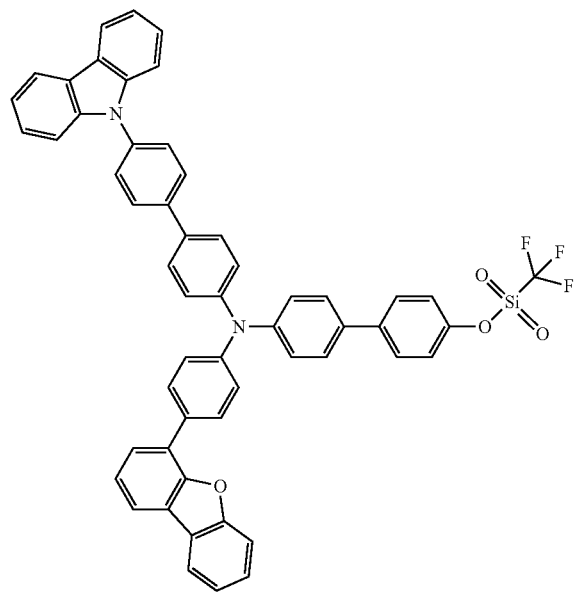

Intermediate 29

Under a stream of argon, 38.0 g of trifluoromethanesulfonic acid anhydrate was added to 78.0 g of Intermediate 28, 19.0 ml of triethylamine and 780 ml of methylene chloride, and the mixture was stirred at room temperature for 30 minutes. After the reaction was completed, 500 ml of water was added thereto, followed by removal of the aqueous layer. The organic layer was dried with sodium sulfate and then concentrated. The residue was purified by silica-gel column chromatography to obtain 71.0 g of white solids.

The white crystals obtained were identified as Intermediate 29 by the FD-MS analysis.

(4) Synthesis of Compound H9

Under argon atmosphere, 15 ml of dimethyl glycol and 8 ml of a 2M aqueous solution of sodium carbonate were added to 2.89 g of Intermediate 29, 0.84 g of 9,9-dioctylfluorene-2,7-diboronic acid bis(1,3-propanediol) ester and 0.09 g of tetrakis(triphenylphosphine)palladium(0), and the resulting mixture was heated under reflux for 7 hours. After the reaction was completed, the aqueous layer was removed. After the organic layer was dried with sodium sulfate, it was concentrated. The residue was purified by silica-gel column chromatography to obtain 1.36 g of white solids.

The white solids obtained were identified as H9 by the FD-MS analysis.

Example 10

Synthesis of Compound H10

(1) Synthesis of Intermediate 30

Under argon atmosphere, 20 ml of DME and 20 ml of a 2M aqueous solution of sodium carbonate were added to 5.0 g of Intermediate 1, 3.4 g of 9,9-dioctylfluorene-2,7-diboronic acid and 0.3 g of tetrakis(triphenylphosphine)palladium(0), and the mixture was heated under reflux for 6 hours.

After completion of the reaction, 100 ml of dichloromethane and 100 ml of water were added to the reactant and an intended substance was extracted to remove the organic layer. The organic layer was dried with $MgSO_4$, and $MgSO_4$ was removed by filtration. The solvent was removed under reduced pressure and isolated by column chromatography to obtain 2.8 g of white crystals.

The white crystals obtained were identified as Intermediate 30 by the FD-MS analysis.

(2) Synthesis of Compound H10

Under a stream of argon, 3.0 g of Intermediate 15, 2.3 g of Intermediate 30, 1.6 g of sodium t-butoxide, 18 mg of palladium(0) acetate, 44 mg of tri-t-butylphosphine and 10 ml of dehydrated toluene were placed, and the resultant was reacted for 8 hours while stirring.

After cooling, 500 ml of water was added thereto, the resulting mixture was filtrated through celite. The filtrate was extracted with toluene and dried with anhydrous magnesium sulfate. The resulting matter was concentrated under reduced pressure to obtain a crude product. The crude product obtained was purified by silica-gel column chromatography to obtain 2.8 g of pale yellow powder.

The pale yellow powder obtained was identified as H10 by the FD-MS analysis.

Example 11

Synthesis of Compound H11

(1) Synthesis of Intermediate 31

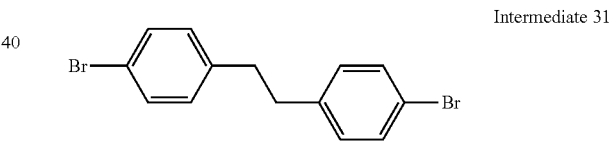

Intermediate 31

A cooling tube and a dropping funnel were attached to a 500 ml three-necked round-bottom flask, and a magnetic stirrer (stirring bar) was set in the flask. Reaction was conducted under a stream of argon while sufficient stirring. A dehydration-grade solvent was used in the reaction.

100 ml of the solvent THF (tetrahydrofuran) and 22.74 g of 4-bromobenzylbromide were placed in the three-necked Intermediate 30

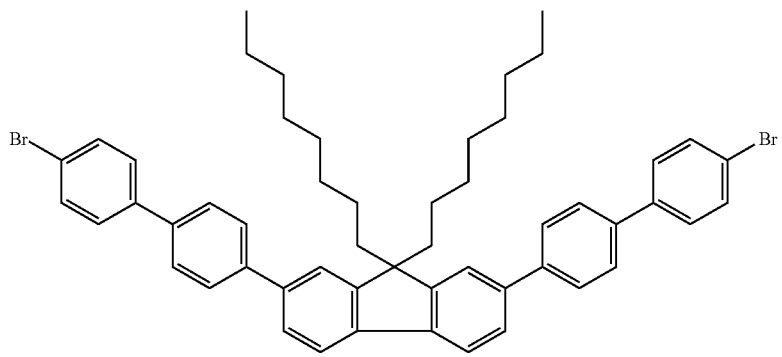

round-bottom flask. Thereto, under reflux, n-butylmagnesium chloride diluted in 100 ml of the THF (0.91M hexane solution: 100 ml) was dropped slowly through the dropping funnel. Reaction was conducted under reflux for 5 hours.

After completion of the reaction, the reaction solution was poured into a large volume of water, followed by extraction with methylene chloride using a separating funnel. Next, under reduced pressure, the solvent for organic layer (methylene chloride and THF) was distilled off to obtain a crude product. The crude product was recrystallized with a mixed solvent of methylene chloride and hexane to obtain 10.0 g of purified substance.

The purified substance obtained was identified as Intermediate 31 by structure confirmation with $^1$H-NMR spectroscopy.

(2) Synthesis of Intermediate 32

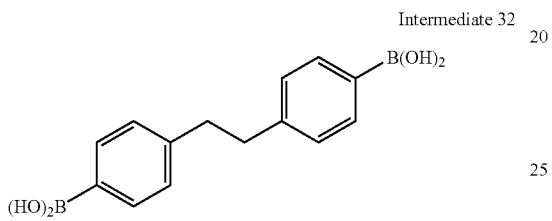

Intermediate 32

A magnetic stirrer (stirring bar) was set in a 200 ml two-necked round-bottom flask. Reaction was conducted under a stream of argon while sufficient stirring. A dehydration-grade solvent was used in the reaction.

75 ml of the solvent THF and 5.10 g of Intermediate 31 obtained in the above-mentioned synthesis (1) were placed in the two-necked round-bottom flask and cooled to −78° C. Thereto, n-butyllithium (1.6M hexane solution: 28.15 ml) was added dropwise slowly. After completion of the dropwise addition, the resulting mixture was heated to room temperature gradually, followed by reaction at room temperature for 1 hour. Next, the reaction solution was cooled to −78° C. again, and 6.50 g of tri-n-butylborate was dropped thereto. After completion of the dropwise addition, the resulting mixture was heated to room temperature gradually, followed by reaction at room temperature for 1 hour. At last, the reaction solution was poured into a large volume of water, dilute hydrochloric acid (3N) was added to the reaction solution until the solution becomes acidic, and the resulting mixture was stirred sufficiently. Resulting white solids were filtrated and dried to obtain Intermediate 32 (3.04 g).

(3) Synthesis of Compound H11

A magnetic stirrer (stirring bar) was set in a 200 ml two-necked round-bottom flask. A reaction was conducted while sufficient stirring.

3.53 g of Intermediate 29, 0.44 g of Intermediate 32, 0.188 g of tetrakis(triphenylphosphine)palladium(0), 2.29 g of sodium carbonate, 40 ml of DME (1,2-dimethoxyethane) as a solvent and 20 ml of water ware placed in the 200 ml two-necked round-bottom flask in sequence and reacted under reflux for 5 hours.

After completion of the reaction, the reaction solution was poured into a large volume of water, followed by extraction with methylene chloride using a separating funnel. Next, under reduced pressure, the solvent for organic layer (methylene chloride and DME) was distilled off to obtain a crude product. The crude product was separated and purified by silica-gel column chromatography (developing solvent: methylene chloride). Further, the purified substance was dissolved in toluene to obtain a solution. The solution obtained was poured into a large volume of acetone through a filter paper while stirring to obtain precipitated solids (0.80 g). The solids obtained were identified as H11 by the FD-MS analysis.

Example 12

Synthesis of Compound H12

(1) Synthesis of Intermediate 33

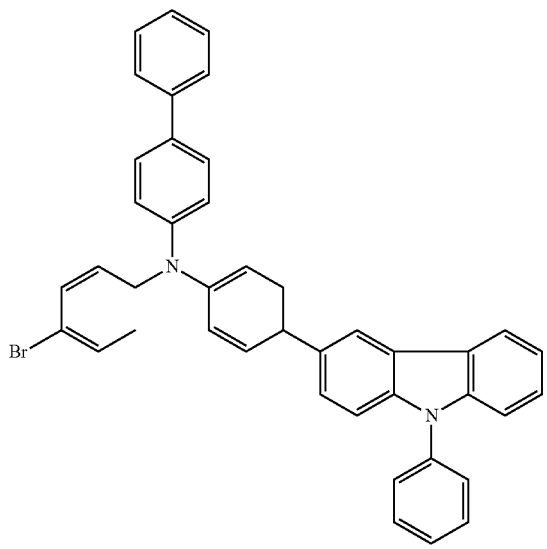

Intermediate 33

A magnetic stirrer (stirring bar) was set in a 200 ml two-necked round-bottom flask. A reaction was conducted while sufficient stirring.

3.91 g of 4-4'-dibromo-4"-phenyltriphenylamine, 2.34 g of 9-phenylcarbazole-3-boronic acid, 0.471 g of tetrakis (triphenylphosphine) palladium (0), 5.72 g of sodium carbonate, 100 ml of DME (1,2-dimethoxyethane) as a solvent and 50 ml of water ware placed in the 200 ml two-necked round-bottom flask in sequence and reacted under reflux for 5 hours.

After completion of the reaction, the reaction solution was poured into a large volume of water, followed by extraction with methylene chloride using a separating funnel. Next, under reduced pressure, the solvent for organic layer (methylene chloride and DME) was distilled off to obtain a crude product. The crude product was separated and purified by silica-gel column chromatography (developing solvent: a mixed solution of 50 volume % of methylene chloride and 50 volume % of hexane) to obtain 1.90 g of Intermediate 33.

(2) Synthesis of Compound H12

A magnetic stirrer (stirring bar) was set in a 200 ml two-necked round-bottom flask. A reaction was conducted while sufficient stirring.

1.10 g of Intermediate 33 (molecular weight 641.60, 1.71 millimoles), 0.220 g of Intermediate 32, 0.094 g of tetrakis (triphenylphosphine)palladium(0), 1.15 g of sodium carbonate, 20 ml of DME as a solvent and 10 ml of water ware placed in the 200 ml two-necked round-bottom flask in sequence and reacted under reflux for 5 hours.

After completion of the reaction, the reaction solution was poured into a large volume of water, followed by extraction with methylene chloride using a separating funnel. Next, under reduced pressure, the solvent for organic layer (methylene chloride and DME) was distilled off to obtain a crude product. The crude product was separated and purified by silica-gel column chromatography (developing solvent: a mixed solution of 50 volume % of methylene chloride and 50 volume % of hexane) to obtain 0.60 g of Compound H12. The conformation of H12 was conducted by the FD-MS analysis.

Example 13

Synthesis of Compound H13

(1) Synthesis of Intermediate 34

Intermediate 34

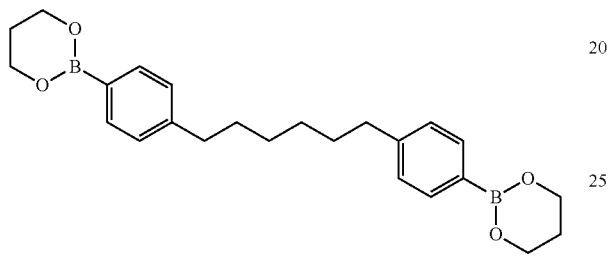

Under a stream of argon, 300 ml of dehydrated tetrahydrofuran was added to 23.8 g of 1-bromo-4-iodobenzene, and the mixture was cooled to −78° C. 102 ml of a hexane solution of n-butyllithium (1.65M) was dropped thereto, followed by stirring for 1 hour. Subsequently, 4.95 ml of 1,6-diiodohexane was added dropwise to the mixture slowly, followed by reaction for 2 hours. After returned to room temperature, a 10% dilute hydrochloric acid solution was added thereto, the resulting mixture was stirred, and then an organic layer was extracted. After washed with saturated saline, the organic phase was dried with anhydrous magnesium sulfate, filtered off and concentrated. The solution obtained was purified by silica-gel chromatography to obtain 6.89 g of 1,6-bis(4-bromophenyl) hexane in the form of a colorless oily substance.

Under a stream of argon, 100 ml of dehydrated tetrahydrofuran was added to 6.89 g of 1,6-bis(4-bromophenyl) hexane, and the mixture was cooled to −45° C. 27.4 ml of a hexane solution of n-butyllithium (1.65M) was dropped thereto, and the resulting mixture was heated to −5° C. over 1 hour while stirring. The mixture was cooled to −45° C. again, and 14.1 ml of boronic acid triisopropyl ester was dropped slowly thereto, followed by reaction for 2 hours. After the reactant was returned to room temperature, a 10% dilute hydrochloric acid solution was added thereto, the resulting mixture was stirred and concentrated. After the solids obtained were washed with 200 ml of water and dried under reduced pressure, 4.88 ml of 1,3-propanediol and 30 ml of toluene were added to the solids obtained, followed by heating under reflux for 5 hours. After completion of the reaction, the resultant was concentrated, and the residue was purified by silica-gel column chromatography to obtain 1.13 g of white crystals.

The white crystals obtained were identified as Intermediate 34 by the FD-MS analysis.

(2) Synthesis of Compound H13

Under argon atmosphere, 27 ml of dimethylgrycol and 13 ml of a 2M aqueous solution of sodium carbonate were added to 3.11 g of Intermediate 33, 0.89 g of Intermediate 34 and 0.13 g of tetrakis(triphenylphosphine)palladium(0), and the mixture was heated under reflux for 7 hours. After completion of the reaction, the aqueous layer was removed. The organic layer was dried with sodium sulfate and then concentrated. The residue was purified by silica-gel column chromatography to obtain 3.04 g of white solids.

The white solids obtained were identified as H13 by the FD-MS analysis.

Example 14

Synthesis of Compound H14

(1) Synthesis of Intermediate 35

Intermediate 35

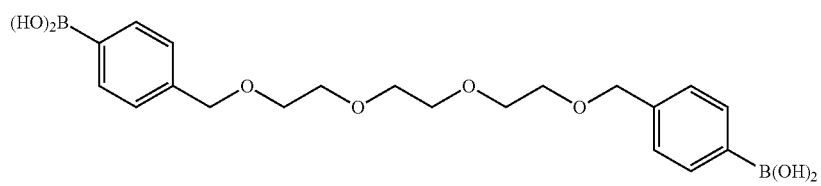

Under argon atmosphere, 1.76 g of sodium hydroxide was added to 3.00 g of triethylene glycol and 80 ml of tetrahydrofuran in an ice bath, followed by stirring for 30 minutes. Subsequently, 11.0 g of 4-bromobenzylbromide was added thereto, and the resulting mixture was stirred at 40° C. for 5 hours. After completion of the reaction, 30 ml of water was added to the reactant, and then the aqueous layer was removed. The organic layer was dried with sodium sulfate and then concentrated. The residue was purified by silica-gel column chromatography to obtain 8.90 g of 1,12-bis(4-bromophenyl)-2,5,8,11-tetraoxadodecane in the form of a colorless oily substance.

Under a stream of argon, 40 ml of dehydrated tetrahydrofuran was added to 2.44 g of 1,12-bis(4-bromophenyl)-2,5,8,11-tetraoxadodecane, and the mixture was cooled to −45° C. 8.20 ml of a hexane solution of n-butyllithium (1.58M) was added dropwise thereto, and the mixture was heated to −5° C. with stirring over 1 hour. The mixture was cooled to −45° C. again, and 4.04 ml of boronic acid triisopropyl ester was added dropwise slowly thereto, followed by reaction for 2 hours.

After the reactant was returned to room temperature, a 10% dilute hydrochloric acid solution was added thereto, the resulting mixture was stirred, and the organic layer was extracted. After washed with saturated saline, the organic layer was dried with anhydrous magnesium sulfate, filtered off and then concentrated. The solids obtained were purified by silica-gel chromatography to obtain 1.56 g of a colorless oily substance. The colorless oily substance obtained was identified as Intermediate 35 by the FD-MS analysis.

(2) Synthesis of Compound H14

Under argon atmosphere, 15 ml of dimethylgrycol and 8 ml of a 2M aqueous solution of sodium carbonate were added to 3.95 g of Intermediate 29, 0.63 g of Intermediate 35 and 0.09 g of tetrakis(triphenylphosphine)palladium(0), and the mixture was heated under reflux for 6 hours. After completion of the reaction, the aqueous layer was removed. The organic layer was dried with sodium sulfate and then concentrated. The residue was purified by silica-gel column chromatography to obtain 1.33 g of white solids.

The white solids obtained were identified as H14 by the FD-MS analysis.

Example 15

Synthesis of Compound H15

(1) Synthesis of Intermediate 36

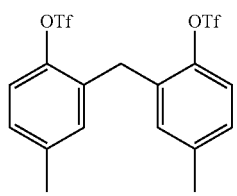

Intermediate 36

Under a stream of argon, 5 g of 2,2'-dihydroxy-5,5'-dimethyldiphenylmethane, 5.6 g of 2,6-lutidine and 150 ml of dehydrated dichloromethane were mixed, and the mixture was cooled to 0° C. in an ice bath. Next, 14.8 g of anhydrous trifluoromethanesulfonic acid was added thereto. After that, the mixture was returned to room temperature naturally, followed by reaction for 5 hours.

After completion of the reaction, 150 ml of water was added to the reactant, and an intended substance was extracted to obtain an organic layer. The organic layer obtained was dried with $MgSO_4$ and then $MgSO_4$ was removed by filtration. The solvent was removed under reduced pressure, and the resulting matter was isolated by column chromatography to obtain 10.2 g of pale orange solids.

The solids obtained were identified as Intermediate 36 by the FD-MS analysis.

(2) Synthesis of Intermediate 37

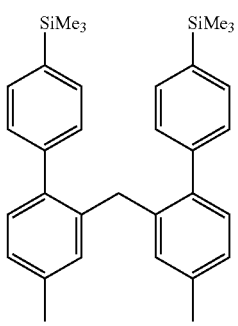

Intermediate 37

Under a stream of argon, 12 ml of DME and 12 ml of a 2M aqueous solution of sodium carbonate were added to 2.0 g of Intermediate 36, 2.4 g of p-trimethylsilylphenyl boronic acid and 0.2 g of tetrakis(triphenylphosphine)palladium(0), and the mixture was heated under reflux for 6 hours.

After completion of the reaction, 100 ml of dichloromethane and 100 ml of water were added to the reactant, and an intended substance was extracted to obtain an organic layer. The organic layer obtained was dried with $MgSO_4$ and then $MgSO_4$ was removed by filtration. The solvent was removed under reduced pressure, and the resulting matter was isolated by column chromatography to obtain 1.7 g of white powder.

The powder obtained was identified as Intermediate 37 by the FD-MS analysis.

(3) Synthesis of Intermediate 38

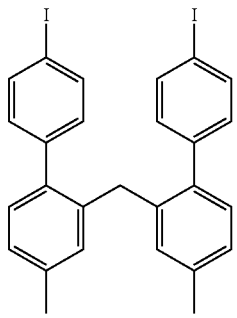

Intermediate 38

Under a stream of argon, 2.0 g of Intermediate 37 and dehydrated dichloromethane were mixed, and the mixture was cooled to 0° C. in an ice bath. Next, 1.4 g of iodine chloride was added thereto, and then the resulting mixture was return to room temperature naturally, followed by stirring for 1 hour. The resulting mixture was quenched with sodium thiosulfate. 50 ml of water was added thereto to extract an intended substance, thereby to obtain an organic layer. The organic layer obtained was dried with $MgSO_4$, and $MgSO_4$ was removed by filtration. The solvent was removed under reduced pressure, and the resulting matter was isolated by column chromatography to obtain 2.2 g of white powder.

The powder obtained was identified as Intermediate 38 by the FD-MS analysis.

(4) Synthesis of Intermediate 39

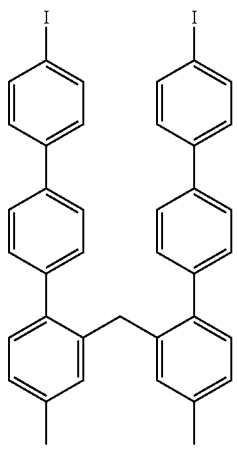

Intermediate 39

Intermediate 39 was synthesized by using Intermediate 38 in the same manner as in the syntheses of Intermediates 37 and 38.

(5) Synthesis of Compound H15

Under a stream of argon, 7.4 g of Intermediate 15, 5.0 g of Intermediate 39, 1.3 g of sodium t-butoxide, 45 mg of palladium(0) acetate, 108 mg of tri-t-butylphosphine and 10 ml of dehydrated toluene were placed and reacted under reflux for 8 hours.

After cooling, 500 ml of water was added thereto, and the mixture was filtrated through celite. The filtrate was extracted with toluene, followed by drying with anhydrous magnesium sulfate. This was concentrated under reduced pressure to obtain a crude product. The crude product obtained was purified by silica-gel column chromatography to obtain 7.0 g of white powder.

The white solids obtained were identified as H15 by the FD-MS analysis.

Example 16

Synthesis of Compound H16

Under a stream of argon, 8.7 g of Intermediate 11, 3.8 g of 2,7-dibromo-9,9-dioctylfluorene, 1.3 g of sodium t-butoxide, 45 mg of palladium(0) acetate, 108 mg of tri-t-butylphosphine and 10 ml of dehydrated toluene were placed and reacted under reflux for 8 hours.

After cooling, 500 ml of water was added thereto, and the mixture was filtrated through celite. The filtrate was extracted with toluene, followed by drying with anhydrous magnesium sulfate. The resulting matter was concentrated under reduced pressure to obtain a crude product. The crude product obtained was purified by silica-gel column chromatography to obtain 7.1 g of white powder.

The white solids obtained were identified as H16 by the FD-MS analysis.

Synthesized compounds H1 to H16 were shown below:

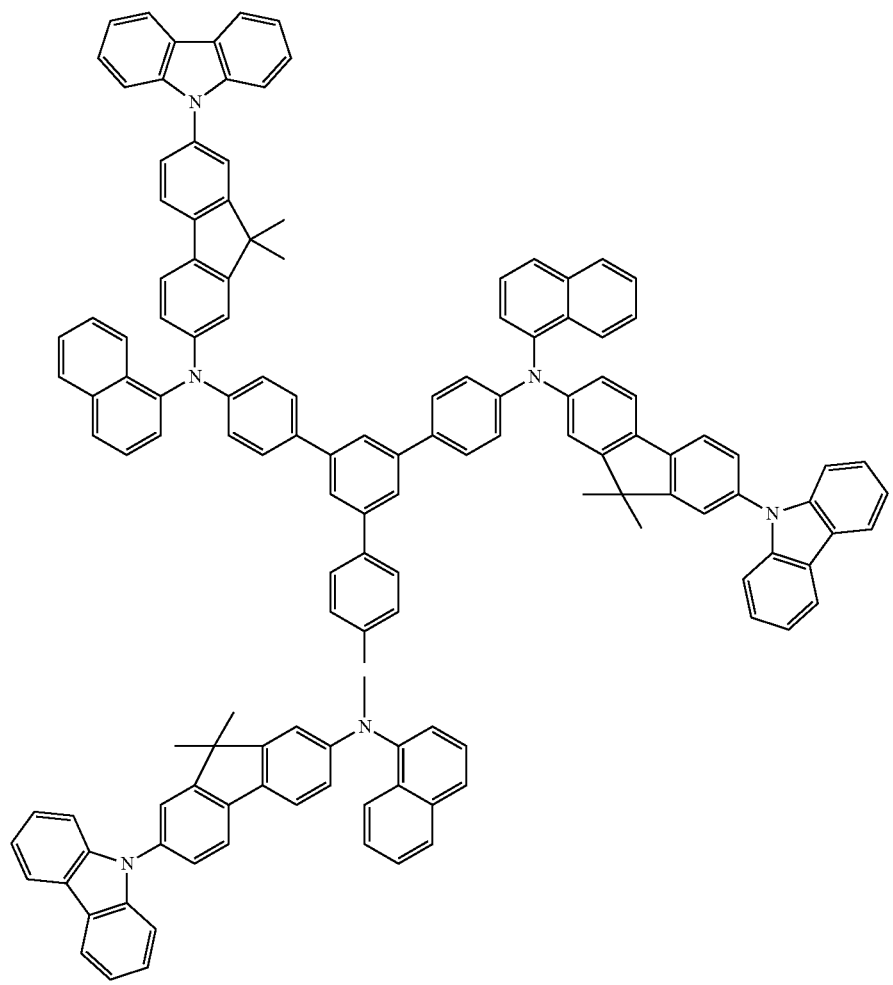

H1

-continued
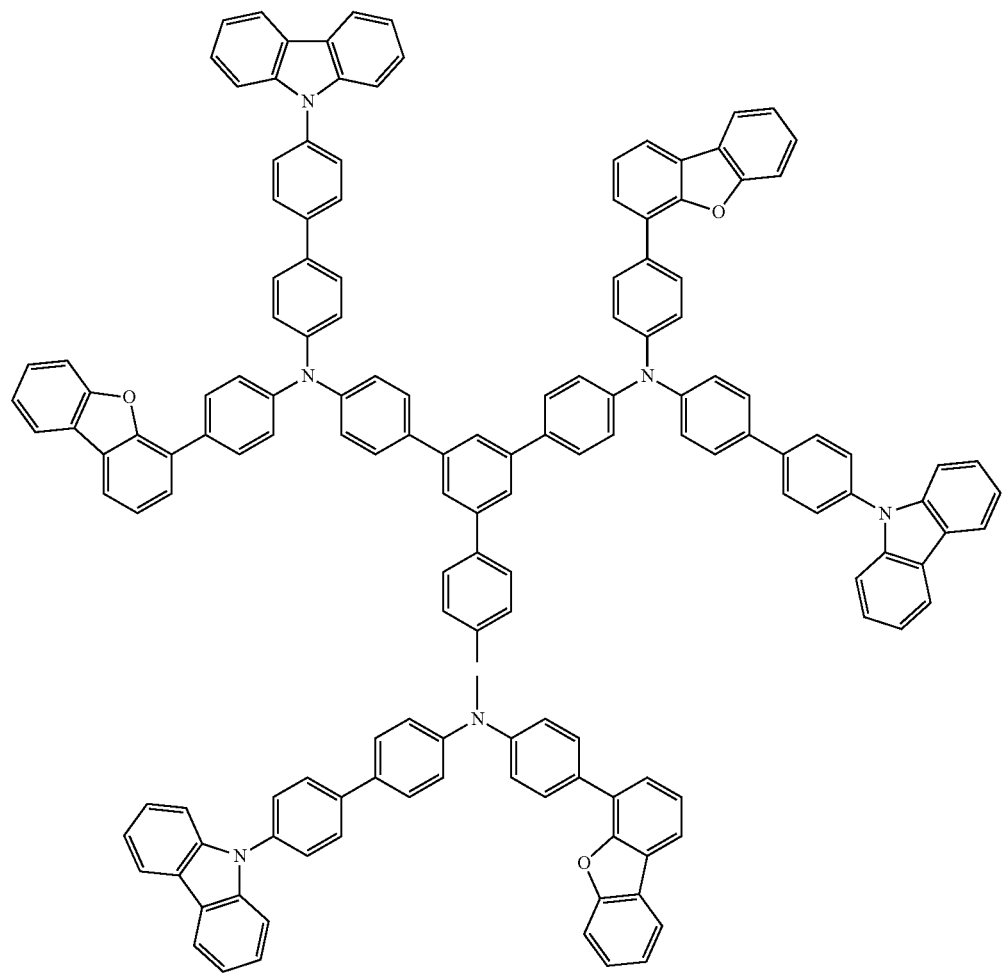
H2
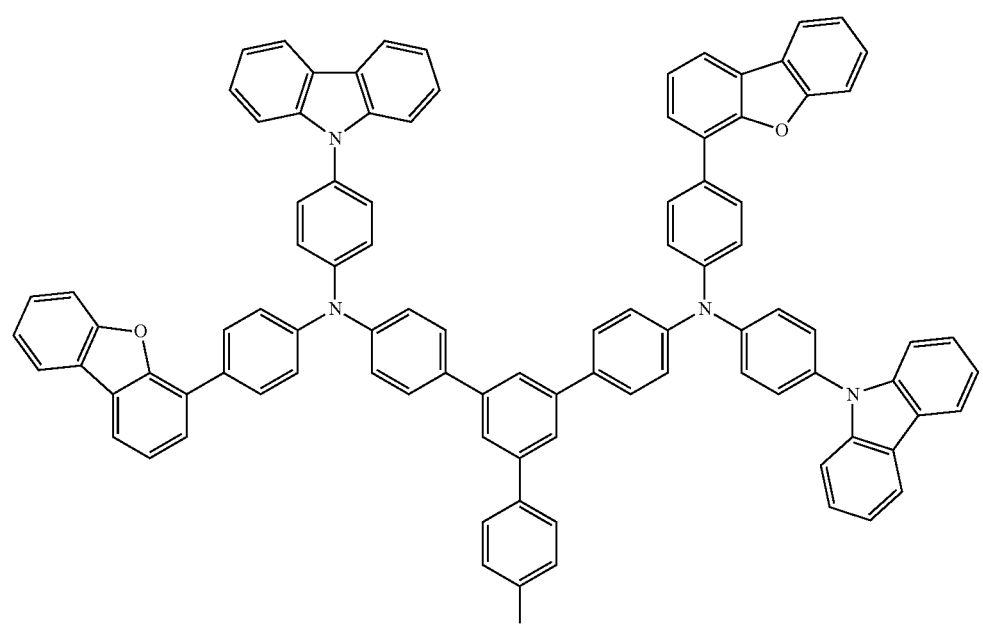
H3

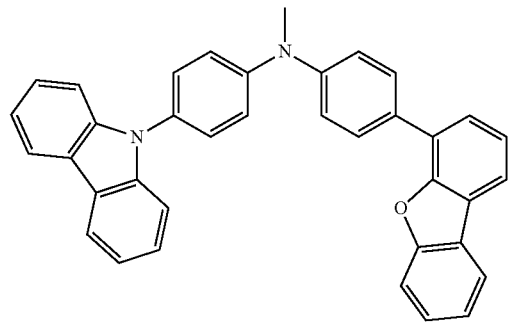
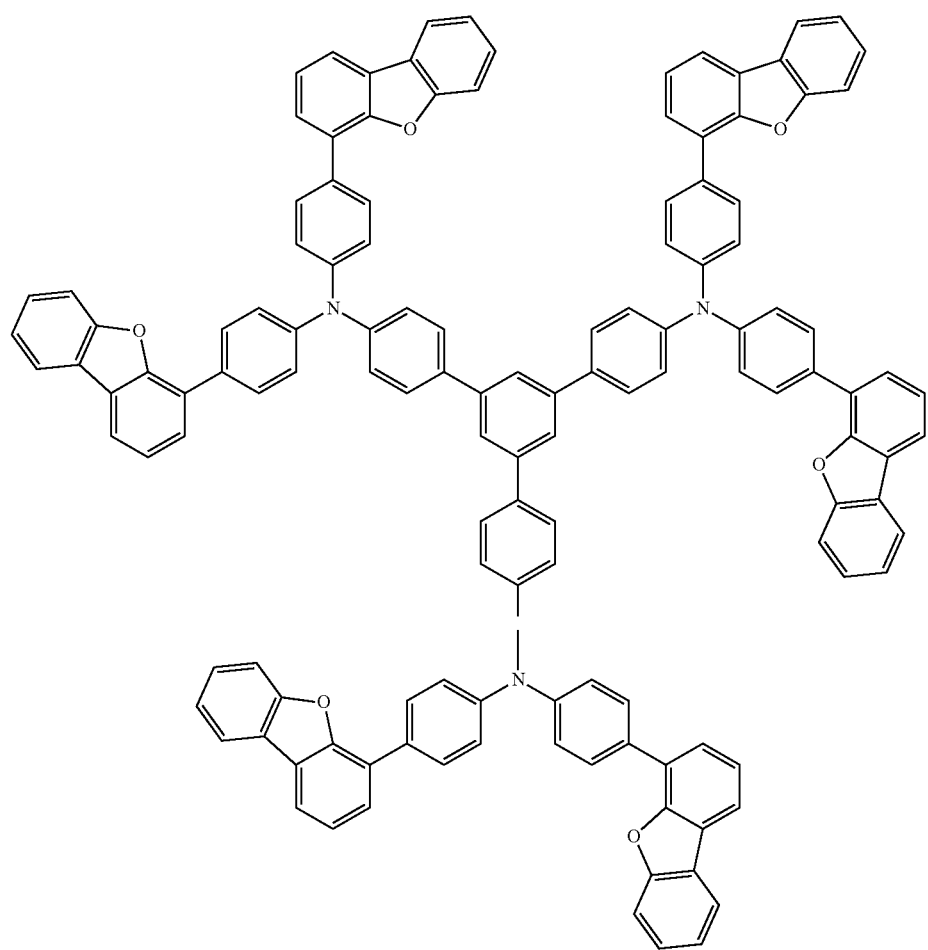
H4

H5
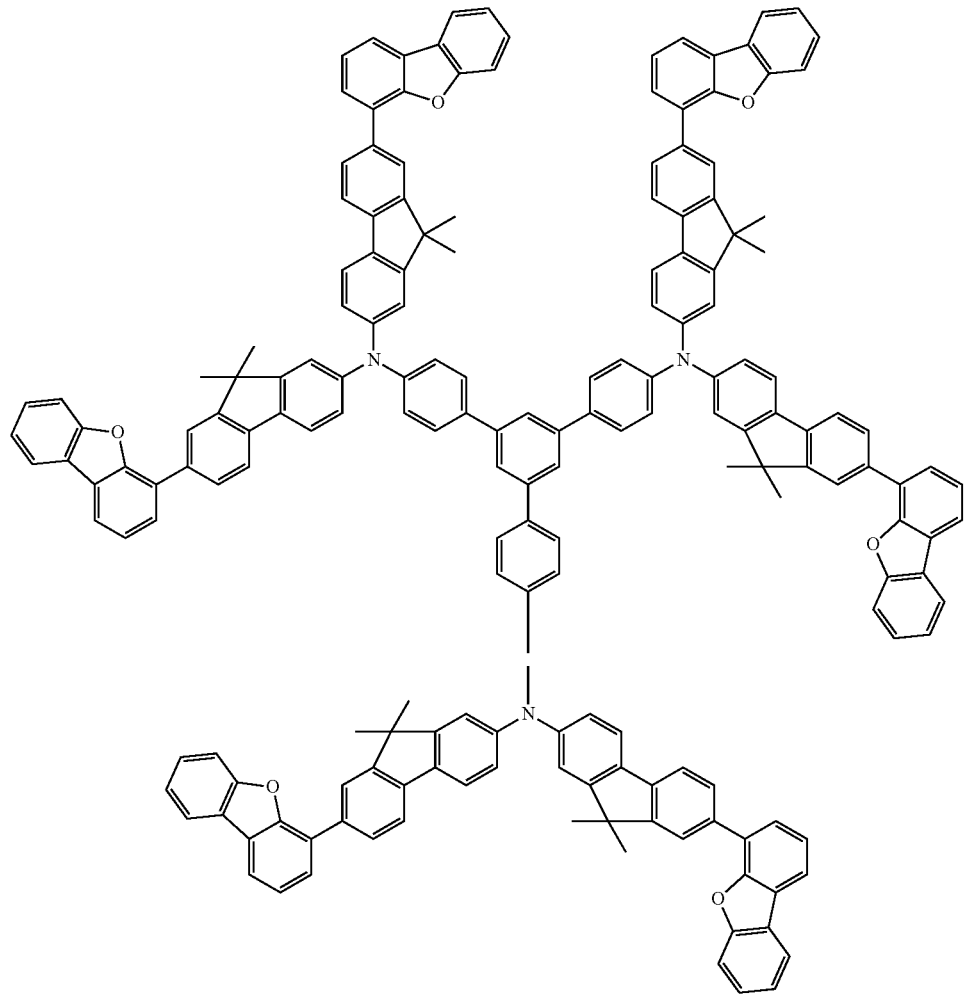
H6
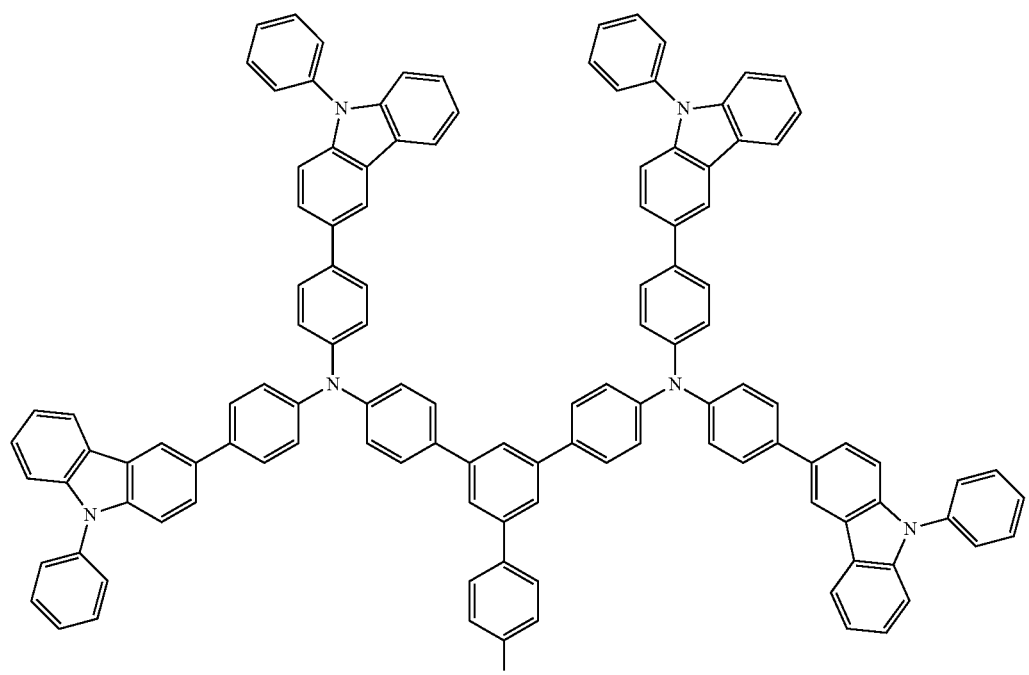

-continued
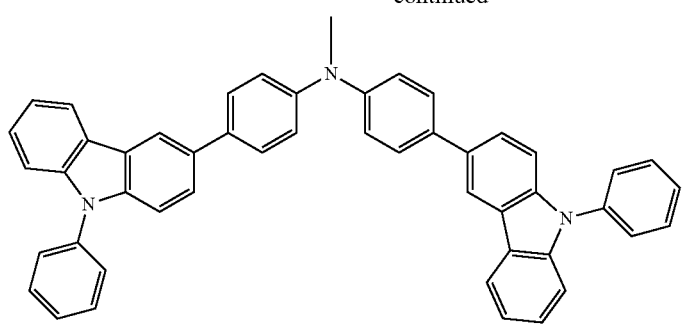
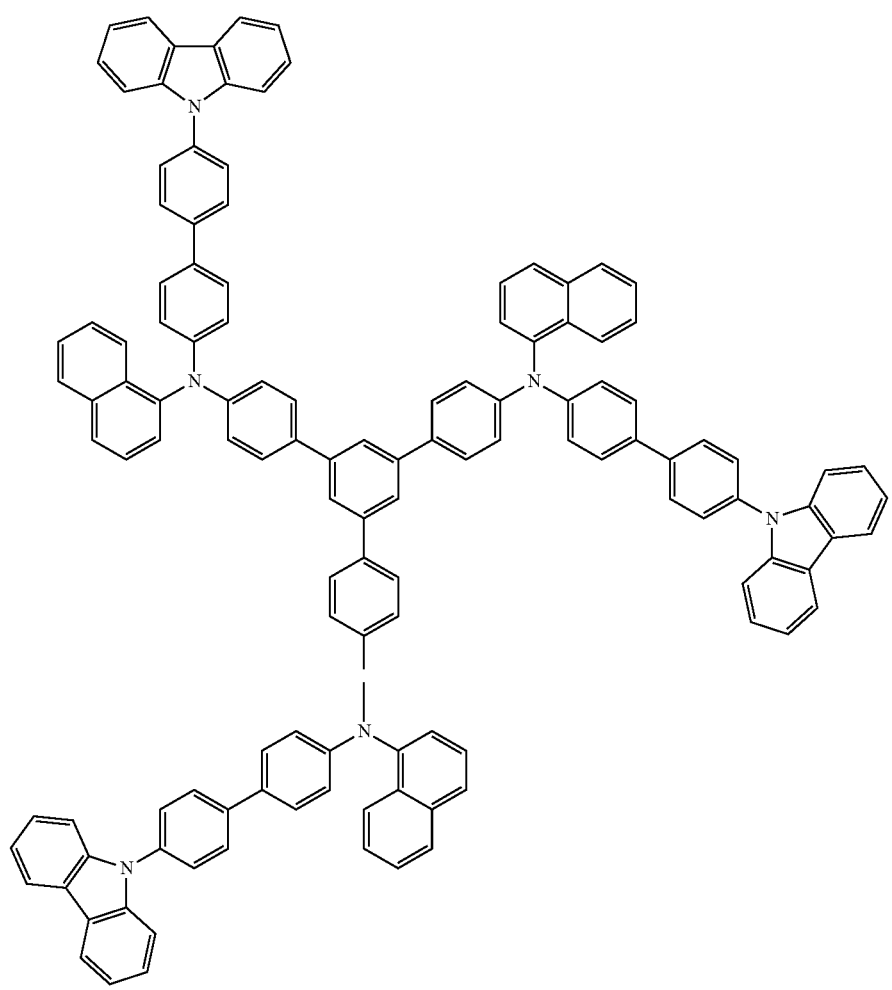
H7

-continued
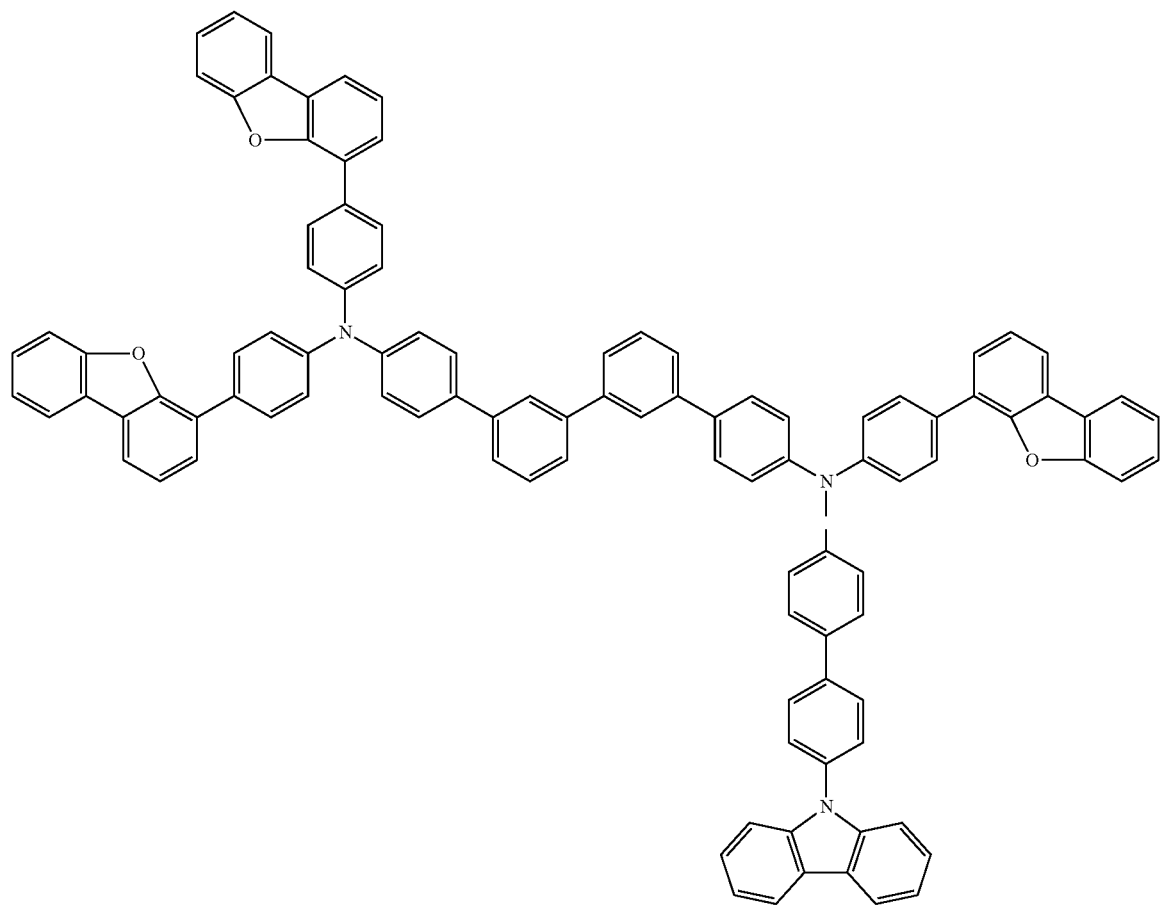
H8
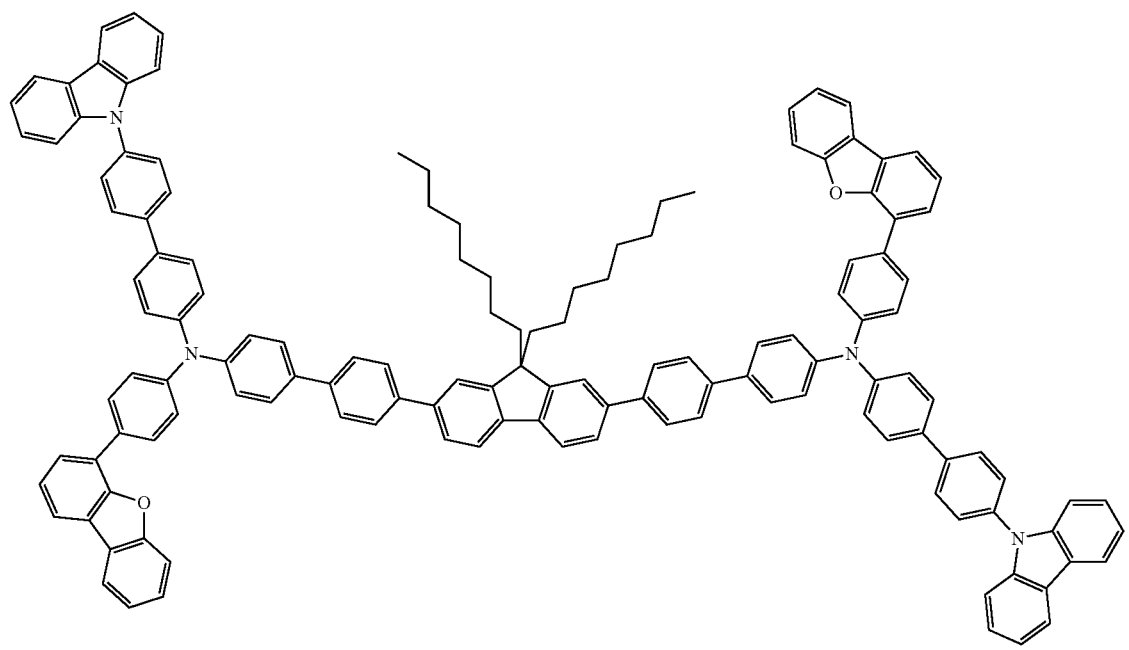
H9

-continued
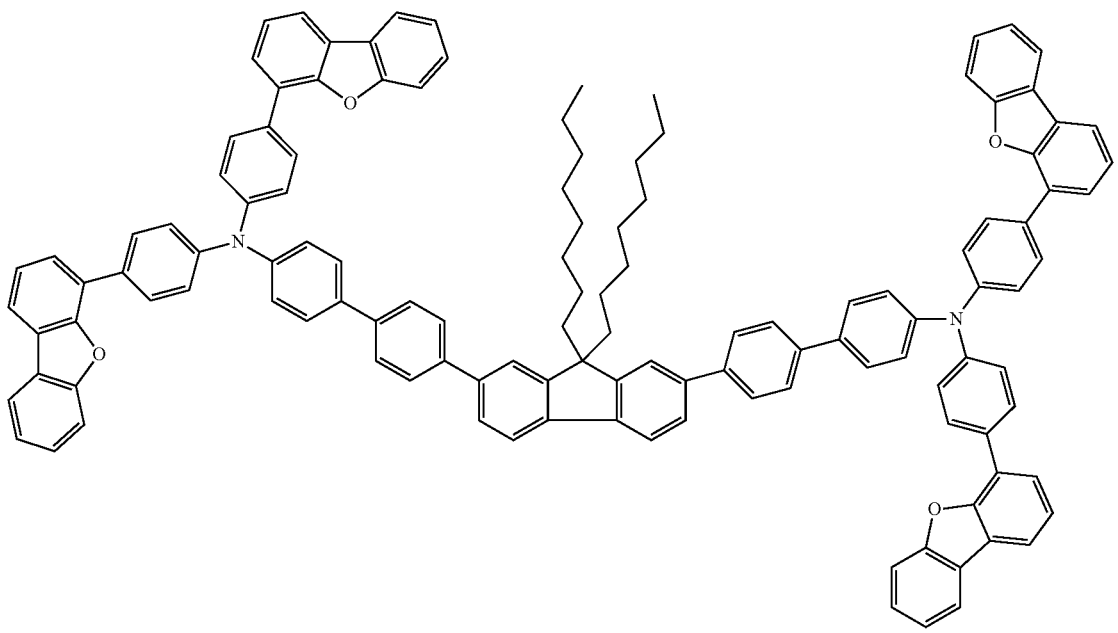
H10
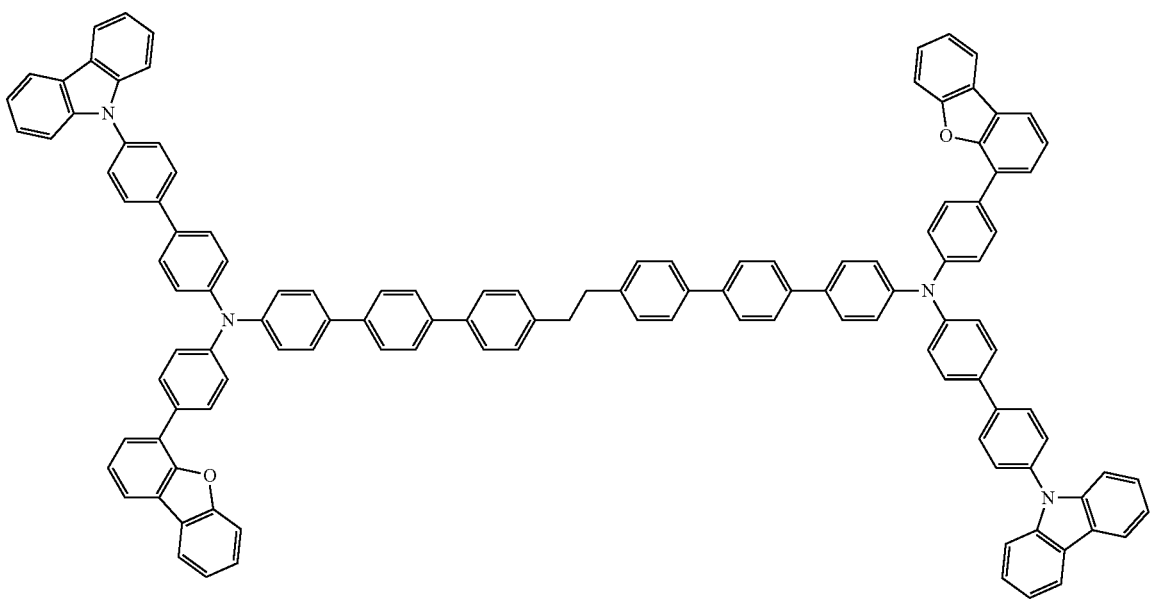
H11

-continued
H12
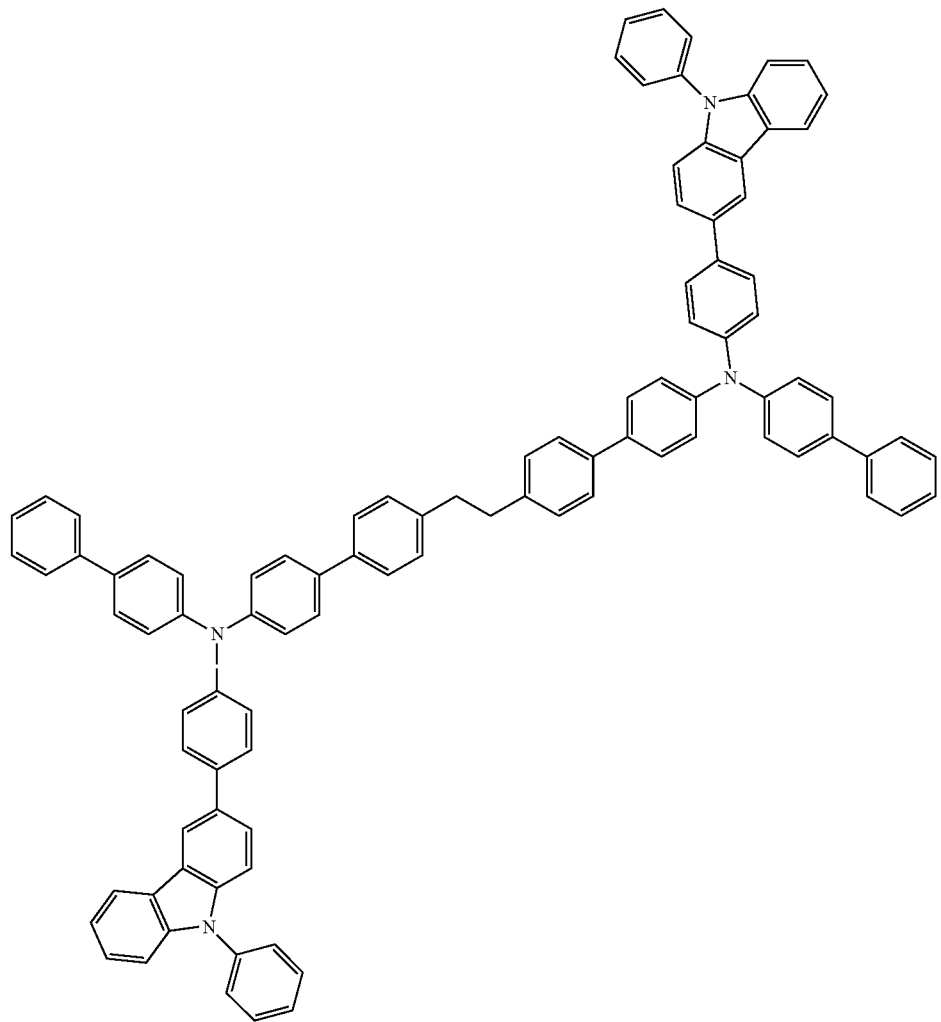
H13
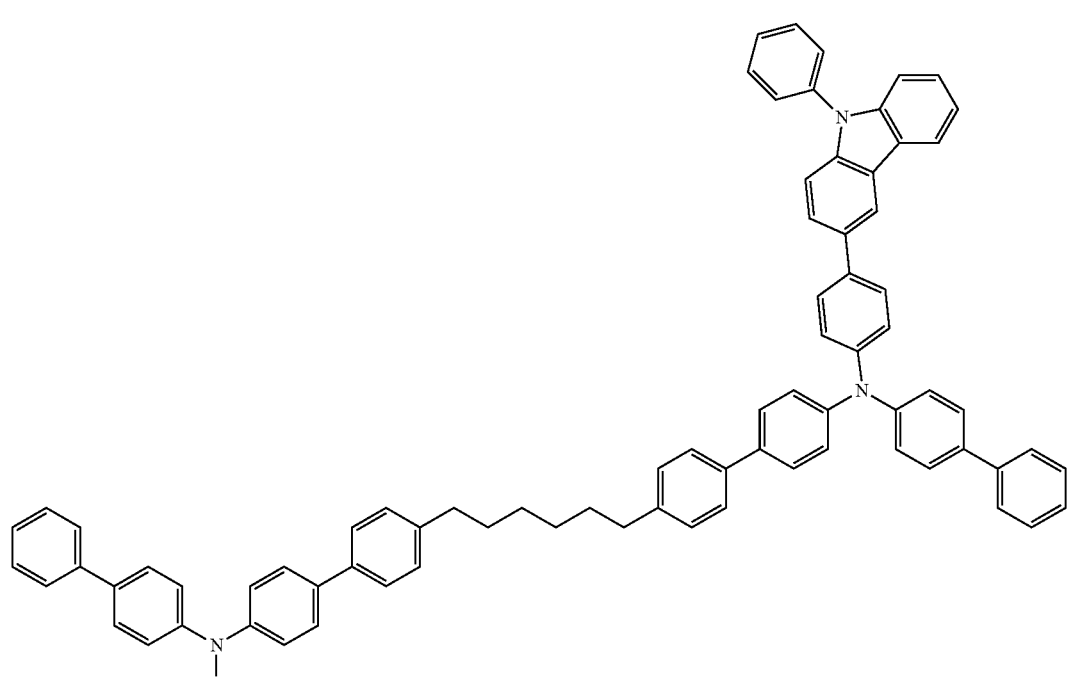

-continued
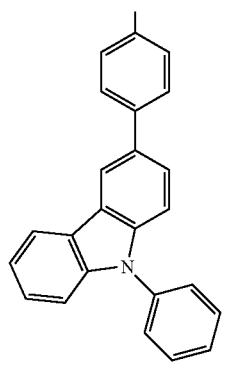
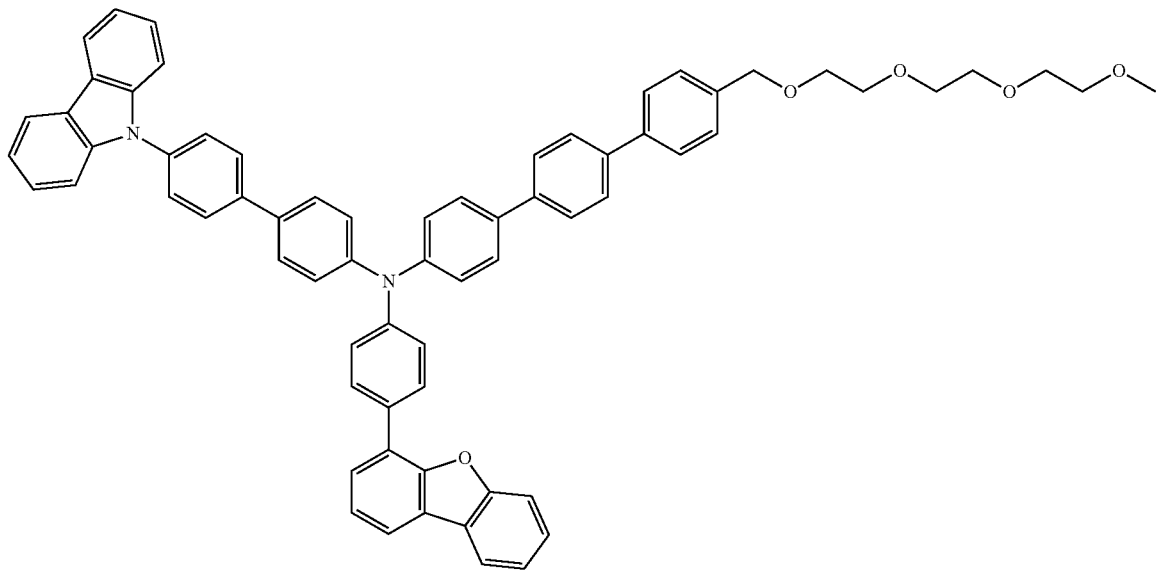
H14
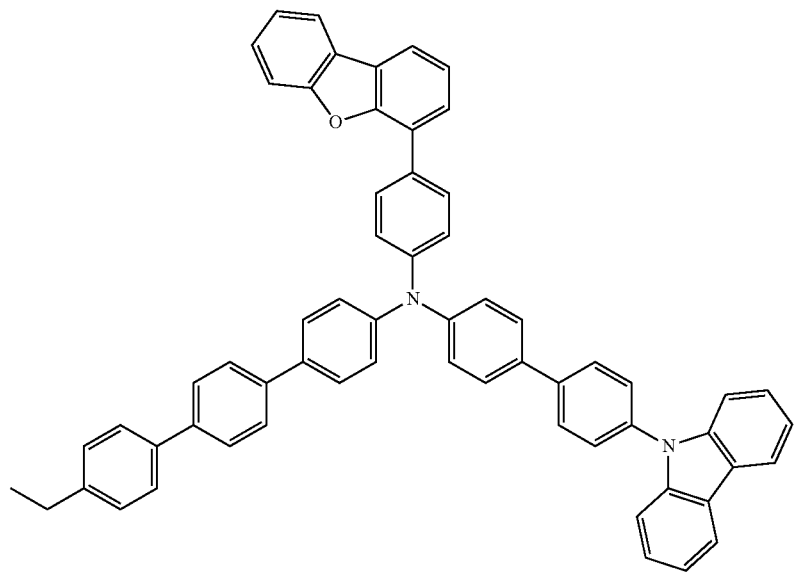

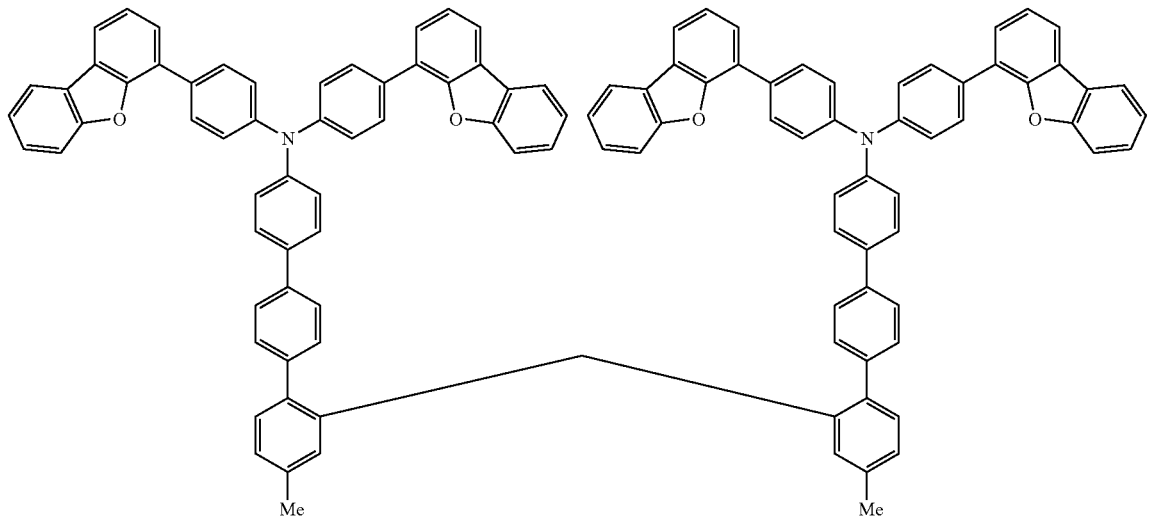

H15

H16

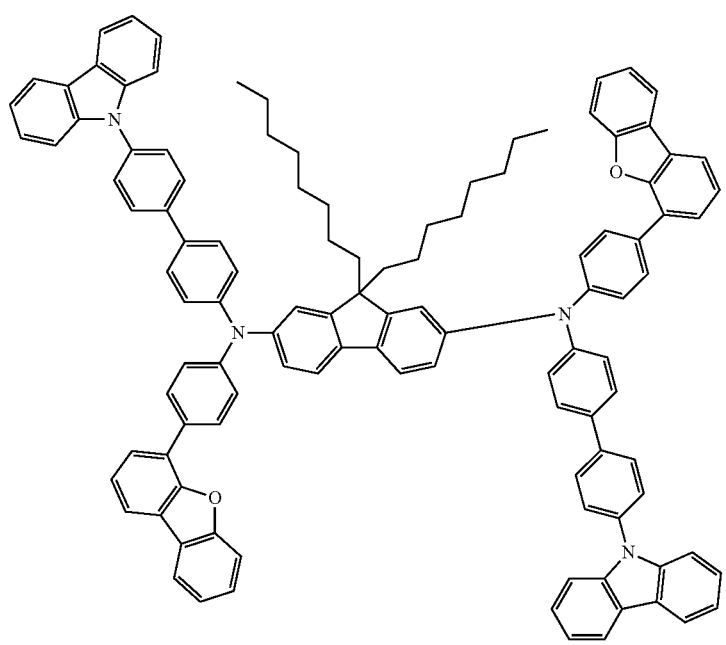

Example 17

Production and Evaluation of Organic EL Device

A glass substrate, measuring 25 mm by 75 mm by 1.1 mm thick, with an ITO transparent electrode (manufactured by GEOMATIC Co, Ltd.) was subjected to ultrasonic cleaning in isopropyl alcohol for 5 minutes and then to UV ozone cleaning for 30 minutes. A mixture of polyethylene dioxythiophene polystyrene sulfonic acid (PEDOT: PSS) (PSS is an acceptor) which is used for a hole-injecting layer was deposited by spin coating to form a 10 nm-thick film on the cleaned glass substrate with a transparent electrode.

Subsequently, a xylene solution (1.0 weight %) of Compound H1 prepared in Example 1 was prepared as a hole-transporting material and was deposited by spin coating to form a 40 nm-thick film. The film was dried at 100° C. for 30 minutes to obtain a uniform hole-transporting layer.

Next, Compound EM1 was further deposited to form a 40 nm-thick emitting layer. At the same time, as a material for the emitting layer, Amine compound D1 having the following styryl group was deposited in such a way that the weight ratio of EM1 and D1 became 40:2. On the film, the following Alq was deposited to form a 10 nm-thick film. The film obtained functions as an electron-injecting layer.

Thereafter, Li (Li source: manufactured by SAES getters) as a reducing dopant and Alq were subjected to binary deposition to form an Alq:Li film (film thickness: 10 nm) as an electron-injecting layer (cathode). Metal Al was deposited on the above Alq:Li film to form a metal cathode. Glass-encapsulation was conducted in nitrogen to produce an organic EL device.

The performances of the organic EL device produced were evaluated by applying electric current. The organic EL device emitted blue light and had a luminous efficiency of 7.0 cd/A and a half-luminance lifetime LT50 at room temperature of 4000 hr @1000 cd/m². When the organic EL device produced was driven in an oven of 60° C., it had a half-luminance lifetime LT50 of 1760 hr @1000 cd/m². The ratio of the half-luminance lifetime at 60° C. relative to that at room temperature was 0.44. The results were shown in Table 1

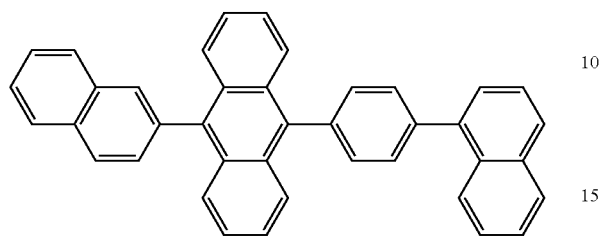

EM1

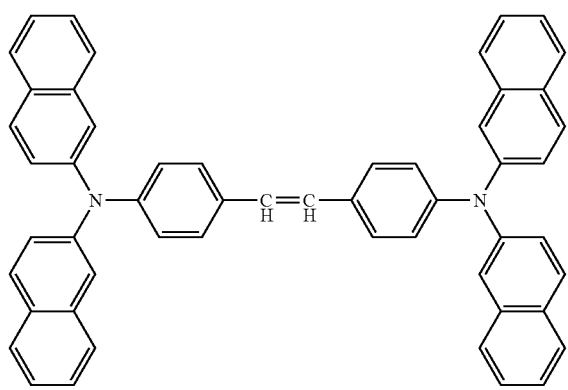

D1

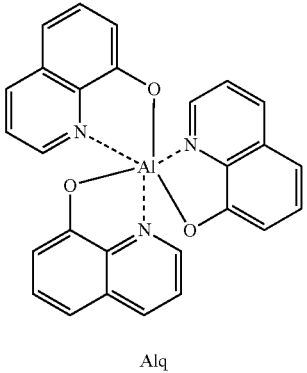

Alq

Examples 18-32

Organic EL devices were produced and evaluated in the same manner as in Example 17 except that the hole-transporting materials shown in Table 1 were used as the hole-transporting material instead of Compound H1. The results were shown in Table 1.

Comparative Example 1

An organic EL devices was produced and evaluated in the same manner as in Example 17 except that the hole-transporting material (Comparative compound 1) shown in Table 1 was used as the hole-transporting material instead of Compound H1.

Meanwhile, the solubility of Comparative compound 1 in xylene was insufficient, whereby the hole-transporting layer obtained was non-uniform.

The performances of the organic EL device produced were evaluated by applying electric current. The organic EL device emitted blue light and had a luminous efficiency of 2.3 cd/A and a half-luminance lifetime LT50 at room temperature of 500 hr @1000 cd/m². When the produced organic EL device was driven in an oven of 60° C., it had a half-luminance lifetime LT50 of 100 hr @1000 cd/m². The ratio of the half-luminance lifetime at 60° C. relative to that at room temperature was 0.20. The results were shown in Table 1.

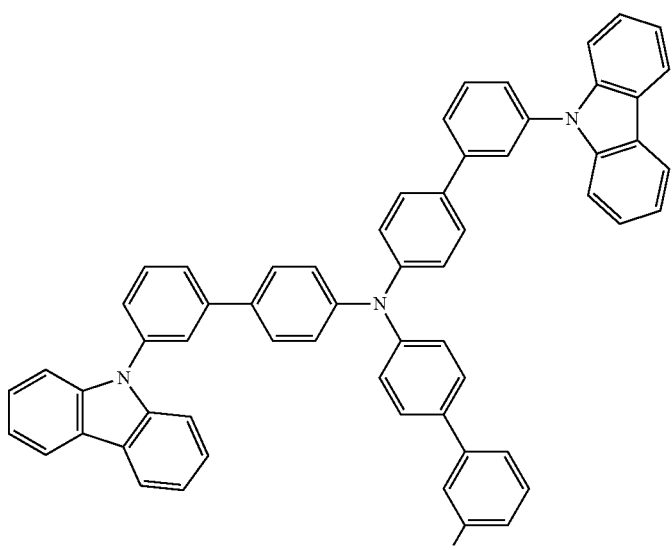

Comparative compound 1

-continued

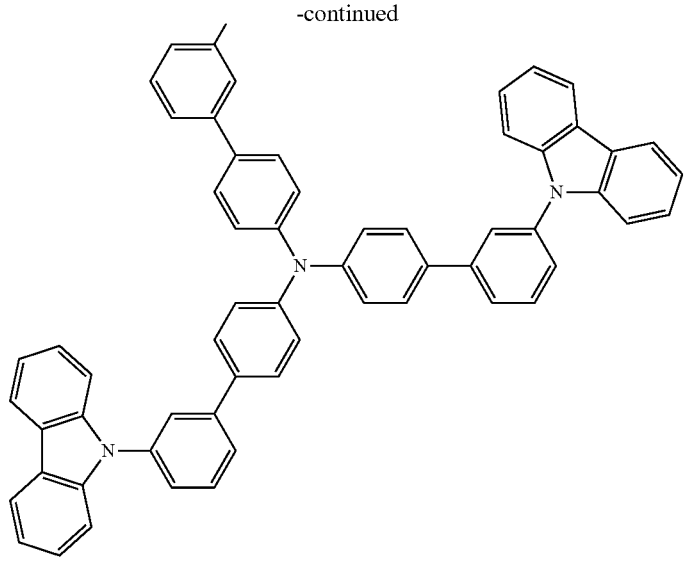

Comparative Example 2

An organic EL device was produced in the same manner as in Example 17 except that Comparative compound 2 was used as the hole-transporting material instead of Compound H1.

However, since the hole-transporting layer obtained had a high non-uniformity, the organic EL device produced could not emit due to leakage current.

Comparative compound 2

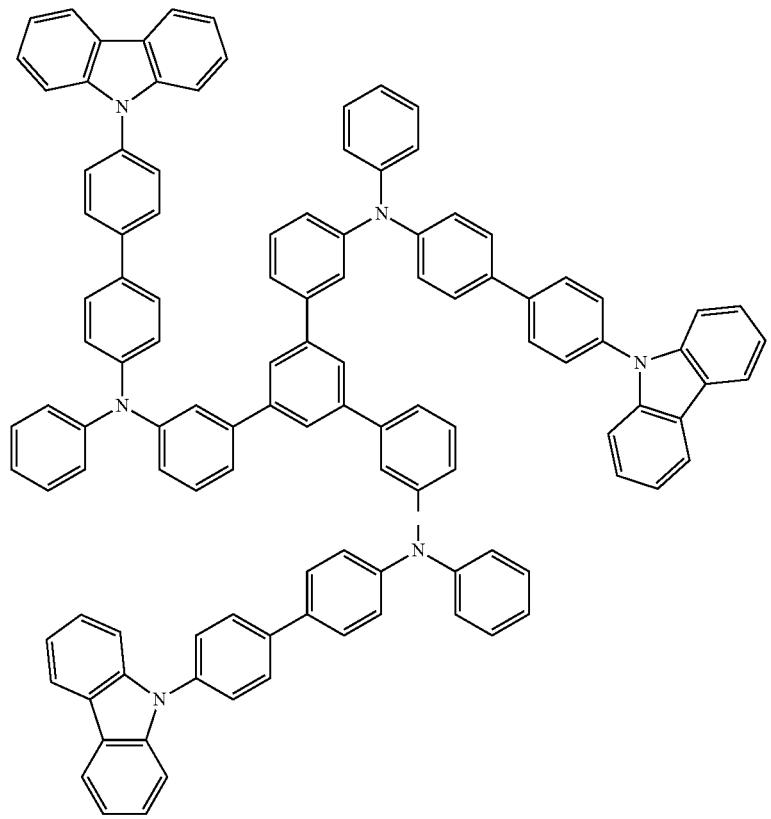

TABLE 1

| | Hole-transporting material | Emitting color | Luminous efficiency (cd/A) | Half-luminance lifetime at RT (hr@1000 cd/m²) | Half-luminance lifetime at 60° C. (hr@1000 cd/m²) | Ratio of lifetime 60° C./RT |
|---|---|---|---|---|---|---|
| Ex. 17 | H1 | Blue | 7.0 | 4000 | 1760 | 0.44 |
| Ex. 18 | H2 | Blue | 7.1 | 3800 | 1500 | 0.39 |
| Ex. 19 | H3 | Blue | 7.2 | 3800 | 1520 | 0.40 |
| Ex. 20 | H4 | Blue | 7.0 | 3700 | 1600 | 0.43 |
| Ex. 21 | H5 | Blue | 6.9 | 3700 | 1570 | 0.42 |
| Ex. 22 | H6 | Blue | 7.0 | 3800 | 1700 | 0.45 |
| Ex. 23 | H7 | Blue | 6.9 | 3900 | 1650 | 0.42 |
| Ex. 24 | H8 | Blue | 6.8 | 3800 | 1600 | 0.42 |
| Ex. 25 | H9 | Blue | 7.2 | 4200 | 1800 | 0.43 |
| Ex. 26 | H10 | Blue | 7.1 | 4100 | 1750 | 0.43 |
| Ex. 27 | H11 | Blue | 6.9 | 3800 | 1600 | 0.42 |
| Ex. 28 | H12 | Blue | 6.9 | 3700 | 1580 | 0.43 |
| Ex. 29 | H13 | Blue | 6.9 | 3800 | 1610 | 0.42 |
| Ex. 30 | H14 | Blue | 6.8 | 3700 | 1550 | 0.42 |
| Ex. 31 | H15 | Blue | 6.8 | 3700 | 1500 | 0.41 |
| Ex. 32 | H16 | Blue | 7.1 | 3900 | 1620 | 0.42 |
| Com. Ex. 1 | Comparative compound 1 | Blue | 2.3 | 500 | 100 | 0.20 |

From the results shown in Table 1, it can be understood that the organic EL devices using the aromatic amine derivatives of the invention have a higher luminous efficiency, a longer lifetime and a smaller degree of decreasing lifetime even when driven at high temperatures, as compared with organic EL devices using Comparative compounds which belong to the same aromatic amine derivatives.

INDUSTRIAL APPLICABILITY

According to the invention, an aromatic amine derivative which is useful as a hole-injecting and/or -transporting material of an organic device, in particular an organic EL device and the like can be provided. Also, a practical organic EL device can be provided which has excellent device performances such as a lifetime, a luminous efficiency and the like, and a small deterioration even when driven at high temperatures which are particularly practical for displays and lighting application.

Furthermore, according to the invention, since a hole-injecting and/or -transporting layer can be formed uniformly by coating methods, the organic EL device of the invention was suitable for reducing cost or growing in size of screen in displays and lighting application.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification are incorporated herein by reference in its entirety.

The invention claimed is:
1. An aromatic amine derivative represented by formula (1):

$$[Z\!-\!]_n L, \quad (1)$$

wherein:

Zs are independently a group represented by the following formula (2):

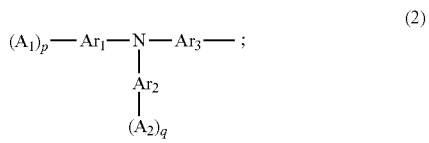

L is a-linking group comprising one of the following groups, the linking group optionally comprising a substituent:

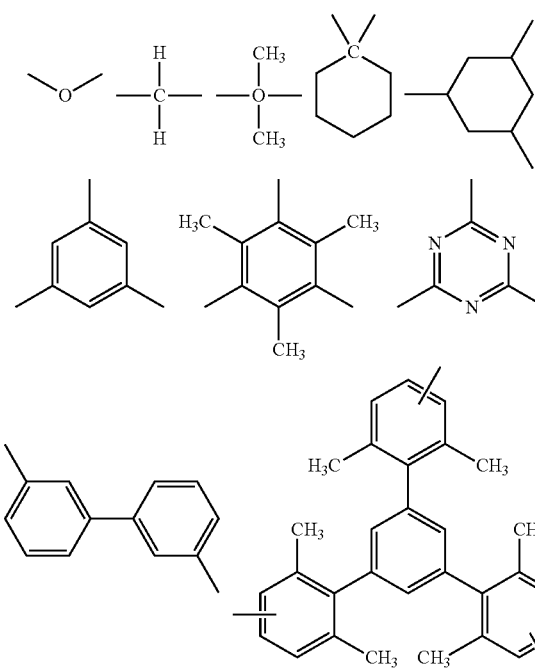

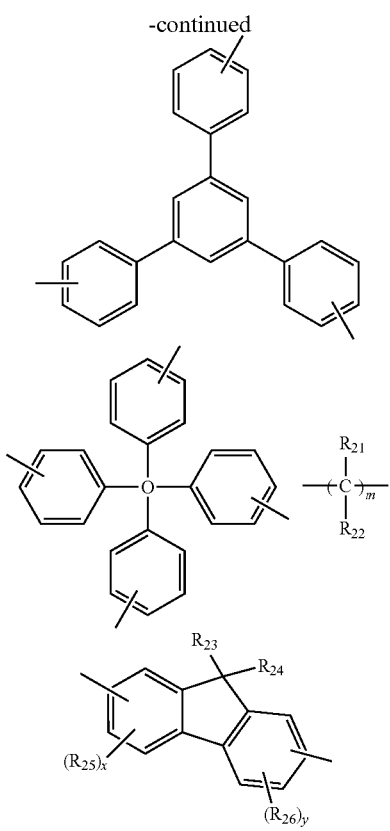

wherein $R_{21}$ and $R_{22}$ are independently a hydrogen atom, a methyl group, an ethyl group, a propyl group, an isopropyl group, a butyl group, an isobutyl group or a t-butyl group, and m is an integer of 2 to 20; and $R_{23}$, $R_{24}$, $R_{25}$ and $R_{26}$ are independently a hydrogen atom, a linear or branched alkyl group having 1 to 20 carbon atoms, a linear or branched alkenyl group having 2 to 20 carbon atoms, a cycloalkyl group having 3 to 20 carbon atoms, a trialkylsilyl group having an alkyl group having 1 to 20 carbon atoms, a triarylsilyl group having an aryl group having 6 to 24 ring carbon atoms, an alkylarylsilyl group having an alkyl group having 1 to 20 carbon atoms and an aryl group having 6 to 24 ring carbon atoms, an aryl group having 6 to 24 ring carbon atoms or a heteroaryl group having 5 to 24 ring atoms, $R_{23}$ and $R_{24}$, $R_{25}$ or $R_{26}$ may be bonded to each other to form a saturated or unsaturated ring, x is an integer of 1 to 3 and y is an integer of 1 to 3, provided that when x is an integer of 2 or more, $R_{25s}$ independently may be the same or different, and when y is an integer of 2 or more, $R_{26s}$ independently may be the same or different;

n is an integer of 2 to 4;

$Ar_1$ is independently a substituted or unsubstituted (1+p)-valent aromatic hydrocarbon group having 6 to 25 ring carbon atoms or a substituted or unsubstituted (1+p)-valent aromatic heterocyclic group, wherein the aromatic heterocyclic group is a pyrrole, an indole, an isoindole, a furan, a benzofuran, an isobenzofuran, a carbazole, an acridine, a phenazine, a phenothiazine, a phenoxazine, or a thiophene;

$Ar_2$ is independently a substituted or unsubstituted (1+q)-valent aromatic hydrocarbon group having 6 to 25 ring carbon atoms or a substituted or unsubstituted (1+q)-valent aromatic heterocyclic group, wherein the aromatic heterocyclic group is a pyrrole, an indole, an isoindole, a furan, a benzofuran, an isobenzofuran, a carbazole, an acridine, a phenazine, a phenothiazine, a phenoxazine, or a thiophene;

$Ar_3$ is independently a divalent group represented by formula (10):

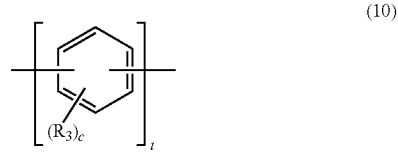

wherein $R_3$ is independently a group selected from the group consisting of a linear or branched alkyl group having 1 to 15 carbon atoms, a linear or branched alkenyl group having 2 to 15 carbon atoms, a cycloalkyl group having 3 to 15 carbon atoms, a trialkylsilyl group having an alkyl group having 1 to 15 carbon atoms, a triarylsilyl group having an aryl group having 6 to 25 ring carbon atoms, an alkylarylsilyl group having an alkyl group having 1 to 15 carbon atoms and an aryl group having 6 to 25 ring carbon atoms, an awl group having 6 to 25 ring carbon atoms, a heteroaryl group having 5 to 25 ring atoms, a halogen atom and a cyano group, $R_3$ may be bonded to each other to form a saturated or unsaturated ring, c is an integer of 0 to 4; and t is an integer of 1 to 3;

$A_1$ and $A_2$ are independently a monovalent group represented by formula (3):

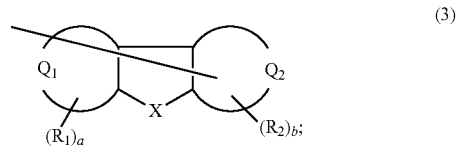

p and q are independently an integer of 0 or 1, provided that p+q≥1;

X is —O—, —S—, —N— or —N($R_a$)—;

Ra is a group selected from the group consisting of a hydrogen atom, a linear or branched alkyl group having 1 to 15 carbon atoms, a linear or branched alkenyl group having 2 to 15 carbon atoms, a cycloalkyl group having 3 to 15 carbon atoms, a trialkylsilyl group having an alkyl group having 1 to 15 carbon atoms, a triarylsilyl group having an aryl group having 6 to 25 ring carbon atoms, an alkylarylsilyl group having an alkyl group having 1 to 15 carbon atoms and an aryl group having 6 to 25 ring carbon atoms, an aryl group having 6 to 25 ring carbon atoms and a heteroaryl group having 5 to 25 ring atoms, provided that the "X is —N—" means that X is a nitrogen atom and $Ar_1$ or $Ar_2$ is bonded to X;

$R_1$ and $R_2$ are independently a group selected from the group consisting of a linear or branched alkyl group having 1 to 15 carbon atoms, a linear or branched alkenyl group having 2 to 15 carbon atoms, a cycloalkyl group having 3 to 15 carbon atoms, a trialkylsilyl group having an alkyl group having 1 to 15 carbon atoms, a triarylsilyl group having an aryl group having 6 to 25 ring carbon atoms, an alkylarylsilyl group having an alkyl group having 1 to 15 carbon atoms and an aryl group having 6 to 25 ring carbon atoms, an aryl group having 6 to 25 ring carbon atoms, a heteroaryl group having 5 to 25 ring atoms, a halogen atom and a cyano group, such that adjacent $R_1$s, adjacent $R_2$s and adjacent $R_1$ and $R_2$ are optionally bonded to each other to form a saturated or unsaturated ring;

a and b are independently an integer of 0 to 3;

$Q_1$ and $Q_2$ are a benzene ring, provided that:

in the group represented by the formula (2), when $(A_1)_p$-$Ar_1$— is represented by formula (4):

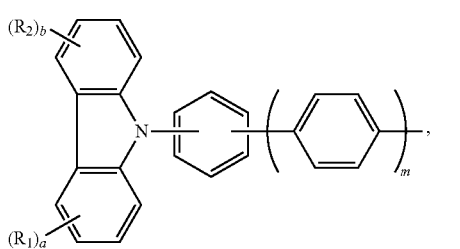

and q is 1, X of $A_2$ is —O—, —S— or —N($R_a$)—; and in the group represented by the formula (2), when $(A_1)_p$-$Ar_1$— is represented by formula (4) and q is 0, $Ar_2$ is a substituted or unsubstituted aromatic hydrocarbon group having 9 to 25 ring carbon atoms which has a polycyclic structure and $Ar_2$ is an asymmetric group relative to the bond axis from $Ar_2$ to the nitrogen atom to which $Ar_2$ is bonded;

$R_1$, $R_2$, a and b are the same as those in the formula (3); and m is an integer of 0 to 2; and formula (1) optionally comprises a deuterium.

2. The aromatic amine derivative according to claim 1, wherein $A_1$ and $A_2$ are independently a monovalent group represented by formula (5) or (6):

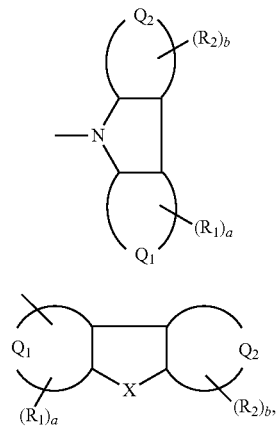

wherein:

X is —O—, —S— or —N($R_a$)—;

Ra is a group selected from the group consisting of a hydrogen atom, a linear or branched alkyl group having 1 to 15 carbon atoms, a linear or branched alkenyl group having 2 to 15 carbon atoms, a cycloalkyl group having 3 to 15 carbon atoms, a trialkylsilyl group having an alkyl group having 1 to 15 carbon atoms, a triarylsilyl group having an aryl group having 6 to 25 ring carbon atoms, an alkylarylsilyl group having an alkyl group having 1 to 15 carbon atoms and an aryl group having 6 to 25 ring carbon atoms, an aryl group having 6 to 25 ring carbon atoms and a heteroaryl group having 5 to 25 ring atoms, provided that the "X is —N—" means that X is a nitrogen atom and $Ar_1$ or $Ar_2$ is bonded to X;

$R_1$ and $R_2$ are independently a group selected from the group consisting of a linear or branched alkyl group having 1 to 15 carbon atoms, a linear or branched alkenyl group having 2 to 15 carbon atoms, a cycloalkyl group having 3 to 15 carbon atoms, a trialkylsilyl group having an alkyl group having 1 to 15 carbon atoms, a triarylsilyl group having an aryl group having 6 to 25 ring carbon atoms, an alkylarylsilyl group having an alkyl group having 1 to 15 carbon atoms and an aryl group having 6 to 25 ring carbon atoms, an awl group having 6 to 25 ring carbon atoms, a heteroaryl group having 5 to 25 ring atoms, a halogen atom and a cyano group, such that adjacent $R_1$s, adjacent $R_2$s and adjacent $R_1$ and $R_2$ are optionally bonded to each other to form a saturated or unsaturated ring;

a and b are independently an integer of 0 to 3;

$Q_1$ and $Q_2$ are a benzene ring, provided that:

in the group represented by formula (2):

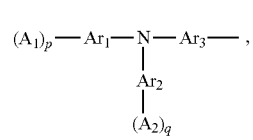

when $(A_1)_p$-$Ar_1$— is represented by formula (4):

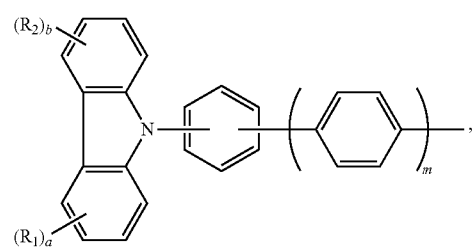

and q is 1, X of $A_2$ is —O—, —S— or —N($R_a$)—; and in the group represented by the formula (2), when $(A_1)_p$-$Ar_1$— is represented by formula (4) and q is 0, $Ar_2$ is a substituted or unsubstituted aromatic hydrocarbon group having 9 to 25 ring carbon atoms having a polycyclic structure and $Ar_2$ is an asymmetric group relative to the bond axis from $Ar_2$ to the nitrogen atom to which $Ar_2$ is bonded;

in formula (4), $R_1$, $R_2$, a and b are the same as defined above; and m is an integer of 0 to 2.

3. The aromatic amine derivative according to claim 2, wherein $A_1$ and $A_2$ are independently a monovalent group represented by the formula (6):

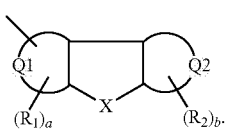
(6)

4. The aromatic amine derivative according to claim 1, wherein $A_1$ and $A_2$ are independently a monovalent group represented by formula (7):

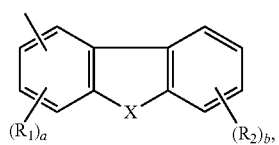
(7)

wherein:

X is —O—, —S— or —N($R_a$)—;

$R_a$ is a group selected from the group consisting of a hydrogen atom, a linear or branched alkyl group having 1 to 15 carbon atoms, a linear or branched alkenyl group having 2 to 15 carbon atoms, a cycloalkyl group having 3 to 15 carbon atoms, a trialkylsilyl group having an alkyl group having 1 to 15 carbon atoms, a triarylsilyl group having an aryl group having 6 to 25 ring carbon atoms, an alkylarylsilyl group having an alkyl group having 1 to 15 carbon atoms and an aryl group having 6 to 25 ring carbon atoms, an aryl group having 6 to 25 ring carbon atoms and a heteroaryl group having 5 to 25 ring atoms, provided that the "X is —N—" means that X is a nitrogen atom and $Ar_1$ or $Ar_2$ is bonded to X;

$R_1$ and $R_2$ are independently a group selected from the group consisting of a linear or branched alkyl group having 1 to 15 carbon atoms, a linear or branched alkenyl group having 2 to 15 carbon atoms, a cycloalkyl group having 3 to 15 carbon atoms, a trialkylsilyl group having an alkyl group having 1 to 15 carbon atoms, a triarylsilyl group having an aryl group having 6 to 25 ring carbon atoms, an alkylarylsilyl group having an alkyl group having 1 to 15 carbon atoms and an aryl group having 6 to 25 ring carbon atoms, an aryl group having 6 to 25 ring carbon atoms, a heteroaryl group having 5 to 25 ring atoms, a halogen atom and a cyano group, such that adjacent $R_1$s, adjacent $R_2$s and adjacent $R_1$ and $R_2$ are optionally bonded to each other to form a saturated or unsaturated ring; and a and b are independently an integer of 0 to 3.

5. The aromatic amine derivative according to claim 1, wherein $A_1$ and $A_2$ are independently a monovalent group represented by formula (8-1) or (8-2):

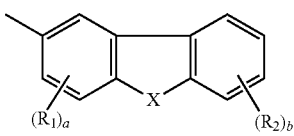
(8-1)

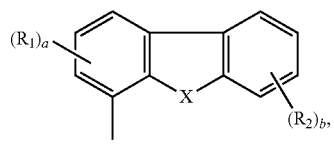
(8-2)

wherein:

X is —O—, —S— or —N($R_a$)—;

$R_a$ is a group selected from the group consisting of a hydrogen atom, a linear or branched alkyl group having 1 to 15 carbon atoms, a linear or branched alkenyl group having 2 to 15 carbon atoms, a cycloalkyl group having 3 to 15 carbon atoms, a trialkylsilyl group having an alkyl group having 1 to 15 carbon atoms, a triarylsilyl group having an aryl group having 6 to 25 ring carbon atoms, an alkylarylsilyl group having an alkyl group having 1 to 15 carbon atoms and an aryl group having 6 to 25 ring carbon atoms, an aryl group having 6 to 25 ring carbon atoms and a heteroaryl group having 5 to 25 ring atoms, provided that the "X is —N—" means that X is a nitrogen atom and $Ar_1$ or $Ar_2$ is bonded to X;

$R_1$ and $R_2$ are independently a group selected from the group consisting of a linear or branched alkyl group having 1 to 15 carbon atoms, a linear or branched alkenyl group having 2 to 15 carbon atoms, a cycloalkyl group having 3 to 15 carbon atoms, a trialkylsilyl group having an alkyl group having 1 to 15 carbon atoms, a triarylsilyl group having an aryl group having 6 to 25 ring carbon atoms, an alkylarylsilyl group having an alkyl group having 1 to 15 carbon atoms and an aryl group having 6 to 25 ring carbon atoms, an aryl group having 6 to 25 ring carbon atoms, a heteroaryl group having 5 to 25 ring atoms, a halogen atom and a cyano group, such that adjacent $R_1$s, adjacent $R_2$s and adjacent $R_1$ and $R_2$ are optionally bonded to each other to form a saturated or unsaturated ring; and a and b are independently an integer of 0 to 3.

6. The aromatic amine derivative of claim 1, wherein at least one of $Ar_1$ and $Ar_2$ is a linking group selected from the group consisting of a phenylene group, a biphenylene group, a terphenylene group, a naphthylene group and a phenanthrenylene group.

7. The aromatic amine derivative of claim 1, wherein at least one of $Ar_1$ and $Ar_2$ is a divalent group represented by formula (9):

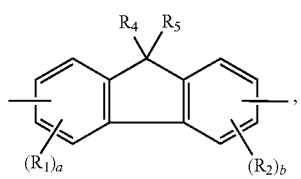
(9)

wherein:

$R_4$ and $R_5$ are independently a group selected from the group consisting of a hydrogen atom, a linear or branched alkyl group having 1 to 15 carbon atoms, a linear or branched alkenyl group having 2 to 15 carbon atoms, a cycloalkyl group having 3 to 15 carbon atoms, a trialkylsilyl group having an alkyl group having 1 to 15 carbon atoms, a triarylsilyl group having an aryl group having 6 to 25 ring carbon atoms, an alkylarylsilyl group having an alkyl group having 1 to 15 carbon atoms and an aryl group having 6 to 25 ring carbon atoms, an aryl group having 6 to 25 ring carbon atoms and a heteroaryl group having 5 to 25 ring atoms, such that $R_4$ and $R_5$ are optionally may be bonded to each other to form a saturated or unsaturated ring;

$R_1$ and $R_2$ are independently a group selected from the group consisting of a linear or branched alkyl group having 1 to 15 carbon atoms, a linear or branched alkenyl group having 2 to 15 carbon atoms, a cycloalkyl group having 3 to 15 carbon atoms, a trialkylsilyl group having an alkyl group having 1 to 15 carbon atoms, a triarylsilyl group having an aryl group having 6 to 25 ring carbon atoms, an alkylarylsilyl group having an alkyl group having 1 to 15 carbon atoms and an aryl group having 6 to 25 ring carbon atoms, an aryl group having 6 to 25 ring carbon atoms, a heteroaryl group having 5 to 25 ring atoms, a halogen atom and a cyano group, such that adjacent $R_1$s, adjacent $R_2$s and adjacent $R_1$ and $R_2$ are optionally bonded to each other to form a saturated or unsaturated ring; and a and b are independently an integer of 0 to 3.

8. The aromatic amine derivative of claim 1, wherein in the formula (2), at least one Z has different $(A_1)_p$-$Ar_1$— and $(A_2)_q$-$Ar_2$—.

9. The aromatic amine derivative of claim 1, wherein Zs differ from each other.

10. An organic device material, comprising the aromatic amine derivative of claim 1.

11. A hole-injecting and hole-transporting material, comprising the aromatic amine derivative of claim 1.

12. An organic electroluminescence device material, comprising the aromatic amine derivative of claim 1.

13. An organic electroluminescence device, comprising an anode, a cathode and one or more organic thin film layers comprising at least an emitting layer therebetween,
wherein at least one of the organic thin film layers comprises the aromatic amine derivative of claim 1.

14. The organic electroluminescence device according to claim 13, wherein the one or more organic thin film layers comprise at least one of a hole-transporting layer and a hole-injecting layer, and the at least one of a hole-transporting layer and a hole-injecting layer comprises the aromatic amine derivative.

15. The organic electroluminescence device according to claim 14, wherein the at least one of a hole-transporting layer and a hole-injecting layer comprises the aromatic amine derivative as a main component.

16. The organic electroluminescence device of claim 13, wherein the one or more organic thin film layers comprise at least one of a hole-transporting layer and a hole-injecting layer, and the at least one of a hole-transporting layer and a hole-injecting layer comprises an acceptor material.

17. The aromatic amine derivative according to claim 1, wherein the aryl group is a phenyl group, a 1-naphthyl group, a 2-naphythyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, naphthacenyl group, a 2-naphthacenyl group, a 9-naphthacenyl group, a 1-pyrenyl group, a 2-pyrenyl group, a 4-pyrenyl group, a biphenyl-2-yl group, a biphenyl-3-yl group, a biphenyl-4-yl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenyl-4-yl group, a 4"-t-butyl-p-terphenyl-4-yl group, a fluorene-1-yl group, a fluorene-2-yl group, a fluorene-3-yl group or a fluorine-4-yl group.

18. The aromatic amine derivative according to claim 1, wherein the alkyl group is a methyl group, an ethyl group, a propyl group, an isopropyl group, an n-butyl group, an isobutyl group, a sec-butyl group, a tert-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group or a 1,2,3-trihydroxypropyl group.

19. The aromatic amine derivative according to claim 1, wherein the alkenyl group is a substituent having an unsaturated bond in a molecule of a methyl group, an ethyl group, a propyl group, an isopropyl group, an n-butyl group, an isobutyl group, a sec-butyl group, a tert-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group or a 1,2,3-trihydroxypropyl group.

20. The aromatic amine derivative according to claim 1, wherein the cycloalkyl group is a cyclopropyl group, a cyclobutyl group, a cyclopentyl group, a cyclohexyl group, a cyclopentylmethyl group, a cyclohexylmethyl group, a cyclohexylethyl group, a 4-fluorocyclohexyl group, a 1-adamantyl group, a 2-adamantyl group, a 1-norbornyl group, or a 2-norbornyl group.

21. The aromatic amine derivative according to claim 1, wherein the trialkylsilyl group is a trimethylsilyl group, a vinyldimethylsilyl group, a triethylsilyl group, a tripropylsilyl group, a propyldimethylsilyl group, a tributylsilyl group, a t-butyldimethylsilyl group, a tripentylsilyl group, a triheptylsilyl group, or a trihexylsilyl group.

22. The aromatic amine derivative according to claim 1, wherein the triarylsilyl group is a triphenylsilyl group, or a trinaphthylsilyl group.

23. The aromatic amine derivative according to claim 1, wherein the alkylarylsilyl group is a dimethylphenylsilyl group, a diethylphenylsilyl group, a diphenylmethylsilyl group, or an ethyldiphenylsilyl group.

24. The aromatic amine derivative according to claim 1, wherein the heteroaryl group is a 1-pyrrolyl group, a 2-pyrrolyl group, a 3-pyrrolyl group, a pyradinyl group, a 2-pyrydinyl group, a 3-pyrydinyl group, a 4-pyrydinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 2-quinoxalynyl group, a 5-quinoxalynyl group, a 6-quinoxalynyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, a 8-phenanthridinyl group, a 9-phenanthridinyl group, a 10-phenanthridinyl group, a 1-acrydinyl group, a 2-acrydinyl group, a 3-acrydinyl group, a 4-acrydinyl group, a 9-acrydinyl group, a 1,7-phenanthroline-2-yl group, a 1,7-phenanthroline-3-yl group, a 1,7-phenanthroline-4-yl group, a 1,7-phenanthroline-5-yl group, a 1,7-phenanthroline-6-yl group, a 1,7-phenanthroline-8-yl group, a 1,7-phenanthroline-9-yl group, a 1,7-phenanthroline-10-yl group, a 1,8-phenanthroline-2-yl group, a 1,8-phenanthroline-3-yl group, a 1,8-phenanthroline-4-yl group, a 1,8-phenanthroline-5-yl group, a 1,8-phenanthroline-6-yl group, a 1,8-phenanthroline-7-yl group, a 1,8-phenanthroline-9-yl group, a 1,8-phenanthroline-10-yl group, a 1,9-phenanthroline-2-yl group, a 1,9-phenanthroline-3-yl group, a 1,9-phenanthroline-4-yl group, a 1,9-phenanthroline-5-yl group, a 1,9-phenanthroline-6-yl group, a 1,9-phenanthroline-7-yl group, a 1,9-phenanthroline-8-yl group, a 1,9-phenanthroline-10-yl group, a 1,10-phenanthroline-2-yl group, a 1,10-phenanthroline-3-yl group, a 1,10-phenanthroline-4-yl group, a 1,10-phenanthroline-5-yl group, a 2,9-phenanthroline-1-yl group, a 2,9-phenanthroline-3-yl group, a 2,9-phenanthroline-4-yl group, a 2,9-phenanthroline-5-yl group, a 2,9-phenanthroline-6-yl group, a 2,9-phenanthroline-7-yl group, a 2,9-phenanthroline-8-yl group, a 2,9-phenanthroline-10-yl group, a 2,8-phenanthroline-1-yl group, a 2,8-phenanthroline-3-yl group, a 2,8-phenanthroline-4-yl group, a 2,8-phenanthroline-5-yl group, a 2,8-phenanthroline-6-yl group, a 2,8-phenanthroline-7-yl group, a 2,8-phenanthroline-9-yl group, a 2,8-phenanthroline-10-yl group, a 2,7-phenanthroline-1-yl group, a 2,7-phenanthroline-3-yl group, a 2,7-phenanthroline-4-yl group, a 2,7-phenanthroline-5-yl group, a 2,7-phenanthroline-6-yl group, a 2,7-phenanthroline-8-yl group, a 2,7-phenanthroline-9-yl group, a 2,7-phenanthroline-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-methylpyrrole-1-yl group, a 2-methylpyrrole-3-yl group, a 2-methylpyrrole-4-yl group, a 2-methylpyrrole-5-yl group, a 3-methylpyrrole-1-yl group, a 3-methylpyrrole-2-yl group, a 3-methylpyrrole-4-yl group, a 3-methylpyrrole-5-yl group, a 2-t-butylpyrrole-4-yl group, a 3-(2-phenylpropyl)pyrrole-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, or a 4-t-butyl-3-indolyl group.

25. The aromatic amine derivative according to claim 1, wherein the halogen atom is a fluorine atom, a chlorine atom or a bromine atom.

\* \* \* \* \*

UNITED STATES PATENT AND TRADEMARK OFFICE
CERTIFICATE OF CORRECTION

PATENT NO. : 9,527,814 B2  
APPLICATION NO. : 13/496400  
DATED : December 27, 2016  
INVENTOR(S) : Tomoki Kato et al.

Page 1 of 3

It is certified that error appears in the above-identified patent and that said Letters Patent is hereby corrected as shown below:

In the Claims

Column 162, Lines 40-45,

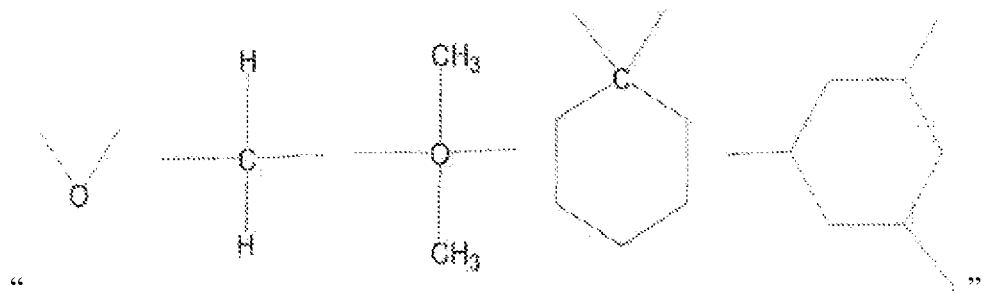

"

should read

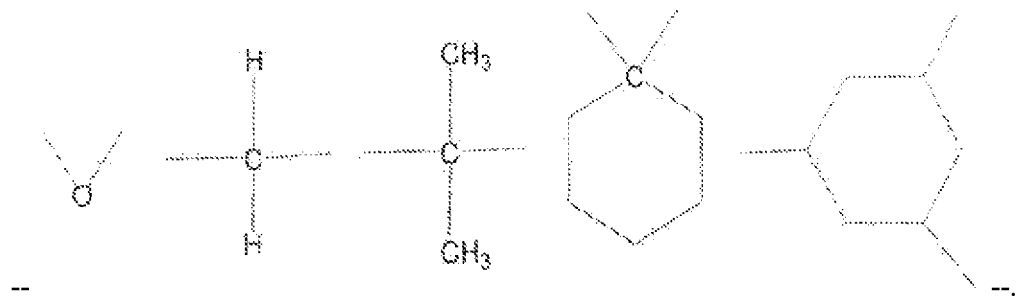

--.

Signed and Sealed this  
Eighteenth Day of April, 2017

Michelle K. Lee  
*Director of the United States Patent and Trademark Office*

CERTIFICATE OF CORRECTION (continued)
U.S. Pat. No. 9,527,814 B2

Column 163, Lines 15-20,

"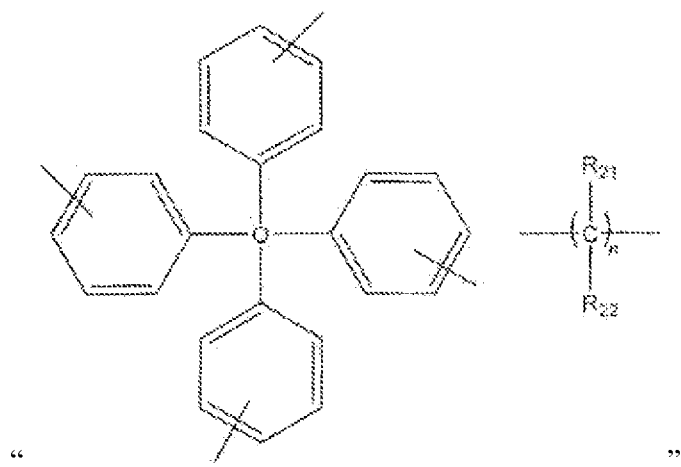"

should read

--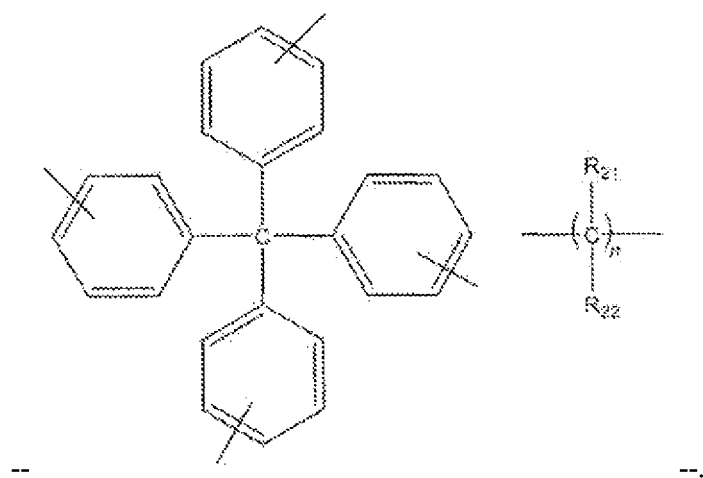--.

Column 164, Line 28, "awl" should read --aryl--.

Column 166, Line 22, "awl" should read --aryl--.

Column 167, Line 1,

"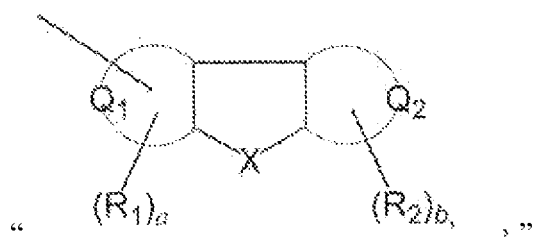,"

should read
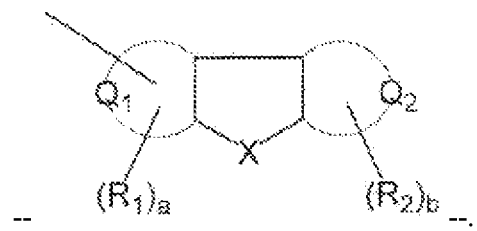
Column 169, Line 7, delete "may be".